(12) United States Patent
Leket-Mor et al.

(10) Patent No.: US 11,918,642 B2
(45) Date of Patent: Mar. 5, 2024

(54) HIV VACCINATION COMPOSITIONS COMPRISING VACCINIA VLPS AND PLANT-PRODUCED VLPS PRESENTING HIV ANTIGENS

(71) Applicant: ARIZONA BOARD OF REGENTS ON BEHALF OF ARIZONA STATE UNIVERSITY, Scottsdale, AZ (US)

(72) Inventors: Tsafrir S. Leket-Mor, Tempe, AZ (US); Bertram Jacobs, Tempe, AZ (US); Lydia Meador, Tempe, AZ (US); Karen Kibler, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 77 days.

(21) Appl. No.: 17/489,106

(22) Filed: Sep. 29, 2021

(65) Prior Publication Data
US 2022/0088178 A1    Mar. 24, 2022

Related U.S. Application Data

(63) Continuation of application No. 16/396,676, filed on Apr. 27, 2019, now abandoned.

(60) Provisional application No. 62/663,391, filed on Apr. 27, 2018.

(51) Int. Cl.
*A61K 39/21* (2006.01)
*C07K 14/16* (2006.01)
*A61K 39/00* (2006.01)

(52) U.S. Cl.
CPC ...... *A61K 39/21* (2013.01); *A61K 2039/5258* (2013.01); *A61K 2039/575* (2013.01); *C07K 14/161* (2013.01); *C07K 14/162* (2013.01); *C12N 2740/16034* (2013.01); *C12N 2740/16134* (2013.01); *C12N 2740/16234* (2013.01)

(58) Field of Classification Search
None
See application file for complete search history.

(56) References Cited

PUBLICATIONS

Kessans et al., PLoS One, Mar. 17, 2016, 11(3): e0151842. (Year: 2016).*
Meador, Searching for an HIV Vaccine: A Heterologous Prime-boost System using Replicating Vaccinia Virus and Plant-produced Virus-like Particles, Dissertation, Aug. 2016. (Year: 2016).*
Perdiguero et al., Journal of Virology, 2014, 89:970-988. (Year: 2014).*
Regnard et al., Plant Biotechnology Journal, 2010, 8(1):38-46. (Year: 2010).*

* cited by examiner

*Primary Examiner* — Nicole Kinsey White
(74) *Attorney, Agent, or Firm* — BOOTH UDALL FULLER, PLC

(57) ABSTRACT

Disclosed are compositions for generating an immune response against human immunodeficiency virus (HIV) and their methods of uses.

Figure 1A:
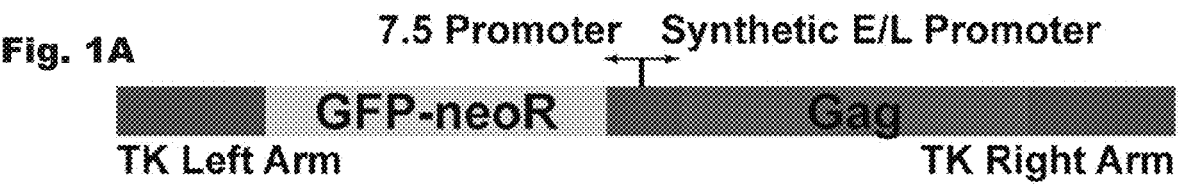
Figure 1B:
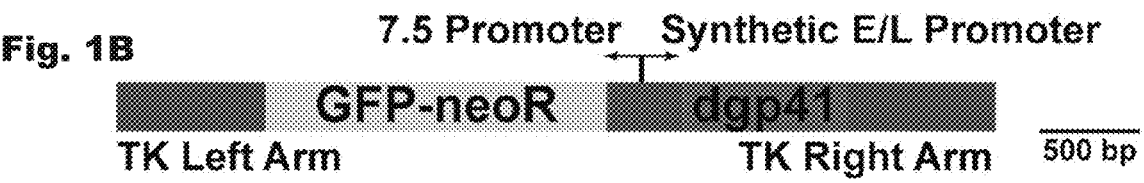

19 Claims, 12 Drawing Sheets
(11 of 12 Drawing Sheet(s) Filed in Color)

Specification includes a Sequence Listing.

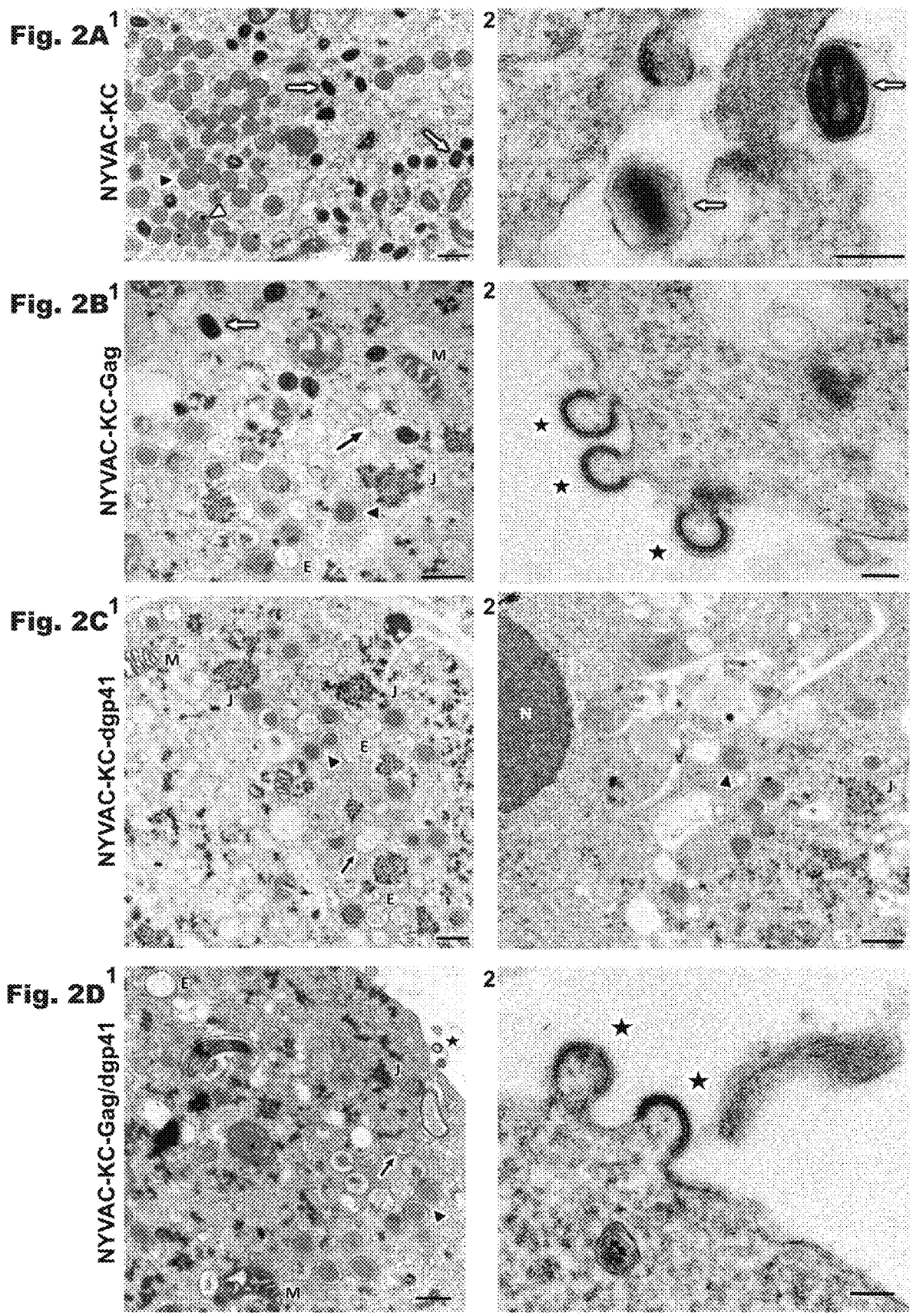

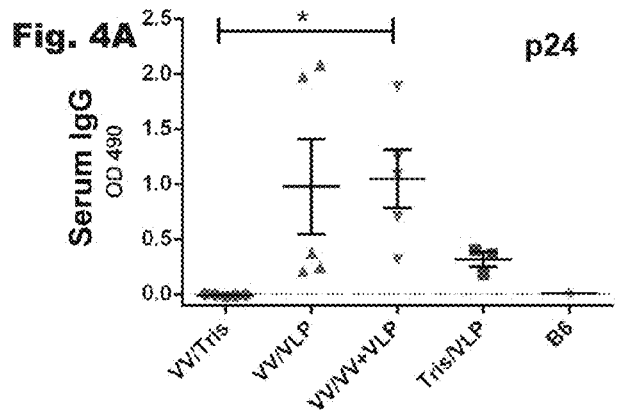
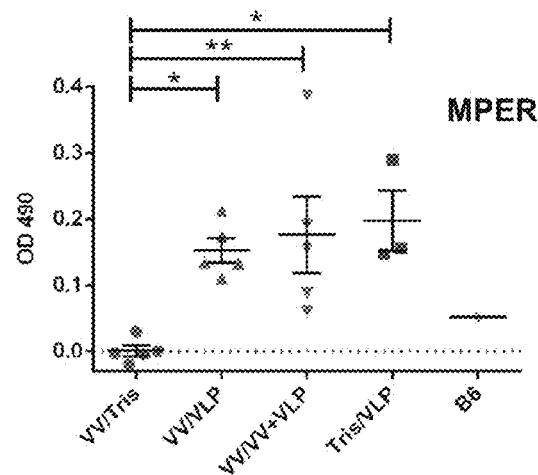
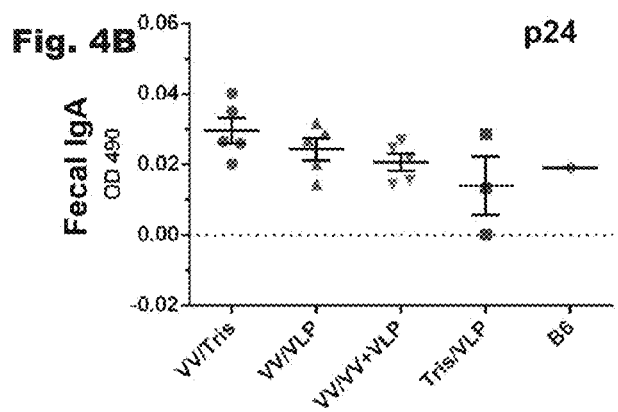
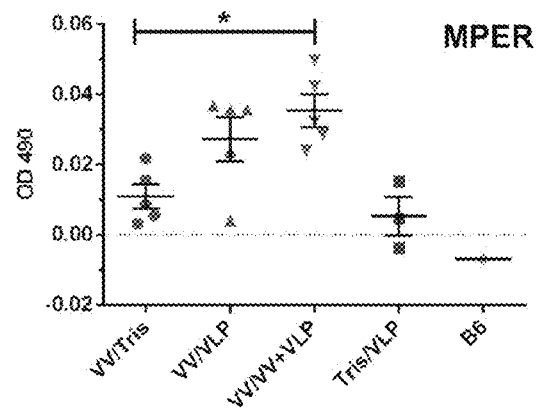
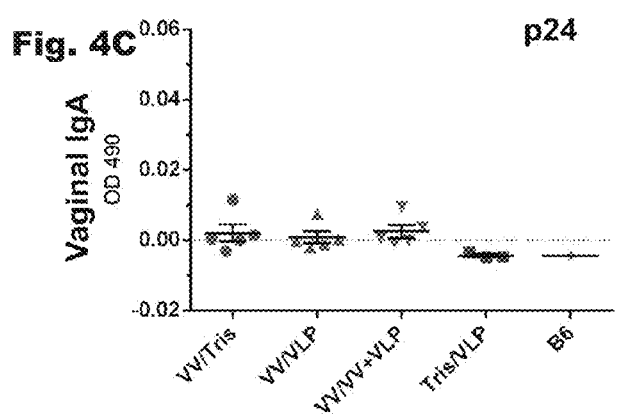
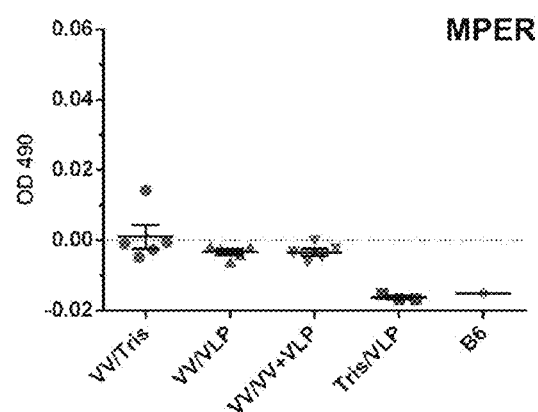

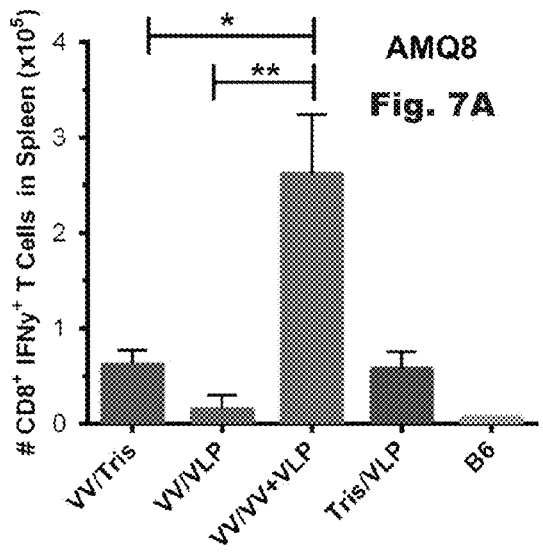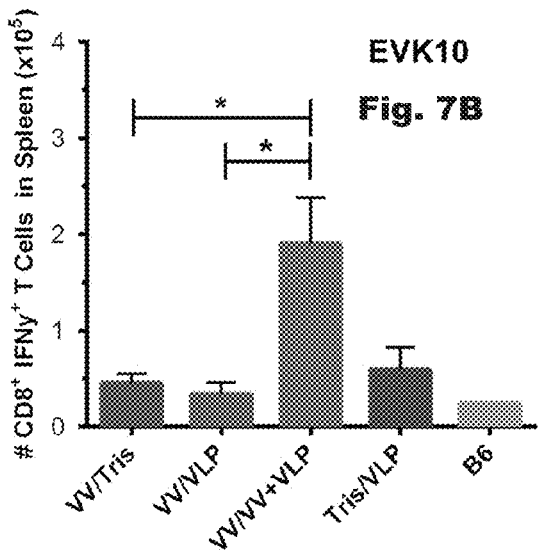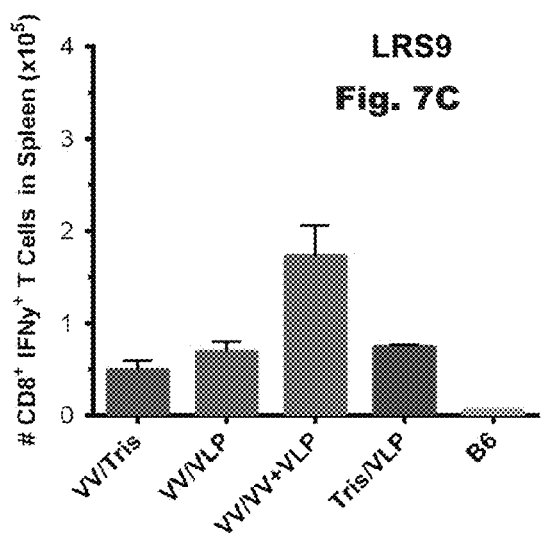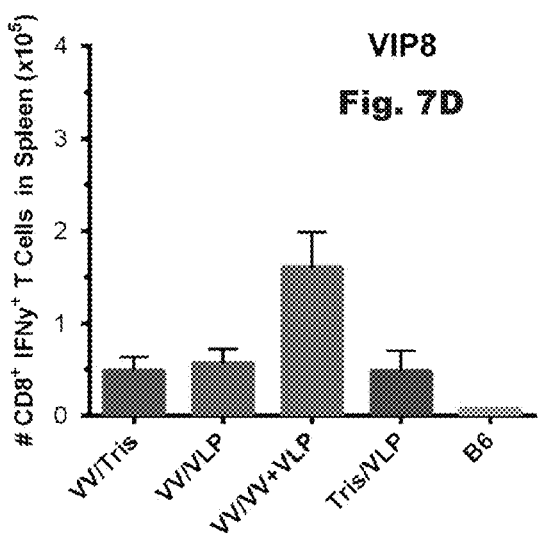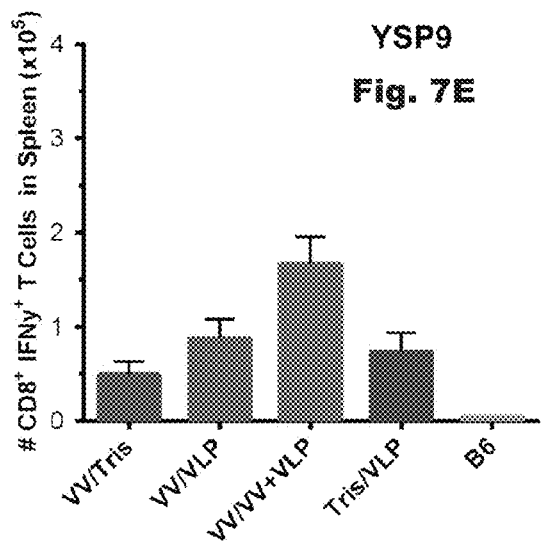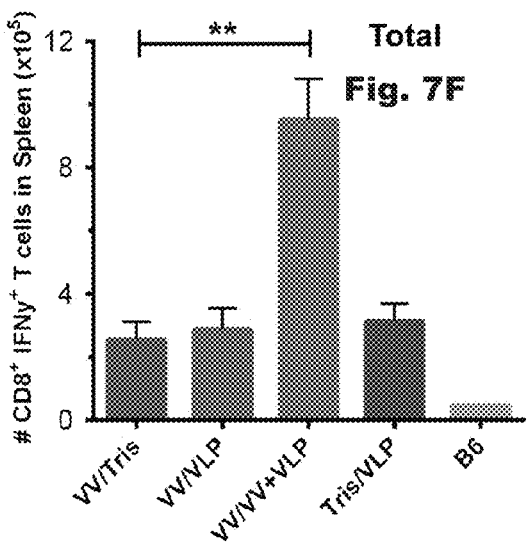

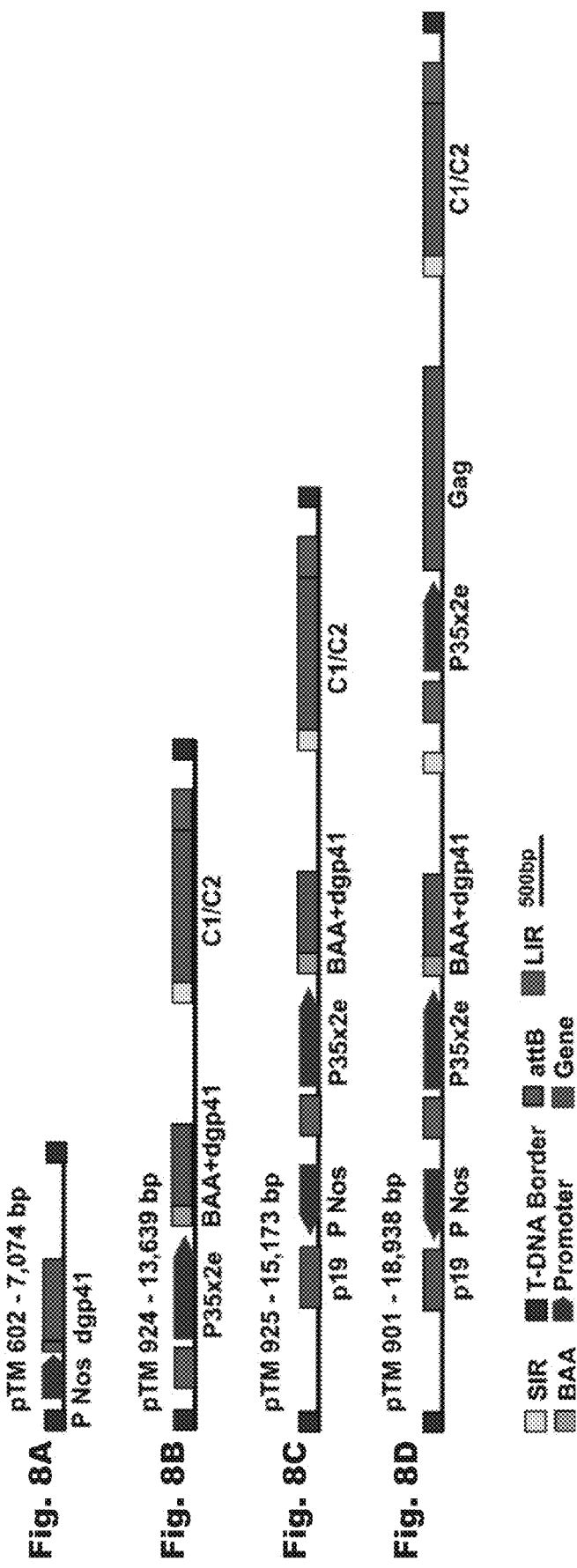

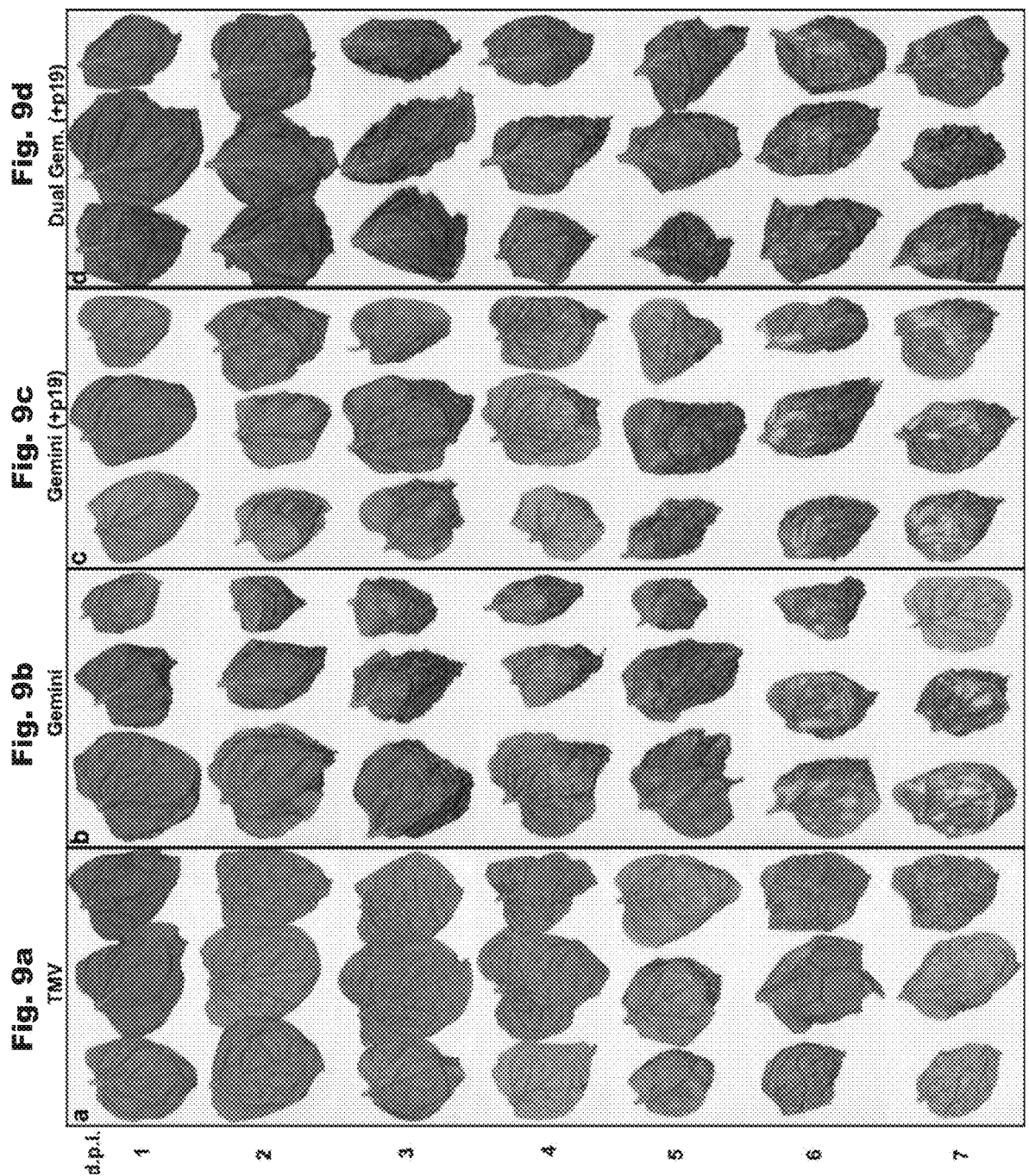

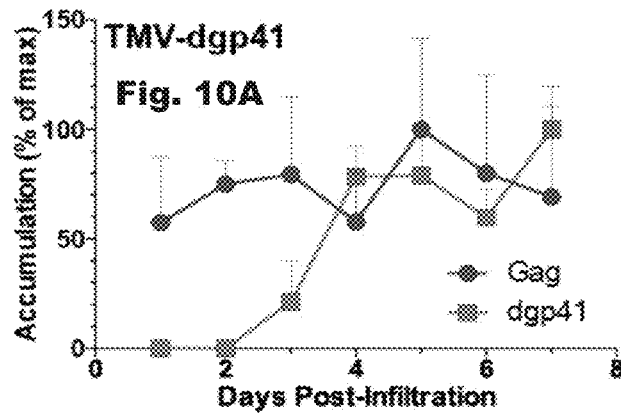
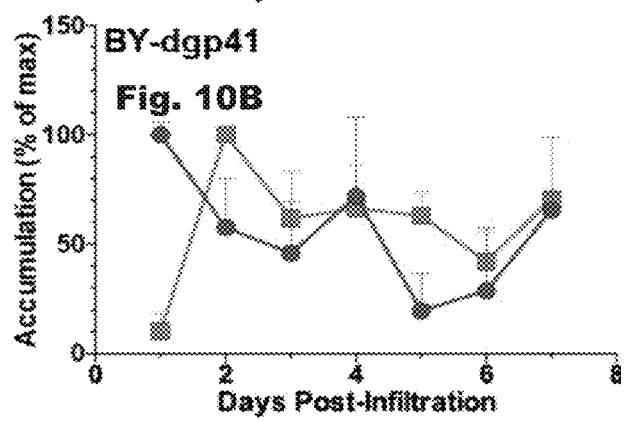
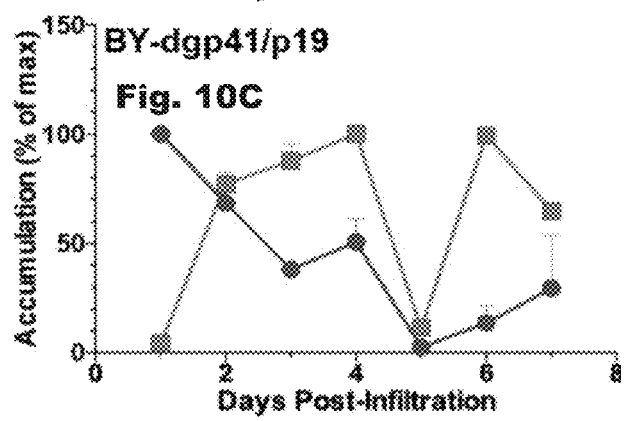
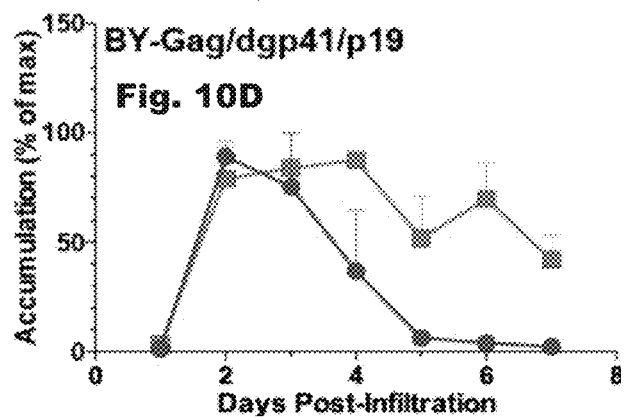
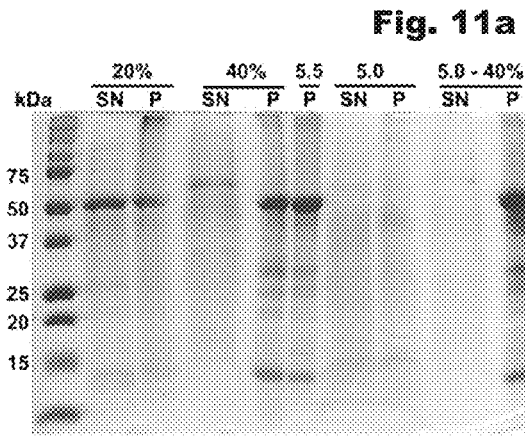
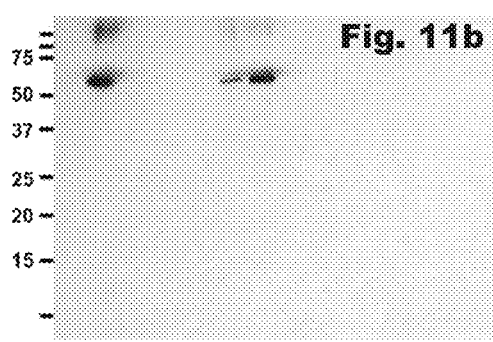
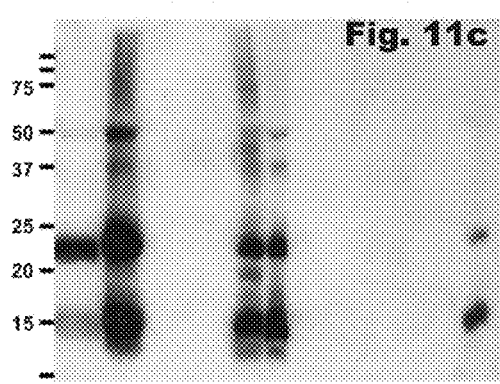

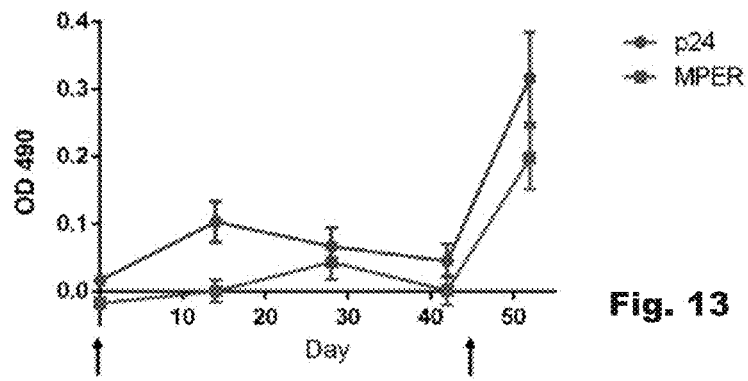
Fig. 13
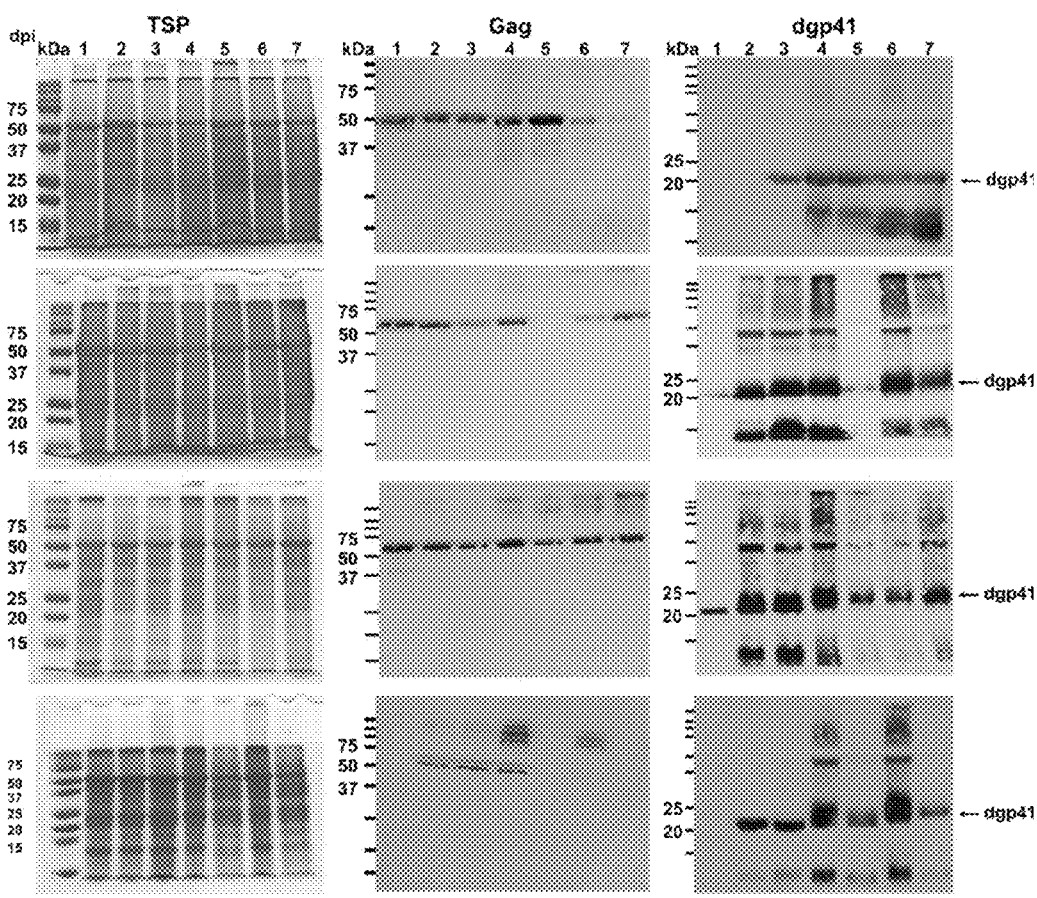
Fig. 14a
Fig. 14b
Fig. 14c
Fig. 14d

HIV VACCINATION COMPOSITIONS COMPRISING VACCINIA VLPS AND PLANT-PRODUCED VLPS PRESENTING HIV ANTIGENS

RELATED APPLICATIONS

This application is a Continuation of U.S. patent application Ser. No. 16/396,676, filed Apr. 27, 2019 (published as US 20190328864), now abandoned, which claims the benefit of and priority to U.S. provisional patent application 62/663,391, filed Apr. 27, 2018, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,256 byte ASCII (text) file named "SeqList" created on Apr. 25, 2019.

TECHNICAL FIELD

The disclosure relates to vaccination strategies against human immunodeficiency virus (HIV), including methods of generating an immune response against HIV, vectors, compositions, and vaccination kits for use in the methods of generating an immune response against HIV.

BACKGROUND

Despite the success of antiretroviral treatment, human immunodeficiency virus (HIV) still causes millions of new infections every year, primarily in regions of the world with limited access to healthcare, making the need for a vaccine more apparent every year. To date, even the most successful HIV-1 vaccine clinical trial, the Phase III Thai Trial (also referenced herein as "RV144 Thai Trial" or "Thai Trial") had only modest and short-lived efficacy (Rerks-Ngarm et al., 2009). The Thai Trial used a non-replicating canarypox viral vector (ALVAC) carrying recombinant genes for Gag, Pol and the surface subunit of the envelope (ENV) protein (gp120) followed by an AIDSVAX protein boost consisting of recombinant gp120 B/E produced in Chinese hamster ovary (CHO) cells. While ALVAC and AIDSVAX showed no protection when tested individually, their combination in RV144 has been shown to be modestly protective, providing valuable information on immune protection correlates. The most direct immune protection correlates pertain to antibody (Ab) responses against the V1-V2 loop of gp120. From these studies the importance of polyfunctional, non-neutralizing Abs (Haynes et al., 2012; Yates et al., 2014; Chung et al., 2014; Liao et al., 2013) has been shown. This short-lived humoral response faded over time and did not provide long-lasting protective advantage over the placebo arm (Yates et al., 2014). The results of the RV144 trial indicated the strength of a prime-boost approach integrating on a live vector with a subunit protein vaccine. The modest efficacy of the trial, however, also suggests that the particular combination of the specific antigens requires further study (Haynes et al., 2012; Yates et al., 2014; Corey et al., 2015; McMichael and Koff, 2014; Prentice et al., 2015). Accordingly, there is a significant need for new vaccination strategies against HIV.

SUMMARY

The disclosure relates to the immunogenicity of virus-like particles (VLPs) produced by a replicating but highly attenuated vaccinia virus vector, a tobacco mosaic virus-based vector, a geminivirus-based vector, or combinations thereof. In certain embodiments, the disclosure is directed to composition comprising a vaccinia VLP and a plant-produced HIV VLP in sufficient amounts to generate an immune response in a mammalian subject against human immunodeficiency virus (HIV). The tobacco mosaic virus-based vector or the geminivirus-based vector expresses Gag, a fragment of gp41, or Gag and a fragment of gp41. In some aspects, geminivirus-based vector further comprises p19. The replicating but highly attenuated vaccinia virus vector expresses Gag, or a fragment of gp41 in certain embodiments, and may be based on NYVAC-KC. In some aspects, the fragment of gp41 is a membrane anchored truncated gp41 presenting the membrane proximal external region with its conserved broadly neutralizing epitopes in the perfusion conformation.

Exemplary embodiments also include a replicating but highly attenuated vaccinia virus vector expressing Gag or a fragment of gp41 and a tobacco mosaic virus-based vector or a geminivirus-based vector expressing Gag, a fragment of gp41, or Gag and a fragment of gp41 are disclosed along with VLPs produced from these vectors. The VLPs produced from the replicating but highly attenuated vaccinia virus vector are a vaccinia VLP presenting Gag, a fragment of gp41, or Gag and a fragment of gp41. The VLPs produced from the tobacco mosaic virus-based vector and the geminivirus-based vector may be plant-produced HIV VLPs presenting Gag and/or a fragment of gp41.

The disclosure is further related to methods of generating an immune response against HIV in a mammalian subject, wherein the subject is administered the vaccinia VLPs or the plant-produced HIV VLP. In some aspects, the methods relate to generating an HIV immune response in a mammalian subject. In some implementations, the mammalian subject is administered the vaccinia VLP and then the mammalian subject is administered the plant-produced HIV VLP at least 30 days later. In some aspects, the administration of the plant-produced HIV VLP is accompanied with administration of the vaccinia VLPs. In some implementations, the subject is administered a combination of the vaccinia VLPs and the plant-produced HIV VLP.

In certain embodiments, the method comprises administering a vaccinia VLP to the mammalian subject, wherein the vaccinia VLP presents HIV Gag and a fragment of gp41; and administering a plant-produced HIV VLP to the mammalian subject, wherein the plant-produced HIV VLP presents HIV Gag and a fragment of gp41 and is isolated from plant tissue transformed with a geminivirus-based plant expression vector. The vaccinia VLP is isolated from a mammalian cell transfected with at least one replicating but highly attenuated vaccinia virus vector and the mammalian subject is administered the vaccinia VLP and the plant-produced HIV VLP in an amount sufficient to generate an HIV immune response in the mammalian subject. In some aspects, the molar ratio of HIV Gag and the fragment of gp41 expressed by the plant produced HIV VLP is 1.7 to 11.8. In certain implementations, the mammalian subject is administered the vaccinia VLP at least 30 days prior to the administration of the plant-produced HIV VLP. In a particular implementation, the method further comprises administering to the mammalian subject a second dose of the plant-produced HIV VLP.

In some aspects, the geminivirus-based plant expression vector comprises a T-DNA region that comprises a first nucleic acid sequence encoding Gag and a first promoter region upstream of the first nucleic acid sequence encoding Gag; a second nucleic acid sequence encoding a fragment of gp41 and a second promoter upstream of the second nucleic acid sequence encoding a fragment of gp41. In certain embodiments, the T-DNA region of the geminivirus-based vector plant expression vector further comprises a nucleic acid sequence encoding at least one replication gene. In some aspects, the geminivirus-based vector is a bean yellow mosaic virus-based vector, the nucleic acid sequence encoding at least one replication gene that encodes Rep/RepA. The first promoter region and the second promoter region comprise a nucleic acid sequence encoding the cauliflower mosaic virus 35S promoter (P35). The first promoter region and the second promoter region further comprise two translation enhancer binding sites downstream of nucleic acid sequence encoding P35. In a particular implementation, the T-DNA region of the plant expression vector further comprises a pair of long intergenic regions, wherein the pair of long intergenic regions flank a portion of the T-DNA region that does not comprise the nucleic acid sequence encoding the silencing suppressor protein and does comprise the at least one replication gene, the first nucleic acid sequence encoding Gag and the first promoter region upstream of the first nucleic acid sequence encoding Gag; and/or the second nucleic acid sequence encoding a fragment of gp41 and a second promoter upstream of the second nucleic acid sequence encoding a fragment of gp41.

In some embodiments, the T-DNA region of the plant expression vector further comprises a nucleic acid sequence encoding a silencing suppressor protein, wherein the nucleic acid sequence encoding the silencing suppressor protein is upstream of the first nucleic acid sequence encoding Gag and the first promoter region upstream of the first nucleic acid sequence encoding Gag and upstream of the second nucleic acid sequence encoding a fragment of gp41 and a second promoter upstream of the second nucleic acid sequence encoding a fragment of gp41. In yet another embodiments, the T-DNA region of the plant expression vector further comprises a nucleic acid sequence encoding barley α-amylase signal peptide, wherein the nucleic acid sequence encoding barley α-amylase signal peptide is upstream of the second nucleic acid sequence encoding a fragment of gp41 and downstream of the second promoter region.

In some aspects, the at least one replicating but highly attenuated vaccinia virus vector is selected from the group consisting of: a first replicating but highly attenuated vaccinia virus vector comprising a third nucleic acid sequence encoding Gag, a second replicating but highly attenuated vaccinia virus vector comprising a fourth nucleic acid sequence encoding a fragment of gp41, and a third replicating but highly attenuated vaccinia virus vector comprising the third nucleic acid sequence encoding Gag and the fourth nucleic acid sequence encoding fragment of gp41. In some aspects, the replicating but highly attenuated vaccinia virus vector is NYVAC. In certain implementations, the vaccinia VLP administered presents both Gap and dgp41. Thus, the at least one replicating but highly attenuated vaccinia virus vector is a replicating but highly attenuated vaccinia virus vector comprising the third nucleic acid sequence encoding Gag and the fourth nucleic acid sequence encoding fragment of gp41.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1E depict, in accordance with certain embodiments, the generation of recombinant vaccinia viruses. Plasmids were cloned to contain either full-length HIV-1 Gag (FIG. 1A) or deconstructed-gp41 (FIG. 1B) as pTM 815 and 816, respectively. The genes are located between homologous recombination arms for the vaccinia virus (VACV) thymidine kinase (TK) locus under the control of a synthetic early/late (E/L) promoter. Also included is the neomycin resistance gene fused to GFP (GFP-neoR). (C and D) SDS-PAGE shows full-length Gag (FIG. 1C) or dgp41 (FIG. 1D) expression in BSC-40's of NYVAC-KC-Gag (Lane 2) and dgp41 (Lane 3) from the final P2 virus stock used in animal experiments. Parental NYVAC-KC shows no expression of either protein (Lane 1). FIG. 1E shoes the SDS-PAGE of ammonium sulfate precipitations from media of BSC-40 cells infected with: NYVAC-KC (WT, Lane 1), Gag (Lane 2), dgp41 (Lane 3), or a co-infection of Gag/dgp41 viruses (G/d, Lane 4). Samples were tested for both Gag (top) and dgp41 (bottom) expression.

FIGS. 2A-2D depict, in accordance with certain embodiment, electron microscopy of NYVAC-KC infected BSC-40s. BSC-40 cells were infected at an MOI of 5 and harvested 24 hpi and prepared for transmission electron microscopy. Cells were infected with either NYVAC-KC (FIG. 2A), NYVAC-KC-Gag (B), NYVAC-KC-dgp41 (FIG. 2C), or a co-infection with an MOI of 5 for each NYVAC-KC-Gag and NYVAC-KC-dgp41 (FIG. 2D). All stages of VACV replication are present: mature virions (white arrow), immature virions (black triangle), immature virions with genome incorporated (white triangle), crescent formation (black arrow), and 'unfilled/empty' virions (FIG. 2E). Budding HIV-1 Gag VLPs (black star) are also seen in those cells infected with NYVAC-KC-Gag. In certain infections, an accumulation of cytoplasmic 'junk' (J) is visible. Other cellular features: mitochondria (M), nucleus (N). Scale bar: 500 nm for all images, except (FIG. 2B-2) and (FIG. 2D-2) images are 100 nm for HIV-1 VLPs.

FIGS. 3A-3C depict, in accordance with certain embodiments, a mouse immunization schedule. FIG. 3A shows the time line of treatment. Six-week-old C57BL/6 mice were immunized at day 0, 45, and 90 with different combinations of recombinant vaccinia virus (represented as an image of a green-enveloped particle) and plant-produced HIV-1 VLPs (represented as an image of a poxvirus). Vaccinia virus doses (VV) consisted of $1\times10^6$ pfu of equally mixed NYVAC-KC-Gag and NYVAC-KC-dgp41 delivered i.m., while plant-produced VLPs were mixed with Ribi adjuvant and delivered i.p. with 2 μg p24 and 1.2 μg MPER. Serum, fecal, and vaginal lavage samples were collected once every 2 weeks (indicated by arrows). Serum samples were analyzed for antigen-specific IgG to p24 Gag (FIG. 3B) or the MPER region of dgp41 (FIG. 3C), shown over the length of the experiment as the ELISA OD 490 nm for the 1:50 dilution (lowest tested).

FIGS. 4A-4C depict, in accordance with certain embodiments, systemic and mucosal antibody production. Endpoint (Day 97) samples were analyzed for serum IgG (FIG. 4A) and mucosal IgA in fecal (FIG. 4B) and vaginal lavage (FIG. 4C) samples. Data are shown for both p24-specific (left) and MPER-specific (right) antibodies. Raw OD 490 nm values are shown for the lowest dilution factor tested (1:50). Statistically significant differences ($p<0.05$) are indicated with an asterisk (*). Each marker represents a single animal.

FIGS. 5A-5C depict, in accordance with certain embodiments, endpoint serum IgG titers and isotyping results. FIG.

5A shows endpoint titers, which were calculated as the reciprocal of the dilution factor that had background level of OD 490 nm (<0.1). Isotypes were determined by ELISA for antigen-specific IgG1 (FIG. 5B) or IgG2a (FIG. 5C) for both p24 (left) and MPER (right) serum IgG. OD 490 nm readings are shown and clearly indicate a bias towards IgG1 production for both groups. Only endpoint (Day 97) serum samples were tested for these two groups because they had the highest responses. (*p<0.05; **p<0.01).

Figure 6:
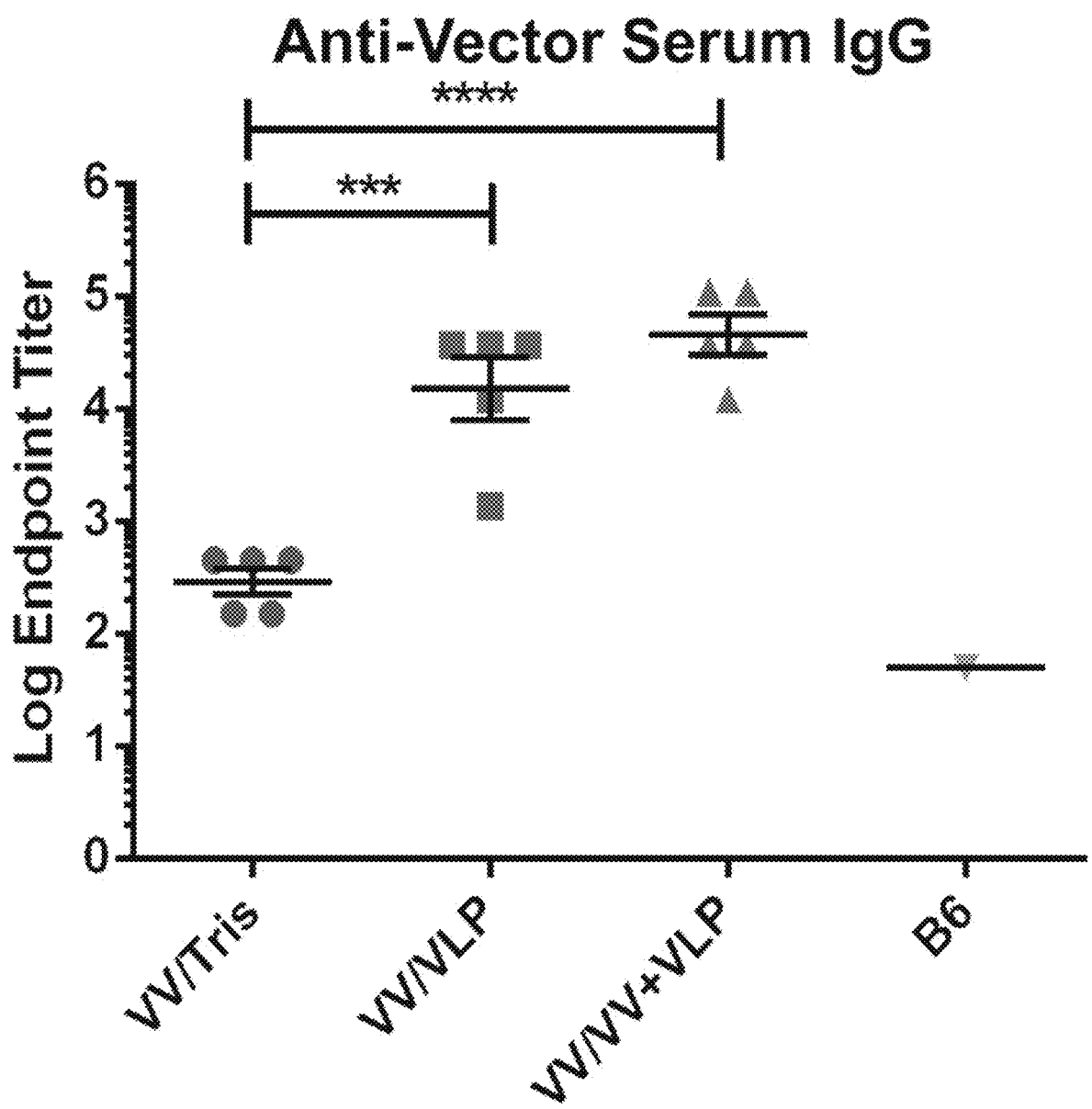

FIG. 6 depicts, in accordance with certain embodiments, anti-VACV responses in serum at endpoint. Day 97 endpoint serum was analyzed by ELISA for anti-vector responses with endpoint titers calculated as for Gag and dgp41-specific serum IgG. The group which received a total of 3 doses of NYVAC-KC vectors shows significantly higher titers of VV-specific antibodies compared with any other group (purple triangles). (*p<0.001; **p<0.0001).

FIGS. 7A-7F depict, in accordance with certain embodiments, depicts Gag-specific CD8 T cell responses. One week after the final immunization, peak CD8 T cell responses were measured by intracellular cytokine staining and flow cytometry for 5 immunodominant ZM96 Gag epitopes: AMQ8 (FIG. 7A), EVK10 (FIG. 7B), LRS8 (FIG. 7C), VIP8 (FIG. 7D), and YSP8 (FIG. 7E). Number of IFN-γ$^+$ CD8$^+$ T cells in the spleen is shown for each peptide individually and the total response in the spleen (FIG. 7F) was calculated by adding the individual responses together for each group. The group boosted with VV and VLPs (purple) was significantly higher than the VV/Tris group (red) for two peptides and the overall response. (* p<0.05; ** p<0.01).

FIGS. 8a-8d depicts, in accordance with certain embodiments, the T-DNA regions of tobacco mosaic virus (TMV) and geminivirus-based transient expression vectors. Four transient deconstructed viral expression vectors were compared in this study. FIG. 8a shows a TMV-based vector, pTM 602, that transiently expresses dgp41 after recombining with two other plasmids as part of the ICON expression system (Marillonnet et al., 2004; Kessans et al., 2013). FIGS. 8b-8d show vectors based on the geminivirus bean yellow dwarf virus (BYDV) that express dgp41 in a replicon bordered by LIRs in pTM 924 (FIG. 8b) and simultaneously with the silencing suppressor protein p19 in pTM 925 (FIG. 8c). These vectors contain the barley α-amylase signal peptide 5' of dgp41 for targeting to the secretory pathway which is under control of the cauliflower mosaic virus 35S promoter (P35) followed by 2 translation enhancer binding sites (2e). ICON systems recombine to add the signal peptide in planta and express dgp41 under the control of the Nos promoter. Additionally, the last geminivirus vector contains two replicons separated by an SIR and LIR for simultaneous expression of Gag and dgp41 in addition to p19 in pTM 901 (FIG. 8d). The size of the full plasmid is indicated. For replicon amplification, geminivirus-based systems also contain the viral replication proteins C1 and C2 (Rep and RepA, respectively). SIR—short intergenic region; BAA—barley α-amylase; T-DNA—transfer DNA; P—promoter, LIR—long intergenic region; 2e—2 enhancer binding sites FIGS. 9a-9d depict, in accordance with certain embodiments, observations of leaf necrosis over a seven-day kinetics time course experiment. Four transient expression constructs were analyzed for expression of dgp41 alone in Gag transgenic N. benthamiana (FIG. 9a-9c) or simultaneously transient expression of Gag and dgp41 in WT plants (FIG. 9d). Leaf samples were collected in triplicate over seven days and images scanned to monitor leaf necrosis. For FIG. 9a, the TMV-based vector expressing dgp41 displays onset of necrosis around 5 dpi. Geminivirus-based transient expression of dgp41 in Gag plants displays necrosis more rapidly, around 3 dpi, without the silencing suppressor protein p19 (Gemini) (FIG. 9b) than the Gemini vector which expresses dgp41 and p19 (Gemini +p19) from the same construct and shows onset of necrosis around 4 dpi (FIG. 9c). WT plants infiltrated with the dual-replicon Gemini vector (Dual Gem.+p19) simultaneously express Gag, dgp41, and p19 from the same construct, results in visible necrosis around 4 dpi (FIG. 9d). dpi—days post infiltration; OD—optical density FIGS. 10A-10D depict, in accordance with certain embodiments, the expression kinetics of Gag and dgp41 with TMV and geminivirus-based vectors. Homogenized leaf tissue was analyzed in triplicate for Gag (FIG. 10A) and dgp41 (FIG. 10B) expression by immunoblot over the seven-day time course and percent of peak expression day calculated through band intensity. Stable Gag expression and transient dgp41 expression was assessed for three vectors in Gag transgenic N. benthamiana: TMV, Gemini, and Gemini +p19. A fourth dual-replicon Gemini vector +p19 transiently expresses Gag, dgp41, and p19 simultaneously in wild-type plants. Peak expression day was determined for each vector. dpi—days post infiltration. Each data point represents mean±SEM.

Figure 12A:
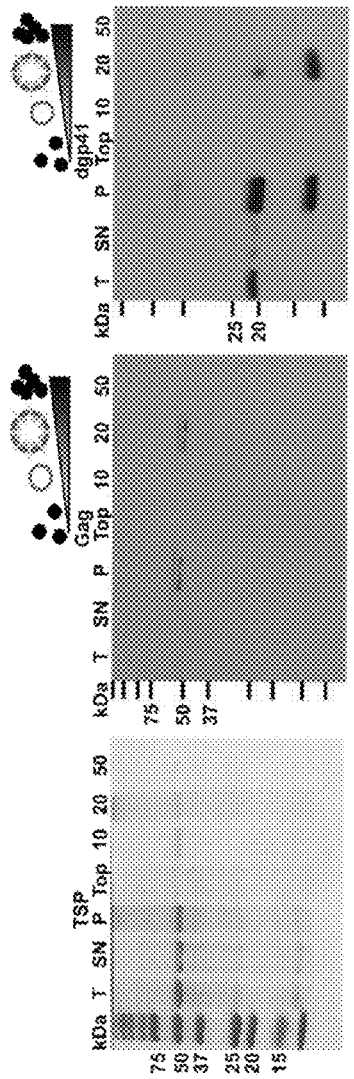
Figure 12B:
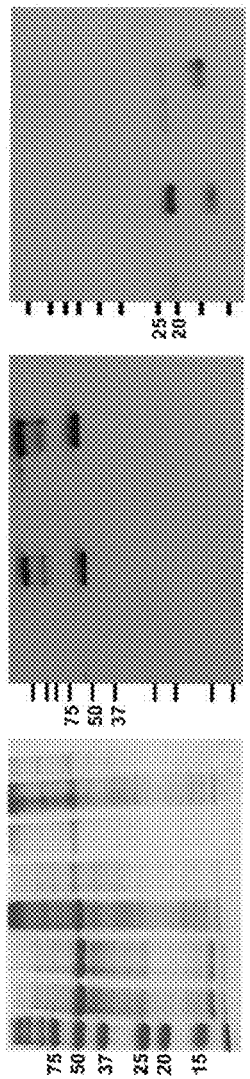
Figure 12C:
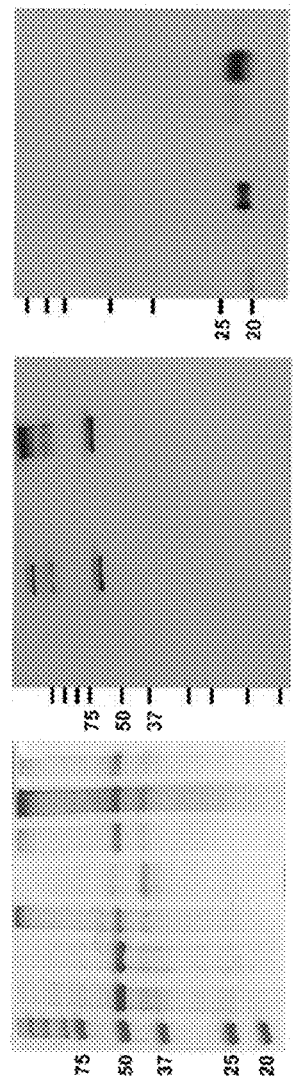
Figure 12D:
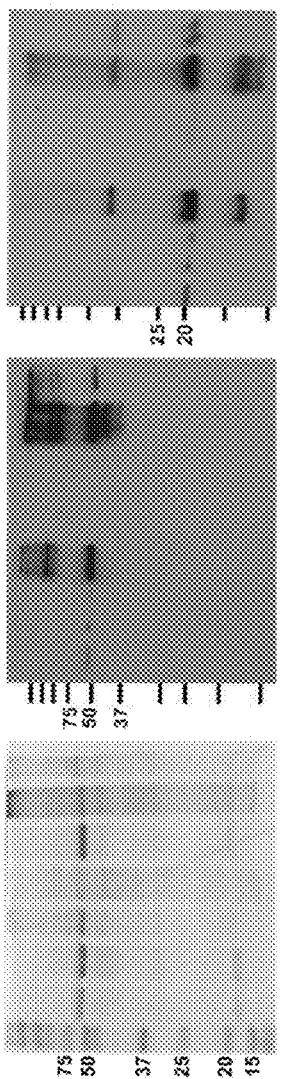

FIGS. 11a-11c depict, in accordance with certain embodiments, optimization of purification technique to minimize rubisco in VLP extractions. Two strategies were tested for efficiency in extracting VLPs with minimal remaining rubisco in each sample. The first strategy utilized sequential ammonium sulfate precipitations at 20% (20% SN and P) and 40% (40% SN and P), where rubisco is expected to pellet around 25%. The second strategy employed pH changes to pH 5.5 (5.5 P) followed by pH 5.0 (5.0 SN and P) where rubisco is expected to pellet at pH 5.5. An additional 40% ammonium sulfate precipitation was performed on the pH 5.0 SN to pellet any remaining VLPs (5.0-40% SN and P). Lanes were loaded with equivalent TSP as shown by Coomassie staining (FIG. 11a). Expression of Gag (FIG. 11b) and dgp41 (FIG. 11c) in each fraction was analyzed by immunoblot. SN—supernatant; P—pellet; TSP—total soluble protein FIGS. 12a-12d depict, in accordance with certain embodiments, purification of HIV VLPs for TMV and geminivirus-based vectors. Six-week-old N. benthamiana Gag transgenic plants were infiltrated to transiently express dgp41 with TMV (FIG. 12a), Gemini (FIG. 12b), or Gemini +p19 (FIG. 12c). In FIG. 12d, WT plants were infiltrated with a dual-replicon Gemini +p19 to transiently express Gag and dgp41. Leaf tissue was harvested on peak expression day and VLPs were extracted in 20 g batches (T—total extract) through 20% ammonium sulfate precipitation (SN—20% ammonium sulfate supernatant; P—pellet) and density gradient centrifugation with step-wise 10-20-50% iodixanol layers (Top—sample after centrifugation; 10% iodixanol; 20% iodixanol; 50% iodixanol). 5 μg total soluble protein (TSP), as determined by Bradford assay, was loaded into each lane and analyzed by Coomassie staining (left), and for Gag (middle) and dgp41 (right) expression. VLPs are almost completely pelleted with 20% ammonium sulfate with little to no detectable protein remaining in the SN and isolate to the 20/50% barrier of the density gradient. Purifications representative of three independent extractions for each vector are shown.

FIG. 13 show, in accordance with certain embodiments, VLP-induced Gag and dgp41-specific serum IgG levels over the course of 52 days. C57BL/6 mice were injected i.p. at Day 0 and Day 45 with VLPs, indicated by arrows. Anti-p24 (Gag) and anti-MPER (dgp41) serum IgG is shown over time as the ELISA OD 490 nm for the 1:50 dilution. At the Day 52 endpoint, all animals have detectable levels of both Gag and dgp41 specific antibodies.

FIGS. 14a-14d depict, in accordance with certain embodiments, the expression of Gag and dgp41 with TMV and geminivirus-based vectors. Leaf samples pictured in FIGS. 9a-9d were homogenized for each vector, and 20 µg TSP was loaded in each lane (dpi 1-7), as measured by Bradford assay. Three vectors were compared for dgp41 expression in Gag transgenic *N. benthamiana*: (FIG. 14a) TMV, (FIG. 14b) Gemini, and (FIG. 14c) Gemini +p19. A fourth dual replicon Gemini vector +p19 transiently expresses Gag, dgp41, and p19 simultaneously in WT plants (FIG. 14d). Coomassie-stained gels show equal TSP across lanes (left) and specific immunoblot for Gag (middle) and dgp41 (right) proteins was used to determine expression levels and identify peak expression day. Images shown are representative of triplicate leaf samples processed for each vector. dpi—days post infiltration; TSP—total soluble protein; WT—wild-type

DETAILED DESCRIPTION

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "virus-like particle" or "VLP" refers to multiple protein structure that mimic the organization and conformation of authentic native viruses but lack the viral genome. In some embodiments, expression of viral structural proteins, for example capsid or envelope proteins, result in the self-assembly of VLPs. In other embodiments, a viral core is required to facilitate the assembly of the VLP when fragments of a protein are the desired presentation targets at the surface of the VLP. Viral cores used in the design of VLPs include bacteriophage MS2, adeno-associated virus, adenovirus, and tobacco mosaic virus.

As referenced herein, the nucleic acid sequence of Gag has at least 95% identity with the nucleic acid sequence of Accession No. AY805330 or Accession No. JX534517.

As used herein, the term "dgp41" refers to a membrane anchored truncated gp41 presenting the membrane proximal external region with its conserved broadly neutralizing epitopes in the prefusion conformation. As referenced herein, the nucleic acid sequence of dgp41 has at least 95% identity with the nucleic acid sequence of Accession No. AF075722, Accession No. AY805330, or Accession No. JX534518.

The disclosure relates to a vaccination strategy against human immunodeficiency virus (HIV) using VLPs presenting Gag and/or dgp41. VLPs are safe, yet immunogenic, components of several vaccines and candidate vaccines for multiple infectious diseases (for a review see Kushnir et al., 2012). The potential for success of VLP-based vaccines is indicated by the widespread use of the human papillomavirus (HPV) vaccines Gardasil® (Merck and Co, 2006) and Cervarix® (GlaxoSmithKline, 2014). To date, many plant-produced vaccines have been tested in animal studies for immunogenicity for both human and veterinary diseases (Rybicki, 2010; Scotti and Rybicki, 2013). Additionally, VLPs, but not soluble subunit vaccines, are more likely to properly induce innate and low affinity B cells to transport and display antigen to induce Ab responses (Bessa et al., 2012; Link et al., 2012).

In some aspects, the disclosure is directed to a replicating but highly attenuated vaccinia virus for expressing Gag and/or dgp41. Upon infection of mammalian cells with the vaccinia virus, VLPs presenting Gag and/or dgp41 are produced. In other aspects, the disclosure is directed to a HIV VLP produced from a tobacco mosaic virus-based vector (magnICON) or a geminivirus-based vector. The tobacco mosaic virus-based vector and geminivirus-based vector are designed for expression of the HIV VLP in plants. Accordingly, the disclosure also relates to optimized methods of purifying the HIV VLP from plants to reduce the amount of protein contaminants, for example rubisco (Ribulose-1,5-bisphosphate carboxylase/oxygenase). The disclosure is also encompasses vector compositions for producing vaccinia VLPs and plant-produced HIV VLPs that generate an immune response against HIV in a mammalian subject, particularly HIV-1.

In other aspects, the disclosure is directed to methods of generating an immune response against HIV, particularly HIV-1, in a mammalian subject using the VLPs described herein.

In some implementations, the methods of generating an immune response against HIV in a mammalian subject comprises administering the VLP described herein to the mammalian subject on two separate occasions, for example, at least 30 days apart. In certain implementations, the two administrations of the VLP are 45 days apart. In one implementation, the VLP administered in both instances are plant-produced HIV VLPs. Plant-produced HIV VLPs are immunogenic in mice and can elicit antibodies specific to the MPER broadly neutralizing antibody (bnAb) target in the dgp41 protein (FIG. 13). In one aspect, two weeks after the first dose of Gag/dgp41 VLPs produced using the TMV-based vector was administered to murine subjects, p24-specific IgG as detectable in the serum while MPER-specific antibodies were below detection limit (FIG. 6). One week after the second immunization, a 100% response rate was observed for both p24- and MPER-specific serum IgG.

In a particular embodiment, the method of generating an immune response against HIV in a mammalian subject comprising exposing the mammalian subject to a VLP presenting Gag and/or a fragment of gp41 (for example, dgp41) on three separate occasions, wherein each exposure is at least 30 days apart, for example 45 days apart. In some aspects, the first exposure comprises administration of attenuated vaccinia virus expressing Gag and/or dgp41 to the mammalian subject, which results in exposure to vaccinia VLPs presenting Gag and/or dgp41, while the second exposure and third exposure comprise administration of a plant-produced HIV VLP to the mammalian subject. In some implementations, an adjuvant is administered with the plant-produced HIV VLP. In certain embodiments, the HIV VLPs administered in the second and third exposure are produced from a plant transformed with a tobacco mosaic virus-based vector (magnICON) or a geminivirus-based vector expressing Gag and/or dgp41. In particular implementations, the second exposure and third exposure further comprise administration of attenuated vaccinia virus expressing Gag and/or dgp41. In certain implementations, the amount of plant-produced HIV VLP administered to a mammalian subject per exposure that sufficient to ultimately generate an HIV immune response in the mammalian subject is between 1.5 and 3 µg Gag (p24) and between 0.75 and 2.5 µg dpg41 (MPER), between 1.75 and 2.25 µg Gag and between 0.95 and 1.45 µg dpg41, or preferably about 2 µg Gag and about 1.2 µg dpg41. In some aspects, the molar ratio of dpg41 to Gag is at least 1.7 or between 1.7-11.8. In some aspects, the total amount of Gag and dpg41 administered per exposure is between 60 and 400 µg for each antigen, between 100 and 350 µg for each antigen, between 150 and 300 µg for each antigen, between 250 and 250 µg for each antigen, or preferably 300 µg for each antigen. Thus, in some aspects, the disclosure relates to a composition comprising a plant-produced HIV VLPs and vaccinia VLP.

This vaccine strategy is based on two discoveries. The first is that replicating vectors, in addition to their excellent facility in eliciting T cell responses, are expected to increase antigen load, resulting in improved immunogenicity. The second is that VLPs improve presentation of relevant neutralizing determinants to the immune system. In particular, the inventors developed replicating vaccinia virus vectors based on NYVAC-KC that express Gag and dgp41 of HIV-1 as matching antigens to the plant-produced VLPs for prime/boosting purposes. The HIV membrane protein gp41 contains the bnAb target known as the MPER. This region requires the context of a membrane in order to elicit the partially auto-reactive bnAbs found in HIV-infected patients (Verkoczy et al., 2010, 2013; Haynes et al., 2005; Zhang et al., 2016). In some implementations, the method further comprises administering to the subject a plant-produced HIV VLP. Accordingly, in some embodiments, the methods comprise administering together the combination of NYVAC-KC-Gag/dgp41 replicating vaccinia virus vectors in a regimen closely mimicking the RV144 clinical trial.

Figure 3A:
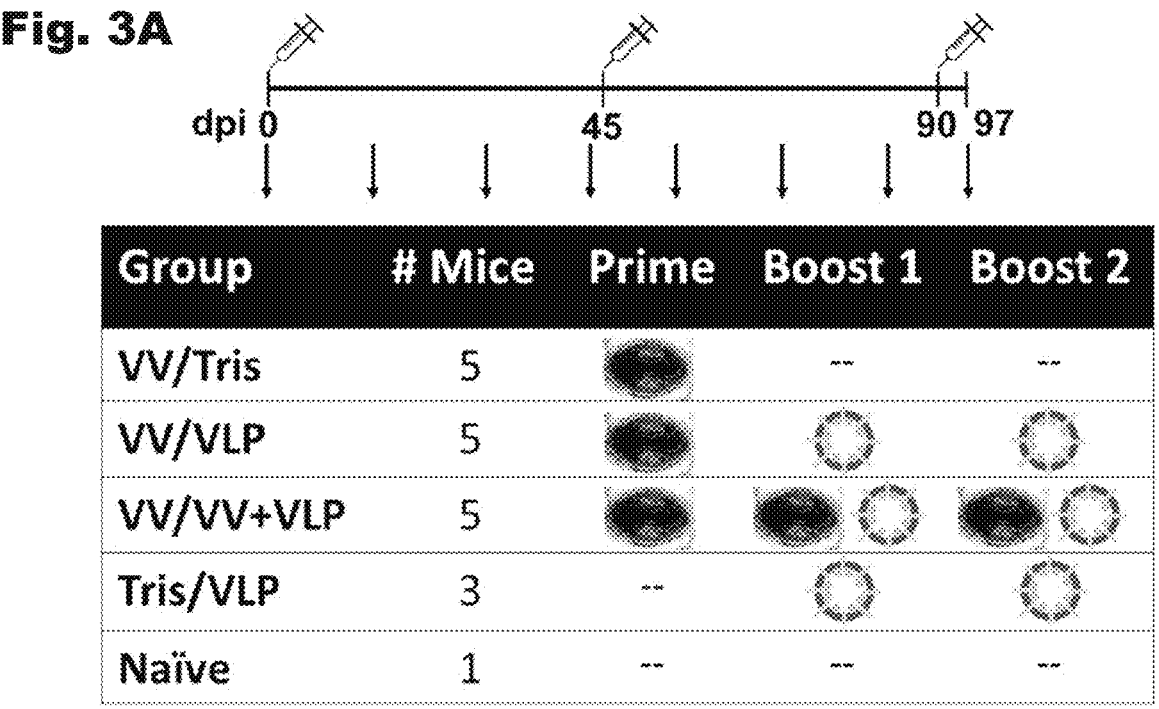
Figure 3B:
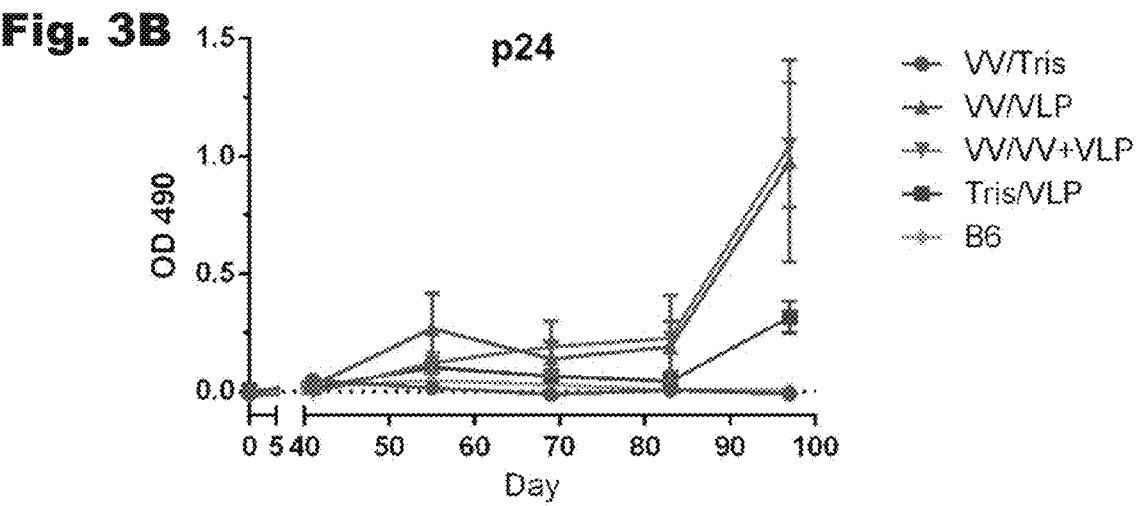
Figure 3C:
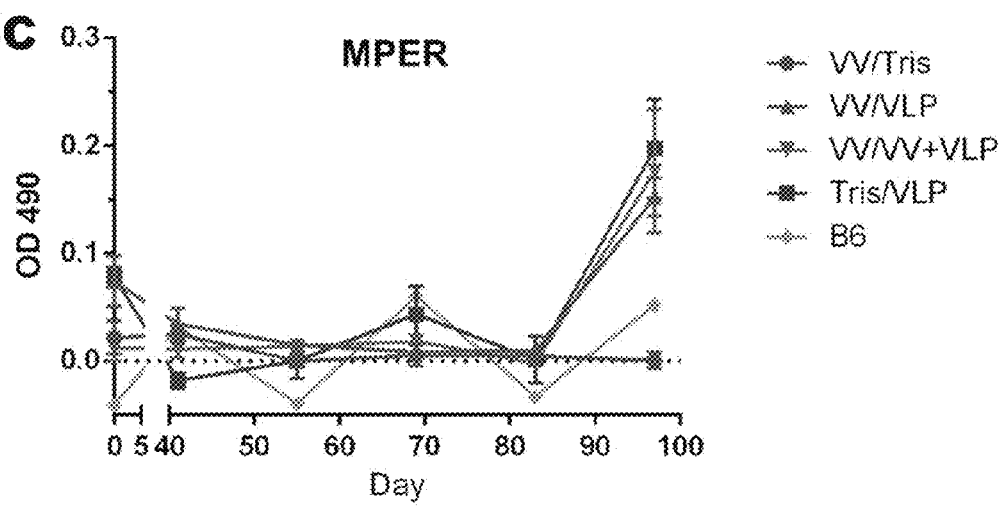
Figure 5A:
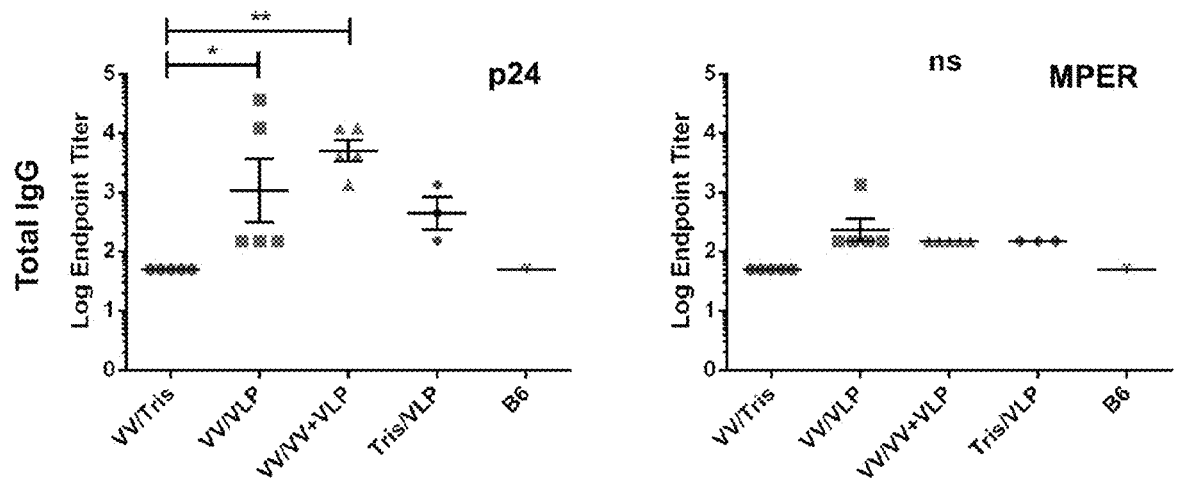
Figure 5B:
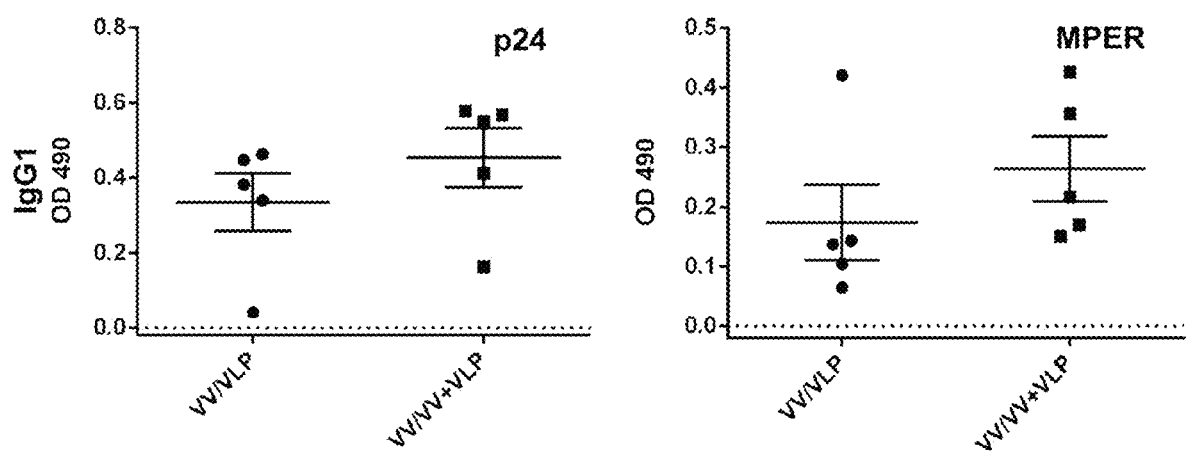
Figure 5C:
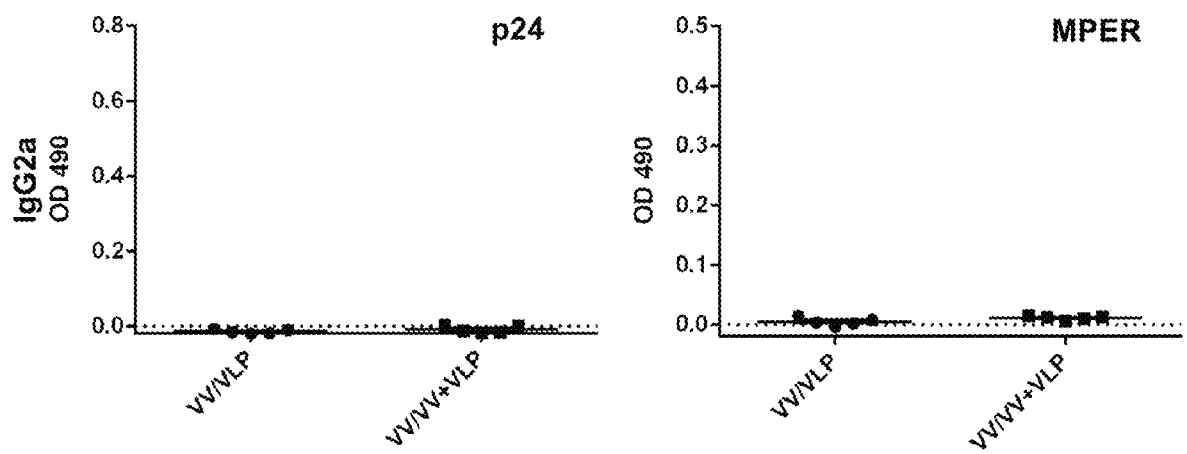

Despite the poor priming capacity of the vaccinia VLP (VV) in terms of eliciting antibody responses against Gag and gp41, upon boosting with plant-derived HIV VLPs at Day 45, antibody (Ab) production spiked with another increase after the final immunization at Day 97 (FIG. 3B-3C). Endpoint anti-p24 Ab titers reached significant levels for serum IgG in the group boosted with just VLPs (Group 2) or the combination of VV+VLPs (Group 3) (FIG. 5A), and all groups boosted with any combination of VV and VLPs (Groups 2-4) reached significance for MPER-specific serum IgG (FIG. 4A). As noted above, due to the lack of detectable Abs prior to boosting with VLPs, it seems that the plant-produced VLPs administered at a relatively low dose, are largely responsible for boosting the Ab responses following sub-responsive priming. In the groups with the highest responses, these antibodies were shown to be entirely IgG1 with no detectable IgG2a (FIG. 5B-5C). The inventors also discovered that plant-produced HIV VLPs stimulate a predominant Th2 response through activation of M2b macrophages, thus stimulating strong B cell Ab production.

In some aspects, the method induces systemic and mucosal antibody responses to Gag and dgp41 with a bias towards IgG1. For example, the methods of generating an immune response against HIV in a mammalian subject produce robust Gag-specific CD8 T cell responses. Gag-specific CD8 T cell responses were highest in the group boosted with VV+VLPs (Group 3), reaching 12.7% of CD8 T cells expressing IFN-γ in response to the five Gag peptides (FIG. 7). While inventors do not have a non-replicating vector in this study, these responses are higher than MVA-induced Gag-specific CD8 T cells (<0.5%) in humans after two doses (Keefer et al., 2011). Additionally, results here show higher Gag-specific CD8 T cell responses than seen in mice after DNA-NYVAC or DNA-MVA prime-boost regimen which elicit <2% GPN/Env-specific CD8 T cells (<0.5% Gag specific) and 12-15% GPN/Env-specific CD8 T cells (5.5% Gag-specific), respectively (Gomez et al., 2012b; Garcia-Arriaza et al., 2013). Thus, replication plays a role in increasing T cell responses. Results from NYVAC HIV vaccines have shown proficiency for eliciting polyfunctional T cell responses (i.e. antigen-specific T cells expressing multiple cytokines) which are primarily effector memory T cells (Harari et al., 2008, 2012; Gomez et al., 2012b; Garcia-Arriaza et al., 2011). Accordingly, replicating vectors such as NYVAC-KC, may have additional beneficial roles in the prevention of HIV infection due to the association of polyfunctional T cells in the periphery (Betts et al., 2006). Additionally, it is important to note than when Env is included in the MVA or NYVAC vector, T cell responses are skewed to be primarily Env-specific with minimal Gag recognition (Harari et al., 2008, 2012; Gomez et al., 2012b; Garcia-Arriaza et al., 2013; Garcia et al., 2011; Mooij et al., 2009). Env-specific cytotoxic T lymphocyte (CTL) responses were not protective in clinical trials nor correlated with improved disease in natural infection (McMichael and Koff, 2014), while Gag-specific responses have been correlated with improved CD4 count and reduced viral load (Kiepiela et al., 2007; Koup et al., 1994; Stephenson et al., 2012; Jiao et al., 2006; Ogg et al., 1998; Brander and Walker, 1999) and have epitopes which are less prone to CTL escape (Goulder and Watkins, 2004).

As shown in the animal study of Example 1, the described VLPs produced from the vaccinia virus vector and the plant-produced HIV VLPs work in concert to elicit Gag-specific CD8 T cell responses and both systemic and mucosal antibodies to Gag and dgp41 peptides in the immunization group which most closely mimics the Thai Trial. The vaccina virus vector is developed from the NYVAC strain previously rendered replication incompetent in human cells by deletion of 18 open reading frames from the genome of Copenhagen (Cop), its parental strain (Tartaglia et al., 1992a). NYVAC-KC contains a reinsertion of two host-range genes, K1L and C7L, which allows the virus to replicate in human tissue, thus improving immunogenicity while remaining highly attenuated (Kibler et al., 2011; Quakkelaar et al., 2011).

1. Gag

Because of the surface exposure, immunogenicity, and the critical roles during target-cell infection of HIV envelope protein (Env/gp120), this protein has been a natural target for vaccine development since the early days of HIV-1 research (Burton and Mascola, 2015; Mascola and Haynes, 2013). However, targeting gp120 in the development of an HIV vaccine has proven to be far from straightforward. gp120 is not highly conserved, and many critical neutralization targets are hidden or are only exposed upon conformational change during viral entry, thus limiting the effectiveness of any NAb response to this antigen (Pancera et al., 2014; Decker et al., 2005; Labrijn et al., 2003). Thus, gp120 functions as a highly mutable decoy with most of its functionally important immunogenic sites conformationally occluded or shielded by glycans. In fact, monomeric preparations of gp120, as well as various preparations aimed at presentation of gp120 trimers, have repeatedly failed to induce protective immune responses in animal models or humans, with the sole and modest exception of the RV144 Thai Trial (also referenced herein as "Thai Trial") (McGuire et al., 2014; Jacob et al., 2015; Moore et al., 2015; Haynes et al., 2016).

The Thai Trial demonstrated the strength of prime/boost vaccination approach by effectively combining two components that were previously shown to be ineffective on their own: a live (albeit non-replicating) canarypox viral vector (ALVAC) and a soluble protein boost (AIDSVAX). The low efficacy of the trial left much to be desired for widespread use as a vaccine while providing the conceptual basis for further improvement (Rerks-Ngarm et al., 2009). Protein engineering has attempted to resolve many of the issues of targeting gp120, including the design of SOSIP trimeric gp140 variants of Env to make a more structurally accurate target necessary for eliciting specific types of NAbs, including a design to specifically target nAb germline B cells (Jardine et al., 2013; Billington et al., 2007; Du et al., 2009; Sellhorn et al., 2012; Wan et al., 2009). To date, no successful clinical trials incorporating an engineered gp140 antigen have been conducted.

An optimized nucleic acid sequence encoding Gag for VLP formation was previously described (Kessans et al., 2013). As described herein, the optimized Gag sequence is suitable for VLP formation using a vaccinia virus vector, tobacco mosaic virus-based vector, and geminivirus-based vector. In some aspects, the nucleic acid sequence of the optimized Gag comprises the nucleic acid sequence of Accession No. JX534517. In other aspects, the nucleic acid sequence of the optimized Gag has at least 95% identity with the nucleic acid sequence of Accession No. JX534517. In some embodiments, the 2. gp41

Whereas many studies have examined the immunogenicity of Gag, far fewer studies have examined gp41. The gp41 protein of HIV is the transmembrane portion of the HIV surface spike and contains the highly immunogenic membrane proximal external region (MPER), a target of many broadly neutralizing antibodies (bnAbs) (Purtscher et al., 1994; Zwick et al., 2001; Huang et al., 2012). gp41 contains highly immunogenic determinants that induce production of Abs that are among the first to arise during acute HIV-1 infection but are of very limited protective value, showing little or no antiviral activities (Burton and Mascola, 2015; Liao et al., 2011; Bonsignori et al., 2012). These immunodominant epitopes are located in a region of the protein spanning the two heptad repeat domains and in particular within the loop that connects them (Zolla-Pazner, 2004) and are exposed on the gp41 "stump" in its six-helical bundle conformation upon removal of the gp120 subunit (Burton and Mascola, 2015). Still, gp41 was found to be the target of a number of broadly neutralizing Abs (bnAbs) directed against conformational (35O22 binding at the gp41-gp120 interface) (Huang et al., 2014) and linear epitopes (2F5, 4E10, Z13 and 10E8 that recognize closely situated sites within the membrane proximal external region, MPER) (Parker et al., 2001; Cardoso et al., 2005; Nelson et al., 2007; Huang et al., 2012).

Beyond neutralization, anti-MPER Abs, including the above-mentioned bnAbs, were found to exhibit other potent anti-HIV-1 activities including transcytosis blockade (Tudor et al., 2012; Shen et al., 2010; Matoba et al., 2004, 2008, 2009), Ab-dependent cell-mediated cytotoxicity (ADCC) (Tudor and Bomsel, 2011; Hessell et al., 2007) and curbing of dendritic cell-mediated trans-infection (Tudor et al., 2012; Sagar et al., 2012; Magerus-Chatinet et al., 2007). Moreover, passive immunization with these bnAbs provided impressive protection against mucosal transmission of a simian-HIV hybrid (SHIV) in the macaque model (Baba et al., 2000; Hessell et al., 2010; Klein et al., 2013a). Anti-MPER Abs with anti-viral activities were also described in mucosal secretions of highly-exposed but seronegative individuals (Kaul et al., 1999, 2001; Pastori et al., 2000; Devito et al., 2000a, 2000b; Tudor et al., 2009). Lastly, anti-MPER Abs that were passively passed through breast milk from infected mothers to their uninfected babies were correlated with protection (Diomede et al., 2012; Pollara et al., 2015).

Despite their long-standing promise, anti-MPER bnAbs are naturally rare and are notoriously difficult to elicit. For example, less than 25% of HIV-1-infected patients develop broad and potent nAbs, which even if present require ~2-4 years to produce (Burton and Mascola, 2015; Mascola and Haynes, 2013; Haynes et al., 2016; Mascola and Montefiori, 2010). Several explanations have been suggested, including a lengthy maturation process involving many somatic mutations and extensive affinity maturation (Klein et al., 2013b; Kepler et al., 2014), and clonal deletion of the B-cell lines secreting such bnAbs that were shown to be partially autoreactive (Verkoczy et al., 2010, 2011, 2013). Interestingly, many of the autoreactivity targets are lipids that can be found in both the plasma membrane of the host cell and in the viral envelope (Haynes et al., 2005; Alam et al., 2007, 2009; Irimia et al., 2016).

It is widely accepted that the membrane milieu of the MPER region plays a major role in the functional immunogenicity of gp41 (Alam et al., 2009; Chen et al., 2014). Both the metastable native conformation of the gp120-gp41 trimer and the highly stable post-fusion conformations do not expose the neutralizing epitopes (Frey et al., 2008, 2010; Buzon et al., 2010; Pancera et al., 2014), and fail to efficiently elicit bnAbs (Williams et al., 2015; Sanders et al., 2015; Crooks et al., 2015; Davis et al., 2009; Decker et al., 2005; Labrijn et al., 2003) or engage the germline B cell precursors for specific bnAbs (McGuire et al., 2014; Hoot et al., 2013; Jardine et al., 2013).

An effective MPER-based antigen therefore requires presentation of the MPER within a context of a membrane and exposure of the region in a conformation mimicking the putative prefusion intermediate. In part, this is because many of the apparent interactions between the amphipathic peptide and the membrane affect the ability of the region to interact with bnAbs (Haynes et al., 2005; Verkoczy et al., 2010; Williams et al., 2015; Haynes et al., 2016; Zhang et al., 2016). This antigenic region when presented correctly on a membrane has strong potential as a vaccine component. Displaying the MPER in a virosome successfully elicited mucosal and systemic Abs with transcytosis-blocking activity in a Phase I clinical trial (Leroux-Roels et al., 2013). Bomsel and co-workers used a gp41 peptide (residues 649-684) spanning the MPER and part of the C-terminal heptad repeat to decorate liposomes ("virosome"), and the virosome elicited protective responses against SHIV infection in the macaque model (Bomsel et al., 2011). VLPs displaying gp41 can elicit both systemic and mucosal Abs to this region (Kessans et al., 2016) and transcytosis blocking Abs to this region are achievable (Matoba et al., 2008).

As described herein, a fragment of gp41 that comprises a membrane anchored truncated gp41 presenting the membrane proximal external region with its conserved broadly neutralizing epitopes in the prefusion conformation is suitable for triggering an immune response against HIV. In some aspects, the fragment of gp41 is dgp41. In certain embodiments, the nucleic acid sequence of dgp41 comprises the nucleic acid sequence of Accession No. JX534518. In other embodiments, the nucleic acid sequence of dgp41 has at least 95% identity with the nucleic acid sequence of Accession No. JX534518. In some aspects, the nucleic acid sequence of dgp41 is the nucleic sequence of the digestion fragment pTM 602 using the restriction enzymes NcoI and SacI.

3. Vaccinia VLP

Live recombinant vectors based on viruses belonging to a wide range of families such as adenoviridae, poxviridae, and herpesviridae have been previously tested for their immunogenicity (Rerks-Ngarm et al., 2009; Hansen et al., 2013a; Huang et al., 2015; Buchbinder et al., 2008; Tartaglia et al., 1992b). The relative success of ALVAC within the context of RV144 increased the focus on poxviruses (see Gomez et al., 2012a; Pantaleo et al., 2010; Jacobs et al., 2009). ALVAC is based on canarypox, which like other avipoxviruses is naturally attenuated in humans due to its restricted replication in non-avian cells (Taylor and Paoletti, 1988; Taylor et al., 1988) accounting for ALVAC's high safety profile (Team AVEGP, 2001; Nitayaphan et al., 2004). Similarly, when developing vaccinia-based vaccine vectors, efforts were initially focused on strains that are non-replicating in human cells (e.g. MVA and NYVAC), due to safety concerns over potential complications with VACV infection in immune-compromised individuals.

Live viral vectors are appealing as vaccine vehicles for the expression of HIV-1 antigens due to their proficiency for eliciting T cell responses. For example, a cytomegalovirus (CMV) vector was recently shown in nonhuman primates to clear an established SIV infection with dependency on CD8 T cells recognizing non-canonical epitopes on major histocompatibility complex (MHC) II instead of MHC I (Hansen et al., 2013a, 2013b). Poxviruses also stand out amongst other viral vectors [see reviews (Gomez et al., 2012a; Pantaleo et al., 2010; Jacobs et al., 2009)] as attested by the Thai Trial that employed a canarypox-based vector and was the first and only HIV-1 vaccine clinical trial to show efficacy (Rerks-Ngarm et al., 2009; Haynes et al., 2012). The canarypox-based viral vector used in the trial, ALVAC, is not capable of replication in mammalian cells (Taylor and Paoletti, 1988; Taylor et al., 1988). Inability to replicate in vivo in humans makes the virus safer to use as a vaccine or a vaccine vector. However, as described herein, replication could enhance immunogenicity by increasing antigen load as the virus replicates in vivo.

Intensive research led to partial uncoupling of attenuation and replication in NYVAC-based vectors showing enhanced immunogenicity without compromising their safety. Specifically, reinsertion of two host-range genes yielded NYVAC-KC. This strain is capable of replicating in human cells and displays enhanced immune activation, yet it remains highly attenuated in a mouse model of pathogenesis (Kibler et al., 2011; Quakkelaar et al., 2011), thus giving this particular vector many desirable traits of a vaccine vector and was chosen for use in the work presented here. NYVAC was originally designed as a highly attenuated vaccine vector by specifically deleting 18 open reading frames from its parental strain (Cop), thus preventing its replication in humans (Tartaglia et al., 1992b). NYVAC has been tested as an HIV vaccine vector and was shown to induce robust, polyfunctional CD4 and CD8 T cell responses to Env and Gag-Pol-Nef (GPN) antigens in vaccinated individuals (Harari et al., 2008, 2012). Because mucosal immune responses are thought to be particularly important in protection against HIV-1, it was significant to note that such responses could be detected in the gut of NYVAC-immunized patients (Perreau et al., 2011). More recently, intensive research led to partial uncoupling of attenuation and replication in NYVAC-based vectors showing enhanced immunogenicity without compromising their safety. Specifically, reinsertion of two host-range genes yielded NYVAC-KC. The NYVAC-KC vector is a replicating, but safe, live viral vector with which induces higher Gag-specific CD8 T cell responses than with non-replicating poxviral vaccine vectors, although a direct comparison has yet to be performed. NYVAC-KC is capable of replicating in human cells and displays enhanced immune activation, yet it remains highly attenuated in a mouse model of pathogenesis (Kibler et al., 2011; Quakkelaar et al., 2011), thus giving this particular vector many desirable traits of a vaccine vector and was chosen for use in the vaccine strategy described herein.

In some embodiments, the vaccine design strategy disclosed herein utilized the replicating vaccinia strain NYVAC-KC to express the full-length Gag or a fragment gp41 of HIV, for example a membrane anchored truncated gp41 presenting the membrane proximal external region with its conserved broadly neutralizing epitopes in the prefusion conformation (dgp41). As is well understood in the art, recombinant vaccinia virus is produced by inserting foreign genes into the thymidine kinase (TK) gene using homologous recombination. This is achieved by a recombination plasmid containing the TK locus with the foreign gene inserted between the homologous recombination arms. Accordingly, the vaccinia vector described herein comprises a nucleic acid encoding Gag or a fragment of gp41 (for example, dgp41) in the TK locus between the homologous recombination arms.

Vaccinia VLPs presenting Gag, a fragment of gp41 (for example, dgp41), or both can be produced from the described vaccinia vector by transfecting mammalian cells with these vectors and infecting the transformed mammalian cells with a replicating but highly attenuated vaccinia virus (for example NYVAC). Transfecting the mammalian cells with a vaccinia vector expressing Gag produces VLPs presenting Gag upon viral infection, while transfecting the mammalian cells with vaccinia vector expressing dgp41 produces VLPs presenting dgp41 upon viral infection. If the mammalian cells are transfected with both a vaccinia vector comprising Gag and a vaccinia vector comprising dgp41, however, then VLPs presenting Gag and dgp41 are produced. These VLPs can be administered to a mammalian subject to prime an immune response against HIV, for example, when used in combination with the HIV VLPs described herein. In some implementations, NYVAC-KC for expression of Gag and NYVAC-KC for expression of dgp41 of HIV-1 are used as matching antigens to the plant-produced VLPs for prime/boosting purposes. Accordingly, the disclosure relates to compositions comprising a replicating and highly-attenuated vaccinia virus vector expressing Gag and/or replicating and highly-attenuated vaccinia virus expressing a fragment of gp41 of HIV along with a construct for the expression of HIV VLP in plants. The vaccine strategy targets gp41 of HIV.

Infecting susceptible cells with NYVAC-KC-Gag with or without NYVAC-KC-dgp41 releases, respectively, ~100 nm Gag or Gag/dgp41 VLPs into the extracellular medium (FIG. 1E). Such particles can be seen by TEM budding out of the cell (FIGS. 2B-2 and D-2). dgp41 is detected in the medium only when co-expressed with Gag (FIG. 1E), a result compatible with the notion the two proteins assemble at the plasma membranes of cells in culture to form VLPs. Although other groups have shown that VLPs expressing HIV-1 proteins produced by other VACV-based vectors elicit both humoral and cellular immunity (Chen et al., 2005; Goepfert et al., 2011; Perdiguero et al., 2015), the experiments disclosed herein did not detect any antibodies in any test group until after the first plant-derived VLP immunization (FIG. 3B-C). Without being limiting to any one mechanism, one explanation of the difference in experimental results is that production of Gag/dgp41 VLPs in vivo necessitates co-infection of the same cell by the two viruses. While this is achievable under cell culture conditions where high MOI can be ensured, but co-infection of the same cell by the two viruses is unlikely to occur in an animal.

Accordingly, in another embodiment, the vaccinia virus vector co-expresses Gag and dgp41 from the same locus to ensure in vivo Gag/dgp41 VLP formation. As such, in some aspects, the vaccinia virus vector comprises a nucleic acid encoding Gag and a fragment of gp41 (for example, dgp41) in the TK locus between the homologous recombination arms. VLPs produced from infecting mammalian cells with this vaccinia virus vector, which would express Gag and dgp41, are also suitable for priming an immune response against HIV, for example, when used in combination with the HIV VLPs described herein.

Another explanation for the limited functionality of the dual vectors is the poor replication and/or spread in mice. In some aspects, poor replication and/or spread of the vectors is due to the cytotoxicity represented by protein precipitates in the cytoplasm and nuclear condensation in NYVAC-KC-Gag-, dgp41- or co-infected cells (FIG. 2B-2D). The toxicity seen with TEM strongly correlates to reduced plaque sizes and lower viral titers noted during viral selection. Gp41 is known to have a toxic cytoplasmic tail (Postler and Desrosiers, 2013; Micoli et al., 2006), so it can be responsible for the toxic effects seen in FIGS. 2A-2D. The cytotoxicity of full-length gp160 has largely limited the use of gp41 in vaccine candidates despite the appealing, highly conserved target region of the MPER. Additionally, this is consistent with published data that NYVAC expressing HIV Gag-Pol-Nef induces extensive apoptosis (Gomez et al., 2007). In one implementation, the toxicity of gp41 cytoplasmic tail is reduced by using other vaccinia virus strains that produces vaccine candidates with full-length gp160 in its native structurally accurate conformation.

4. Plant-Produced HIV VLPs

Plant production of recombinant proteins and pharmaceuticals offers multiple advantages, including lack of contamination by mammalian pathogens, less expensive scale-up, speed of expression, and platform flexibility (Horn et al., 2003; Ma et al., 2005; Daniell et al., 2009; Rybicki, 2009, 2010; Egelkrout et al., 2012). Many different types of VLPs have been produced in plants, for review see (Chen and Lai, 2013; Scotti and Rybicki, 2013). Several plant-made products have been tested in human clinical trials (Ma et al., 2005; Yusibov et al., 2014) and one product has been approved by the FDA for treatment of Gaucher disease (Zimran et al., 2011). Economic viability of plant production relies heavily on oftentimes poor yields, and downstream processing costs to remove host proteins accounts for ~80% of production expenditures (Egelkrout et al., 2012; Wilken and Nikolov, 2012).

Several transient deconstructed viral-based vectors for rapid, high level protein expression in plants are currently available. The tobacco mosaic virus (TMV)-based magnICON system has been extensively used to express recombinant proteins in plants since its invention and was the first to provide gram-levels of antigen (Marillonnet et al., 2004; Gleba et al., 2005; Marillonnet et al., 2005). However, other expression systems based on other plant viruses such as geminiviruses (Gemini) (Mor et al., 2003; Huang et al., 2009) and Cowpea mosaic virus (CPMV)-based pEAQ vectors (Sainsbury et al., 2009; Peyret and Lomonossoff, 2013) are less well characterized. The TMV system requires simultaneous delivery of three plasmids by *Agrobacterium tumefaciens* infiltration (agroinfiltration) to recombine in planta within the nucleus and the TMV movement protein transfers amplified mRNA to surrounding cells (Marillonnet et al., 2004). However, Gemini vectors are single plasmid delivery yet lack a movement protein and are known to induce gene silencing (Seemanpillai et al., 2003; Rodriguez-Negrete et al., 2009; Aregger et al., 2012) but this can be suppressed using the Tomato bushy stunt virus p19 protein (Silhavy et al., 2002; Voinnet et al., 2003; Garabagi et al., 2012). Furthermore, multiple proteins can be delivered on the same plasmid and expressed in separate replicons established by short and long intergenic regions (SIR/LIR) (Huang et al., 2009). After transfer to the nucleus, Gemini DNA is amplified via rolling-circle mechanism by the C1/C2 (Rep/RepA) proteins (Gutierrez, 1999; Mor et al., 2003).

HIV VLPs have been produced in plants with low yield, particularly of full-length Gag, being a common theme (Meyers et al., 2008; Kessans et al., 2013). Yield can be increased by expressing Gag in transgenic chloroplasts (Scotti et al., 2009). An efficient production method for enveloped VLPs in the tobacco-relative *Nicotiana benthamiana*, consisting of Gag and deconstructed-gp41 (dgp41: MPER, transmembrane domain, and full-length cytoplasmic tail) was developed (Kessans et al., 2013). Such VLPs display the MPER of gp41 without steric hindrance from gp120, without the immunodominant epitopes on both Env subunits, and with a higher antigen load per VLP than what exists in an HIV virion (Kessans et al., 2016). A similar construct has been shown by us to be a likely trimer with its bnAb epitopes exposed (Gong et al., 2015). When administered to mice, these VLPs elicit both serum IgG and mucosal IgA to Gag and dgp41 antigens (Kessans et al., 2016).

The described plant-produced HIV VLPs comprising full length Gag and a fragment of gp41 have the advantage of displaying the MPER of gp41 in the native context of a Gag matrix, providing an immunogenic platform for humoral responses to both antigens (Kessans et al., 2013, 2016). Additionally, HIV VLPs have been shown to boost T cell responses following a heterologous prime (Chapman et al., 2013; Chege et al., 2008; Pillay et al., 2010). CD8 T cell responses, often targeting the Gag protein, are known to be associated with reduced viral load, making this a key target for protective T cell immunity (Kiepiela et al., 2007; Koup et al., 1994; Mudd et al., 2012; Stephenson et al., 2012; Jiao et al., 2006). Plant-produced VLPs show proficiency for eliciting high Ab titers and may boost T cell responses primed by the NYVAC-KC vectors.

The primary roadblocks to plant-produced pharmaceuticals revolve around both purification and low yield/expression levels (Wilken and Nikolov, 2012). Recombinant protein often accounts for only 0.7-7% of total soluble protein (TSP) (Egelkrout et al., 2012) whereas rubisco is the most prominent soluble protein, and the most abundant protein in the world, at 30-50% of the plant TSP (Spreitzer and Salvucci, 2002; Feller et al., 2008). Removal of rubisco has plagued the plant-produced pharmaceutical field; however, recent developments show great promise at removing rubisco with simple chromatography and precipitation methods (Buyel et al., 2013; Buyel and Fischer, 2014; Arfi et al., 2016). One such study reports the ability to remove up to 92% of rubisco from plant extractions using polyethylene glycol (PEG) precipitation (Arfi et al., 2016). Described herein is a method for removing the primary large and small subunit bands of rubisco from our VLP preparations by simple ammonium sulfate precipitation (FIG. 4). The method comprises sequential ammonium sulfate precipitation of supernatant of homogenized recombinant plant tissue with starting concentration of 20% ammonium sulfate and an ending concentration at 40% ammonium sulfate. In one exemplary implementation, the supernatant of homogenized recombinant plant tissue is precipitated first at 20% ammonium sulfate followed by precipitation at 40% ammonium sulfate. The VLPs are pelleted at 36,000×g for 30 min at 4° C. between fractions. These are critical advancements because the economic advantage of using plants over other expression systems is touted by downstream processing accounting for up to 80% of production costs (Wilken and Nikolov, 2012).

a. Tobacco Mosaic Virus-Based Vector

The tobacco mosaic virus (TMV)-based magnICON system has been extensively used to express recombinant proteins in plants since its invention and was the first to provide gram-levels of antigen (Marillonnet et al., 2004; Gleba et al., 2005; Marillonnet et al., 2005). In some aspects, a tobacco mosaic virus-based vector encoding Gag and/or dgp41 is used to produce the HIV VLP. Accordingly, the tobacco mosaic virus-based vector comprises a T-DNA region comprising a nucleic acid sequence encoding Gag, dgp41, or both Gag and dgp41. In some embodiments, expression of Gag, dgp41, or a nucleic acid sequence encoding both Gag and dpf41 is driven by the nopaline synthase (NOS) promoter. In some embodiments, expression of Gag, dgp41, or a nucleic acid sequence encoding both Gag and dpf41 is driven by the cauliflower mosaic virus 35S promoter (P35). In some aspects, a nucleic acid sequence encoding an attB site is upstream of the nucleic acid sequence encoding Gag, dgp41, or both Gag and dgp41 and is downstream of the promoter.

The TMV system requires simultaneous delivery of three plasmids by *Agrobacterium tumefaciens* infiltration (agroinfiltration) to recombine in planta within the nucleus and the TMV movement protein transfers amplified mRNA to surrounding cells (Marillonnet et al., 2004).

b. Geminivirus-Based Vector

In other aspects, a geminivirus-based vector encoding Gag and/or dgp41 is used to produce the HIV VLP. Geminivirus-based vectors are single plasmid delivery that lack a movement protein and are known to induce gene silencing (Seemanpillai et al., 2003; Rodriguez-Negrete et al., 2009; Aregger et al., 2012) but this can be suppressed using the Tomato bushy stunt virus p19 protein (Silhavy et al., 2002; Voinnet et al., 2003; Garabagi et al., 2012). Furthermore, multiple proteins can be delivered on the same geminivirus-based plasmid and expressed in separate replicons established by short and long intergenic regions (SIR/LIR) (Huang et al., 2009). After transfer to the nucleus, Gemini DNA is amplified via rolling-circle mechanism by the C1/C2 (Rep/RepA) proteins (Gutierrez, 1999; Mor et al., 2003).

In some aspects, the geminivirus-based vector is a vector based on bean yellow dwarf virus (BYDV). Accordingly, the geminivirus-based vector comprises a T-DNA region comprising at least one replicon gene and a nucleic acid sequence encoding Gag and/or a nucleic acid encoding dgp41, wherein the at least one replicon gene is downstream of the nucleic acid sequence encoding Gag and the nucleic acid encoding dgp41. Where the T-DNA region of the geminivirus-based vector comprises a nucleic acid sequence encoding Gag and a nucleic acid encoding dgp41, in some embodiments, the nucleic acid sequence encoding dgp41 is upstream of the nucleic acid sequence encoding Gag. In some embodiments, the T-DNA region comprises a nucleic acid encoding Rep/RepA. In certain embodiments, the BYDV short intergenic region is upstream of Rep/RepA.

In some embodiments of the geminivirus-based vector, Gag and dgp41 expression is under the control of P35. Thus, in certain embodiments of the geminivirus-based vector, the T-DNA region further comprises a promoter upstream of the nucleic acid sequence encoding Gag and the nucleic acid encoding dgp41, where the promoter region comprises a nucleic acid sequence encoding P35. In some aspects, the promoter region further comprises two translation enhancer binding sites (2e), which are downstream of the nucleic acid sequence encoding P35. In certain embodiments, the geminivirus-based vector further comprises a barley α-amylase signal peptide upstream of the nucleic acid encoding dgp41 but downstream of the promoter region.

In some aspects, the T-DNA region of the geminivirus-based vector also comprises two BYDV long intergenic regions. One long intergenic region is upstream of the promoter region, and one long intergenic region is downstream of the at least one replicon gene. Where the T-DNA region of the geminivirus-based vector comprises a nucleic acid sequence encoding Gag controlled by one promoter region and a nucleic acid encoding dgp41 controlled by another promoter region, the long intergenic regions flank the portion of the T-DNA region containing the nucleic acid sequence encoding Gag, the nucleic acid encoding dgp41, and the at least one replication gene.

In particular embodiments, the T-DNA region of the geminivirus-based vector further comprises a nucleic acid sequence encoding a silencing suppressor protein. In some aspects, the silencing suppressor protein is p19, for example, tomato bushy stunt virus p19. The expression of the silencing suppressor protein by the geminivirus-based vector delays the onset of plant cell necrosis when compared with plant cells transformed with geminivirus-based vectors lacking a nucleic acid sequence encoding the silencing suppressor protein. The nucleic acid sequence encoding the silencing suppressor protein is upstream of the nucleic acid sequence encoding Gag and the nucleic acid encoding dgp41 and is upstream of the region flanked by the long intergenic regions. In some aspects, expression is silencing suppressor protein is controlled by a promoter downstream of the nucleic acid sequence encoding the silencing suppressor protein. In certain embodiments, the promoter is NOS.

Illustrative, Non-Limiting Example in Accordance with Certain Embodiments

The disclosure is further illustrated by the following examples that should not be construed as limiting. The contents of all references, patents, and published patent applications cited throughout this application, as well as the figures, are incorporated herein by reference in their entirety for all purposes.

1. Prime/Boost Anti-HW-1 Vaccination Strategy
   a. Materials and Methods
     i. Cloning pGNR Plasmids for Virus Recombination Construction of synthetic genes encoding Gag (from subtype C R5 HIV-1 isolate 1084i, GenBank #AY805330; synthetic construct GenBank #JX534517) and dgp41 (MPER derived from the B-clade MN isolate, GenBank #AF075722, transmembrane and C-terminal domains from the 1084i isolate #AY805330; synthetic construct #JX534518) was previously described (Kessans et al., 2013). The genes were cloned into the pGNR plasmid, which harbors a neoGFP selection cassette (neomycin resistance gene fused to GFP, known as pGNR) between homologous recombination arms for the vaccinia TK locus. Gag and dgp41 genes were amplified from pTM 488 (Gag) and pTM 602 (dgp41) [described in (Kessans et al., 2013)] into TOPO pCR-2.1 vectors (Invitrogen). Cloning was achieved using AccuStart Taq DNA polymerase HiFi PCR kit (Quanta Biosciences) with primers oTM 664 (SEQ ID NO. 1: 5'-ACTAGTATGGGAGCTAGAGCCTCT-3') and 665 1 (SEQ ID NO. 2: 5'-CCCGGGTTATTGAGAGGAAG-3') for Gag and oTM 666 (SEQ ID NO. 3: 5'-ACTAGTATGG-GATCTCAAACTCAACAA-3') and 1667 (SEQ ID NO. 4: 5'-CCCGGGTTATTGCAAAGCAG-3') for dgp41 for the addition of 5' flanking SpeI and 3' flanking XmaI sites, denoted in italics. Ligation reactions were electroporated into DH5 α *Escherichia coli* and plated onto LB +ampicillin plates. Gene insertion was confirmed by colony PCR using GoTaq Green Master Mix (Promega). Plasmids were extracted using the E.Z.N.A. mini-prep kit (Omega) and sequences verified using backbone-specific primers M13-forward and M13-reverse. The TOPO plasmids were designated pTM 813 (Gag) and pTM 814 (dgp41). Both pTM 813, 814, and pGNR were digested with SpeI and XmaI (NEB) and fragments separated via gel electrophoresis and extracted using QIAquick Gel Extraction Kit (Qiagen), then ligated into the pGNR backbone using T4 DNA ligase (Promega). Ampicillin resistant DH5a *E. coli* colonies were screened by colony PCR and plasmids extracted as above. Sequences were confirmed with pGNR backbone-specific primers oTM 686 (SEQ ID NO. 5: 5'-CCCACCCGCTTTT-TATAGTAA-3') and 687 (SEQ ID NO. 6: 5'-CGGTT-TATCTAACGACACAACA-3'). Sequence-verified pGNR plasmids were named pTM 815 (Gag) and pTM 816 (dgp41).

ii. Cell Lines and Viruses

Monkey kidney BSC-40 cells were grown in DMEM (Corning Cellgro) with 5% FBS plus gentamycin and 2 mM L-glutamine. Baby hamster kidney BHK cells were grown in MEM (Corning Cellgro) with 5% FBS plus gentamycin. Generation of the parental vaccinia virus (VACV) strain NYVAC-KC was described previously (Kibler et al., 2011).

iii. In Vivo Recombination (IVR)

Simultaneous transfection/infection [in vivo recombination, IVR (Kibler et al., 1997; Brandt and Jacobs, 2001)] was performed with pTM 815 (Gag) and pTM 816 (dgp41) and NYVAC-KC to insert Gag and dgp41 into the vaccinia virus TK locus. 500 ng of plasmid DNA was transfected using Lipofectamine and Plus™ Reagent (Invitrogen) per manufacturer's protocol. This was immediately followed by infection with NYVAC-KC at an MOI=0.01 in 35 mm2 dishes of BSC-40 cells. Recombination was allowed to proceed for 24 h followed by addition of G418 antibiotic (500 μg/mL). Cells were harvested and lysed at 48 h post infection (hpi). The IVR was used to infect 100 mm2 dishes of BSC-40 cells for selection of individual antibiotic-resistant plaques for subsequent expression screening (note: a mutation in the GFP gene prevented use of fluorescent screening). This process was repeated for multiple rounds of antibiotic selection before a >98% pure virus was isolated as measured by immunoplaque assay.

iv. Expression Screening

Individual antibiotic-resistant plaques were grown in 60 mm2 dishes of BSC-40 cells to CPE and harvested in 1×SDS sample buffer [50 mM Tris-Cl pH 6.8, 2% SDS, 0.1% bromophenol blue, 10% glycerol, 100 mM β-mercaptoethanol, 1× protease inhibitor cocktail III (Research Products International Corp., Prospect, IL)] and then centrifuged through a QiaShredder (Qiagen) for NYVAC-KC-Gag plaques. For NYVAC-KC-dgp41, cells were lysed with RIPA lysis buffer [1% NP40, 0.1% SDS, 0.5% sodium deoxycholate, 1× protease inhibitor cocktail III, in 1×PBS without calcium or magnesium (Corning)]. RIPA lysates were mixed with an equal volume of 2×SDS sample buffer. Cell lysates were screened using SDS-PAGE as previously described (Kessans et al., 2013). Briefly, boiled samples were run on 12% polyacrylamide gels under denaturing conditions, transferred to nitrocellulose membranes (Bio-Rad) and probed with either Gag or dgp41 antibodies and anti-rabbit or anti-human IgG-HRP, respectively. Proteins were detected via chemiluminescence (ImmunoCruz Luminol Reagent, Santa Cruz).

v. Immunoplaque Assays

Immunoplaque assays were performed in 6-well dishes by infecting BSC-40s with 50 pfu from cell lysates of individual plaques. Once plaques were visible, the cells were fixed with 1:1 acetone:methanol for 30 min at −20° C., washed with PBS, then incubated with anti-p24 Gag polyclonal rabbit serum or 2F5 (obtained through the NIH AIDS Reagent Program, Division of AIDS, NIAID, NIH: from Dr. Hermann Katinger) at 1:1000 in 3% FBS-PBS. Secondary biotinylated antibodies for anti-rabbit IgG or anti-human IgG from Vectastain ABC Kits (Vector Laboratories, Inc.) were used for detection with DAB peroxidase substrate (Vector Laboratories, Inc.) per manufacturer's protocol. After counting positive plaques, cells were stained with Coomassie blue dye to count the number of negative plaques. Percentages were calculated by dividing positive plaques by total plaques per well. The plaque with the highest percentage of positives was used for further purification until a plaque with >98% purity was identified and used to grow stocks.

vi. Virus Stocks

The final NYVAC-KC-Gag and NYVAC-KC-dgp41 plaques with >98% purity determined by immunoplaque assay were grown to CPE in BHK cells in a 60 mm2 dish for the first passage (P1) stock. The P1 stock was titered in BSC-40s and used to infect five T150 flasks of BHK cells at an MOI=0.01 for the P2 stock. Cells were harvested at CPE, subjected to freeze-thaw and sonication, then cell lysates were placed on a 36% sucrose pad and centrifuged at 22,000 rpm for 80 min at 4° C. with an SW28 rotor to pellet virions. Partially purified virions were resuspended in 10 mM Tris-HCl pH 9.0, their titer determined in BSC-40s, and were stored in aliquots at −80° C. until further use.

vii. Vaccinia In Vitro VLP Production

BSC-40 cells seeded in 100 mm2 dishes were infected with each of the vectors at an MOI=5 for a total MOI=10. At 24 hpi, medium and cells were harvested by centrifugation (700×g for 5 min). VLPs in the clarified medium were subjected to 40% ammonium sulfate precipitation and resuspended in 1×PBS (140 mM NaCl, 2 mM KCl, 10 mM Na2HPO4, 1 mM KH2PO4, pH 7.4). Aliquots were boiled and analyzed by SDS-PAGE for presence of Gag and dgp41 as described above.

viii. Expression in Plants of VLPs and their Purification

HIV-1 Gag/dgp41 VLPs were expressed and purified as previously described (Kessans et al., 2013). Briefly, Gag transgenic *N. benthamiana* plants were infiltrated with *Agrobacterium tumefaciens* harboring pTM 602 with the dgp41 gene and leaf tissue was harvested 4-6 days post infiltration (dpi). Leaf tissue was crushed in a blender in extraction buffer (25 mM sodium phosphate, 100 mM NaCl, 1 mM EDTA, 50 mM sodium ascorbate, 1 mM PMSF, pH 7.8). VLPs were precipitated with 40% ammonium sulfate and resuspended in 1×PBS (140 mM NaCl, 2 mM KCl, 10 mM Na2HPO4, 1 mM KH2PO4, pH 7.4), then purified via iodixanol density gradient centrifugation. The VLP-containing 20% iodixanol fraction was concentrated on a 300 kDa molecular weight cut-off membrane (Sartorius) and quantified via immunoblot for immunizations as described in (Kessans et al., 2016). A typical total yield of a highly enriched VLP preparation in terms of its HIV-1 protein constituents was 275 mg/kg and 92 mg/kg for Gag and dgp41, respectively.

ix. Antibodies

The following antibodies were used for the indicated assays: anti-p24 Gag polyclonal rabbit serum (Kessans et al., 2013); human anti-MPER 2F5 (AIDS Reagent Program and the kind gift of Morgane Bomsel); goat anti-human IgG-HRP (Sigma) for immunoblot; goat anti-rabbit IgG-HRP (Santa Cruz) for immunoblot; rabbit anti-human IgG-HRP (Santa Cruz) for ELISAs; rabbit anti-mouse IgG-HRP (Calbiochem) for ELISAs; mouse IgA-kappa (ICL Labs) for ELISAs; goat anti-mouse IgA (Sigma) for ELISAs.

x. Transmission Electron Microscopy (TEM)

BSC-40 cells grown in T75 flasks were infected with each of the vectors at an M01=5 (for a total MOI=10) and harvested by trypsinization 24 hpi. Cells were pelleted between all wash steps at 700×g for 5 min at 4° C. until embedded in agarose prior to secondary fixation. Pelleted cells were washed twice in 1×PBS (140 mM NaCl, 2 mM KCl, 10 mM Na2HPO4, 1 mM KH2PO4, pH 7.4). For primary fixation, cells were placed in 2% glutaraldehyde in PBS for 15 min at room temperature followed by a second incubation with fresh fixative for 1 h at 4° C. Fixed cells were resuspended in 1% agarose and washed three times in PBS for 30 min each at room temperature. Cells were then fixed with 1% osmium tetroxide in PBS for 1 h at room temperature followed by four 15-min washes in water. A 0.2% uranyl acetate solution in water was used to stain en bloc overnight at 4° C. followed by three 15-min washes in water. An ethanol series from 20% to 100% (anhydrous) was used for dehydration, increasing the ethanol concentration by 20% every 10 min with three incubations in anhydrous ethanol. Spurr's resin was gradually introduced through 4- to 8-h incubations with 1:3, 1:1, and 3:1 ratios of resin:100% ethanol followed by three incubations in 100% resin. Cells were divided into several blocks of Spurr's resin and polymerized at 60° C. for 36 h. Sections were cut at 70 nm thick and were placed on formvar-coated copper slot grids followed by post-stain treatment with 2% uranyl acetate and 3% Sato's lead citrate before imaging.

xi. Mouse Immunizations

All animal experiments were done with approval from the Arizona State University Institutional Animal Care and Use Committee.

Six-week-old C57BL/6 mice (Jackson Laboratories) were split into five groups. Three groups (n=5) received virus prime (VV) followed by two boosts of either mock (Group 1), VLP (Group 2), or VV+VLP (Group 3). Group 4 (n=3) received no virus prime and two VLP boosts and Group 5 served as the naive control (n=1). NYVAC-KC-Gag and NYVAC-KC-dgp41 P2 stocks, each at a dose of $5 \times 10^5$ pfu, were mixed together for a total dose of $1 \times 10^6$ pfu per mouse. Virus immunizations prepared in Tris HCl pH 9.0 were injected intramuscularly (i.m.) into the thigh. Plant-produced, gradient-purified VLPs were prepared in 1×PBS pH 7.4 with 2 µg p24 and 1.2 µg MPER and mixed with Ribi adjuvant (Sigma) per manufacturer's protocol to reach a final concentration of 2% oil [described previously in (Kessans et al., 2016)]. Mock mice were injected i.m. with Tris HCl pH 9.0 buffer in equivalent volumes. VACV and vehicle injections were delivered i.m. while VLPs were delivered intraperitoneally (i.p).

Three immunizations were given to mice at days 0, 45, and 90. Serum, fecal, and vaginal lavage samples were collected as previously described (Kessans et al., 2016) every 2 weeks at days 0, 14, 28, 42, 56, 80, and at the endpoint of day 97 for analysis of Ab production. One week post the final boost (day 97), spleens were collected for analysis of CD8 T-cell responses as described below.

Animals were monitored every 2-3 days for weight loss and other signs of illness, as a measure of vector safety.

xii. ELISA Detection of IgG and IgA

Antibody production was measured via ELISA as previously described (Kessans et al., 2016). Briefly, serum, fecal, and vaginal lavage samples were analyzed for IgG (serum) or IgA (mucosal sites) specific for Gag p24 or gp41 MPER regions. Samples were analyzed in threefold serial dilutions starting at 1:50, 1:2, and 1:5 for serum, fecal, and vaginal lavage samples, respectively. Endpoint titers were calculated as the reciprocal of the dilution factor at which OD 490 nm was equal to background levels (OD490<0.1) as previously described (Matoba et al., 2008; Kessans et al., 2016). IgG1 and IgG2a isotypes were detected with the same ELISA protocol, but with goat anti-mouse IgG1-HRP or goat anti-mouse IgG2a-HRP secondary antibodies (Santa Cruz Biotechnology) instead of total IgG. Purified mouse IgG1 kappa chain or mouse IgG2a kappa chain primary antibodies (Sigma) were used as controls.

For anti-VACV ELISAs, 96-well plates were coated with $10^7$ pfu/well of sucrose-cushion purified NYVAC-KC in 1×PBS, and the plates were overnight at 37° C. Wells were fixed in 2% paraformaldehyde in 1×PBS for 10 min at 4° C. to inactivate the virus. Wells were washed with buffer (150 mM NaCl, 0.5% Tween-20) then blocked with 5% nonfat milk in 1×PB ST. Plates were overlaid with serially diluted serum samples and detected as previously described (Matoba et al., 2008; Kessans et al., 2016).

xiii. Intracellular Cytokine Staining and Flow Cytometry

Spleens were harvested in Hank's medium (Corning Cellgro) and cells were strained through a 70 µm filter for resuspension in complete RPMI [cRPMI: 10% FBS, penicillin (100 units/mL), streptomycin (100 µg/mL), 2 mM L-glutamine]. Red blood cells were lysed with ACK Lysing Buffer (Gibco) and splenocytes were resuspended in cRPMI at a concentration of 2×107 cells/mL. Cells were plated at 1×106 cells/well and incubated for 5 h in the presence of Golgi Plug (BD Biosciences) and 1 µg of one of five different immunodominant ZM96 Gag CD8 epitopes: LRS-LYNTV (LRS8, SEQ ID NO. 7), VIPMFTAL (VIP8, SEQ ID NO. 8), AMQMLKDT (AMQ8, SEQ ID NO. 9), YSPVSILDI (YSP9, SEQ ID NO. 10), EVKNWMTDTL (EVK10, SEQ ID NO. 11) (synthesized by GenScript and resuspended according to manufacturer's protocol). Cells were stained with fluorescently conjugated antibodies: CD8-Pacific Blue, TNFα-FITC, and IFNγ-PE (BD Biosciences). Fixation and permeabilization was performed with a Cytofix/Cytoperm Kit (BD Biosciences) with final resuspension in FACS Buffer (1% FBS in 1×PBS). Samples were analyzed by flow cytometry on an LSR Fortessa. Data was analyzed using FlowJo Data Analysis Software (FlowJo, LLC; Ashland, OR).

xiv. Statistics

All statistical analyses were performed in GraphPad Prism Software (GraphPad Prism Software Inc.; La Jolla, CA). All data were analyzed using a one-way ANOVA multiple comparison with Dunn's post-test. Significance cut-off was defined as $p<0.05$.

b. Generation of Recombinant Vaccinia Virus Vectors

Figure 1C:
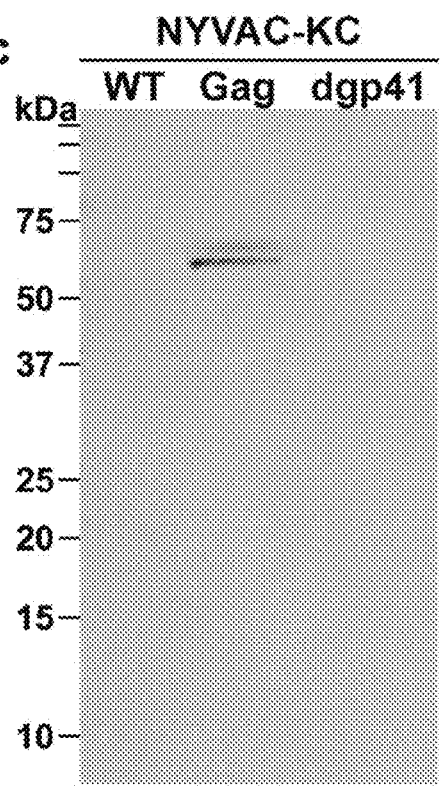
Figure 1D:
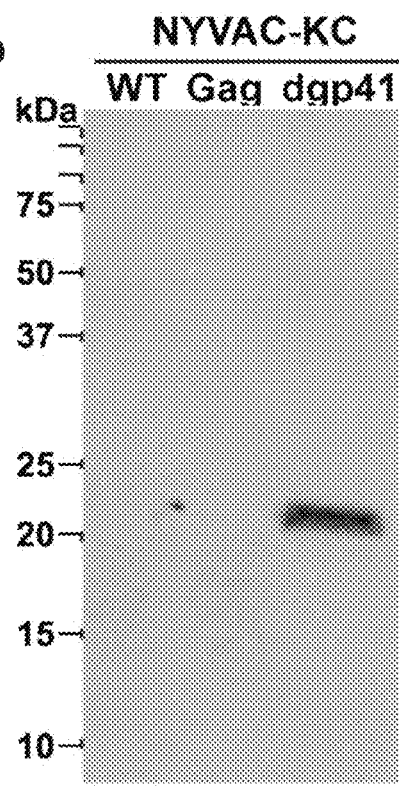
Figure 1E:
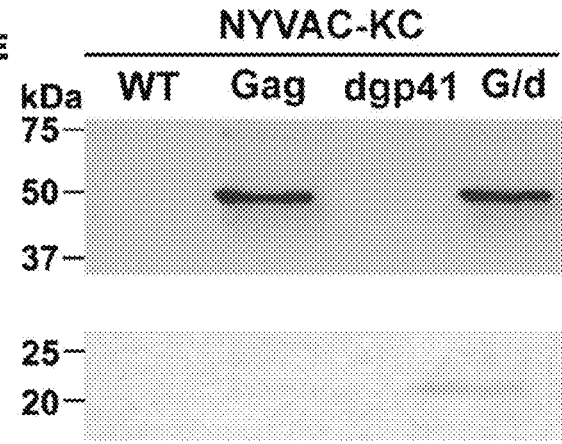

NYVAC-KC-Gag and NYVAC-KC-dgp41 viruses were generated through in vitro recombination (see Materials and Methods) (FIGS. 1A and B). Each gene was under control of a synthetic early/late VACV promoter, ensuring the genes were expressed at all stages of viral replication to maximize antigen production. Second round individual plaques were screened for expression via immunoblot by probing for either Gag or dgp41 expression. Immunoplaque assays for either Gag or dgp41 were performed to identify the plaque with highest purity for further selection. This process was repeated until a plaque with >98% purity was identified and then used to grow a P2 stock. The final sucrose-pad purified P2 stock show Gag and dgp41 expression in BSC-40 cell lysates at the proper size (FIGS. 1C and D). It was noted during selection that viruses recombining with dgp41 plasmids had reduced plaque size and grew to much lower titers, suggesting that the HIV-1 gene makes the viral vector cytotoxic (data not shown).

Gag is known to be sufficient and necessary for HIV-1 VLP formation and budding into the medium (Garoff et al., 1998). To test whether BSC-40-infected cells support VLP formation and budding, culture medium was analyzed for the presence of Gag and dgp41. Indeed, Gag protein was detected in culture medium of cells either infected with NYVAC-KC-Gag or co-infected with NYVAC-KC-Gag and NYVAC-KC-dgp41 (FIG. 1E, Lanes 2 and 4). In contrast, dgp41 was detected only in the medium from co-infected cells, not in medium from cells that were infected with NYVAC-KC-dgp41 alone (FIG. 1E, Lane 4).

c. NYVAC-KC-Gag/Dgp41 Show Cytotoxicity and In Vitro VLP Production

These results indicate that export of dgp41 to the medium depends on expression and export of Gag, suggesting that Gag VLPs and Gag/dgp41 VLPs are released, respectively, from cells that express Gag alone or co-express Gag and dgp41. Inventors used TEM to test this possibility. BSC-40 cells that were infected (MOI=5) with NYVAC-KC, NYVAC-KC-Gag, NYVAC-KC-dgp41, or co-infected with Gag/dgp4, were processed for TEM at 24 hpi.

In cells infected with the parental NYVAC-KC strain, viral replication factories are clearly visible and all stages of viral replication are easily identified (FIG. 2A). Mature virions (indicated by white arrows) are seen both intracellularly (FIG. 2A-1) and extracellularly (FIG. 2A-2). Immature virions with and without incorporated genomes are also abundantly visible in this section (white and black triangles, respectively).

NYVAC-KC-Gag-, dgp41-, or co-infected cells have disorganized viral factories and mature viral particles are rare (FIG. 2B-D). Many early crescent formations are visible (black arrow), along with what appears to be "unfilled" or empty virion shells (indicated by "E"). The rarity of mature virus particles corresponds well to the smaller plaques typical of these strains and their reduced titers, as noted above. Instead, these infected cells appear to have large protein aggregates or precipitates in their cytoplasm ("junk" indicated by "J"), mimicking a phenotype associated with palmitate deficiency (Greseth and Traktman, 2014). Additionally, NYVAC-KC-dgp41-infected cells demonstrate nuclear condensation (FIG. 2C-2, "nucleus" indicated by "N"), a classic sign of apoptosis (Duprez et al., 2009). Furthermore, the mitochondria (indicated by "M") in NYVAC-KC-Gag- and NYVAC-KC-dgp41-infected cells appear to be malformed, potentially indicating loss of structural integrity, which can also indicate occurrence of apoptosis (Li and Dewson, 2015). This phenotype seems far more drastic than that of NYVAC-KC-infected cells.

Importantly, in cells that were infected with NYVAC-KC-Gag (FIG. 2B-2) or co-infected with NYVAC-KC-Gag and NYVAC-KC-dgp41 (FIG. 2D-2), particles of approximately 100 nm in diameter are seen budding at the cell surface (black stars). Similar structures were not observed in any of the sections of cells expressing by itself dgp41. Based on their size, and appearance, the particles are likely to be HIV-1 Gag or Gag/dgp41 particles budding out of the cell. This identification is supported by our observation that Gag and dgp41 accumulated in the media of these infected cells (FIG. 1E).

i. Mouse Immunizations

Six-week-old C57BL/6 mice were separated into five groups in order to assess different combinations of VACV and VLP immunization regimens (FIG. 3A). Mice were given a total of three immunizations separated by 45 days to allow for memory responses to develop prior to boosting. Three groups (n=5) were primed with the combination of NYVAC-KC-Gag and NYVAC-KC-dgp41 (denoted in all figures and text as VV), followed by two boosts with either vehicle (Group 1), VLPs alone (Group 2), or a combination of VV and VLPs (Group 3). A fourth group (n=3) received a mock (vehicle) prime followed by boosts with VLPs. The fifth group served as a naive control (n=1).

Monitoring of weight revealed that none of the mice in any group lost weight (data not shown). This indicates little to no pathogenicity of the virus and is consistent with previous virulence data for NYVAC-KC (Kibler et al., 2011) and general safety of the plant-derived VLPs (Kessans et al., 2016).

d. Serum IgG Responses to Gag and MPER

Antigen-specific serum IgG responses were measured by ELISA using p24 subunit or MPER peptide to detect Gag and dgp41 Ab responses, respectively. Throughout, OD 450 nm values for the lowest dilution tested (1:50) are shown both over time (FIG. 3B-C) and for individual animals at the endpoint, Day 97 (FIG. 4A). Additionally, endpoint titers were calculated for the final serum samples and are shown in FIG. 5A as the reciprocal of the dilution where the OD 450 nm fell below background levels (OD<0.1).

Serum IgG responses against both p24 and MPER antigens remained undetectable in all groups until the first sample (Day 55) after the first boost. Titers increased gradually and were boosted after the final immunization with VLPs (FIG. 3B-C), reaching significant levels at the endpoint analysis (Day 97) for both anti-p24 Gag and anti-MPER responses (FIG. 4A). Endpoint Gag responses were highest in the group boosted with a combination of VV and VLPs (VV/VV +VLPs), while the group boosted with VLPs alone (VV/VLPs) also showed significant titers which were more variable responses among animals (FIG. 5A). Anti-MPER serum IgG responses were lower than Gag titers but showed a similar trend, reaching significant levels in all groups receiving VLPs regardless of prime/boost regimen (FIG. 4A). However, the endpoint titer calculations showed no difference between groups, consistent with low Ab responses (FIG. 5A). It is interesting to note that plant-produced VLPs appear to be largely responsible for Ab stimulation because no detectable levels of antibodies were present in the first 45 days after a single dose of VV and only reached detectable levels after the second immunization in those groups that received VLPs.

e. Mucosal IgA Responses to Gag and MPER

Gastrointestinal IgA responses to the dgp41 (MPER) antigen (as determined by measuring the secreted Ab levels in fecal samples) were low but detectable (FIG. 4B), whereas anti-MPER IgA levels in vaginal secretions were below our detection level irrespective of treatment (FIG. 4C). Fecal anti-MPER IgAs were higher in groups that were immunized using the prime/boost VV/VLPs regimen than groups that were vaccinated with either VV or VLPs alone. Contrasting the two groups, those mice that were boosted with a combination of VV and VLPs exhibited marginally higher levels of fecal IgAs than those boosted with VLPs alone, but their fecal IgA levels were significantly higher than the group that was primed with VV only. Interestingly, levels of fecal and vaginal anti-p24 Gag IgAs were too low for detection in all groups. This contrasts sharply with the generally much higher titers of serum anti-p24 Gag IgGs as compared to serum anti-MPER IgGs.

f. IgG Isotyping

The two major IgG isotypes are IgG1 and IgG2a; the former is consistent with stimulation of a Th2 response for B cell activation, whereas the latter would be indicative of a Th1 response, which primarily results in inflammatory cytokine production and killing of intracellular pathogens (Snapper and Paul, 1987; Szabo et al., 2003). Results indicated that the most important immunogens contributing to the elicitation of serum IgGs are the plant-derived VLPs. To further substantiate this conclusion, we determined the Ab isotypes contributing to this response, as protein-based vaccines (i.e. immune-complexes) usually elicit IgG1 (Mosser and Edwards, 2008; Martinez and Gordon, 2014).

To this end, serum samples from the endpoint for the two groups which showed the highest serum IgG responses (VV/VLP and VV/VV +VLP) were analyzed for their IgG isotype content by isotype-specific ELISA (FIGS. 5A and B, respectively). Both groups show high levels of antigen-specific (either anti-p24 or anti-MPER) IgG1, but levels of IgG2a were too low for detection.

g. Anti-Vector Antibody Responses

Having substantiated the contribution of the Gag/dgp41 VLPs for the elicitation of serum Ab responses against the two HIV-1 antigens, the question arose whether or not the viral vector induced production of anti-vector (i.e. anti-VV) serum Abs. Mice belonging to Group 3 that received a total of three doses of VV (prime plus two boosts) showed significant levels of anti-VV serum IgG at the endpoint (Day 97, FIG. 6). However, a single dose of VV at Day 0 was not enough to induce a potent anti-vector response (Group 1).

h. Gag-Specific CD8 T Cell Responses

A major rationale to include Gag in an HIV-1 vaccine, especially a live-vectored one, is its excellent ability to induce cellular responses. To test induction of CD8 T cell responses, inventors tested the ability of peptides corresponding to known Gag T-cell epitopes to stimulate proliferation of CD8 T-cells among splenocytes obtained from vaccinated animals. One week after the final boost, splenocytes were harvested and stimulated with five CD8 ZM96 Gag peptides that were previously determined to be dominant in C57BL/6 mice (Chowell et al., 2015). Peptides were assessed individually in order to obtain a better resolution of their responses. CD8 T cells were analyzed for IFN-γ or TNF-α production in response to peptide stimulation using cytokine staining and flow cytometry. Little to no TNF-α production was seen in the flow cytometry analysis (data not shown); however, IFN-γ production was detectable in several groups. The group boosted with both VV and VLPs showed significant production of IFN-γ with two of the five Gag peptides, AMQ8 and EVK10, at $2.6 \times 10^5$ CD8$^+$ IFN-γ+ T cells (3.5% of CD8$^+$ T cells) and $1.91 \times 10^5$ CD8+ IFN-γ+ T cells (2.4%), respectively (FIGS. 7A and B). The other three peptides, LRS8, VIP8, and YSP9 showed a similar trend as AMQ8 and EVK10 but with slightly lower responses of CD8+ IFN-γ+ T cells at $1.73 \times 10^5$ (2.4%), $1.61 \times 10^5$ (2.1%), and $1.67 \times 10^5$ cells (2.3%), respectively, but failed to reach significance (FIG. 7C-E). When responses from all five peptides are added together, the VV/VV+VLPs group has a total CD8 Gag-specific mean response of $9.53 \times 10^5$ CD8+ IFN-γ+ T cells (12.7% of CD8 T cells) (FIG. 7F). The total Gag-specific CD8 responses of the other groups show minute differences between groups at 8.0% in Tris/VLP, 5.6% in VV/VLP, and 4.2% in VV/Tris. This suggests that plant-derived Gag/dgp41 VLPs may be providing some component of the T cell response and potentially boosting the initial VV-primed T cell responses as previously described for other Gag-containing VLPs (Williamson and Rybicki, 2015).

2. Transient, Deconstructed Tobacco Mosaic Virus- and Geminivirus-Based Vectors for Enhancing Expression and Yield of HIV-1 Gag/Dgp41 Virus-Like Particles a. Experimental Procedures i. Cloning Geminivirus-Based Vectors The TMV-based vector, pTM 602, was previously described (Kessans et al., 2013). Geminivirus-based vectors were generously provided by Dr. Hugh Mason (Arizona State University) for cloning dgp41 and Gag. Three vectors were generated: pTM 924 (Gemini), pTM 925 which contains p19 (Gemini +p19), and pTM 901 (Dual Gem. +p19), a dual-replicon vector for simultaneous expression of two genes from the same backbone which also contains p19.

For cloning into pTM 924 and pTM 925, dgp41 was digested from pTM 602 using NcoI and SacI. The barley α-amylase (BAA) signal peptide was digested from pTM 796 using XbaI and SacI. The geminivirus backbone for pTM 924 is pTM 890 (formerly pBYR2fb) which was opened with XbaI and SacI. A triple ligation with dgp41, BAA, and the opened pTM 890 backbone using T4 DNA Ligase (Promega) yielded pTM 924. To derive pTM 925, the backbone pTM 800 was linearized using XbaI and SacI and the BAA-dgp41 insert was derived from pTM 924 by digesting with XbaI and SacI. The backbone and BAA-dgp41 fragment was ligated to yield pTM 925. Colonies were screened and sent for sequencing to confirm no mutations.

The dual-replicon vector, pTM 901, requires cloning into the XbaI/SacI cut site first due to the presence of a KpnI cut site in the multiple cloning site because the second cut site requires digestion with BsrGI and KpnI. BAA-dgp41 was excised from pTM 924 using XbaI and SacI while pTM 900 (formerly pBYR27p) was linearized using the same restriction sites. After confirming BAA-dgp41 insertion into the first cloning site, Gag was amplified from pTM 488 via PCR using AccuStart Taq DNA Polymerase HiFi (Quanta Biosciences) using oTM 776 (SEQ ID NO. 12: 5'-GAGATGTA-CAATGGGAGCTAGAGCCTCT-3') and oTM 777 (SEQ ID NO. 13: 5'-GAGAGGTACCTTATTGAGAGGAAGGGT-3') for addition of a 5' BsrGI and 3' KpnI cut site, shown in italics, and ligated to a TOPO TA backbone (Invitrogen). The Gag gene contained a BsrGI cut site which was removed via mutagenesis using whole plasmid replication with the QuikChange II Site-Directed Mutagenesis Kit (Agilent Technologies) per manufacturer's protocol. The first reaction changed a TTG codon to CTG using primers oTM 827 (SEQ ID NO. 14: 5'-GAGGAGCTTAGGTCTCTGTA-CAACACAGTGGCT-3') and oTM 828 (SEQ ID NO. 15: 5'-AGCCACTGTGTTGTACAGAGACCTAAGCTCCTC-3') where the mutated nucleotide is underlined. However, this introduces a non-synonymous codon so an additional change from CTG to CTC was performed using oTM 829 (SEQ ID NO. 16: 5'-GAGGAGCTTAGGTCTCTCTA-CAACACAGTGGCT-3') and oTM 830 (SEQ ID NO. 17: 5'-AGCCACTGTGTTGTAGAGAGACCTAAGCTCCTC-3'). Upon sequence confirmation this plasmid was named pTM 923. From there, pTM 923 and pTM 901 with BAA-dgp41 inserted were both digested using BsrGI and KpnI and then ligated together to derive the complete pTM 901. Sequences were confirmed for both Gag and dgp41 prior to use.

Each vector was transformed into GV3101 *Agrobacterium tumefaciens* and colony-screened to confirm transformation. An isolated colony was grown and used to start infiltration cultures for each of the three Geminivirus-based vectors.

ii. Kinetics Time Course

Six-week old *Nicotiana benthamiana* plants were vacuum infiltrated with an OD600=0.1 of *Agrobacterium tumefaciens* resuspended in infiltration buffer (10 mM MES, 10 mM magnesium sulfate heptahydrate, pH 5.5). Bacteria harboring pTM 602, 924, or 925 were infiltrated into Gag transgenic plants while pTM 901 was used in wild-type plants. Leaves were collected in triplicate every day for one week following infiltration. Collected leaves were scanned to monitor necrosis prior to flash-freezing 200 mg tissue samples in liquid nitrogen for expression analysis. Upon time-course completion, frozen tissue samples were homogenized in 1×SDS sample without dye (60 mM Tris-HCl, 100 mM DTT, 1.6% SDS (w/v), 5% glycerol) buffer using a ceramic bead in a Fast Prep-24 (MP Biomedicals, Solon, OH) machine twice for 30 s each. Homogenized samples were clarified by centrifugation at 14,000×g for 10 min at 4° C. Supernatant was collected and analyzed by Bradford assay (Bio-Rad) to determine total soluble protein (TSP) concentration. 20 µg TSP was loaded for each leaf sample into their respective lanes on a 12% polyacrylamide gel for SDS-PAGE followed by immunoblot as previously described (Kessans et al., 2013). Immunoblots for Gag were probed with primary polyclonal anti-p24 rabbit serum and secondary goat anti-rabbit IgG-HRP (Santa Cruz), while dgp41 blots were probed with primary human anti-gp41 2F5 (AIDS Reagents Program) and secondary goat anti-human IgG-HRP (Sigma). Coomassie staining was performed to ensure equal protein loading for each lane.

To quantify expression over time, ImageJ software (Schneider et al., 2012) was used to measure band density. For each replicate, the peak day (highest density) for Gag and dgp41 was identified and other day band densities expressed as a percentage of the peak day.

iii. Optimization of VLP Purification

Two strategies for removing rubisco from VLP preparations were tested. In the first experiment, flash-frozen leaf tissue harvested on peak expression day was homogenized in a blender in extraction buffer (25 mM sodium phosphate, 100 mM NaCl, 1 mM EDTA, 50 mM sodium ascorbate, 1 mM PMSF, pH 7.8), strained through miracloth, and insoluble protein was removed by centrifugation at 14,000×g for 20 min at 4° C. The supernatant was collected and subjected to sequential ammonium sulfate precipitation at 20% followed by 40% with VLPs pelleted at 36,000×g for 30 min at 4° C. between fractions. To remove rubisco using pH changes, after pelleting insoluble proteins, the supernatant was titrated to a pH of 5.5 to pellet rubisco followed by adjustment to pH 5.0. After each pH change protein was pelleted at 36,000×g for 30 min at 4° C. The remaining pH 5.0 supernatant was subjected to a 40% ammonium sulfate precipitation to pellet all remaining VLPs and rubisco. All pellets were resuspended in 1×PBS (140 mM NaCl, 2 mM KCl, 10 mM Na2HPO4, 1 mM KH2PO4, pH 7.4). Samples were analyzed via Bradford assay and protein loaded equally into each lane for Coomassie and SDS-PAGE as above.

iv. Large-Scale VLP Production and Purification

Six-week old *N. benthamiana* plants were infiltrated at OD600=0.1 with each of the four vectors. At peak expression day, as determined by the kinetics time course, leaf material was harvested in 20 g batches and flash frozen in liquid nitrogen and stored at −80° C. until extraction. VLPs were purified using 20% ammonium sulfate precipitation described above. Following precipitation VLPs were resuspended in 1×PBS and separated via iodixanol density gradient as previously described (Kessans et al., 2013). Purification progress was monitored by immunoblot by loading 5 µg total soluble protein (TSP) per lane for each step of the extraction and density gradient. Gels were used for Coomassie staining, Gag expression, or dgp41 expression as described above and in (Kessans et al., 2013).

v. VLP Quantification

VLP-containing fractions were concentrated on a 300 kDa molecular weight cut-off membrane (Sartorius) and quantified via immunoblot for total Gag and dgp41 content as previously described (Kessans et al., 2016). Ammonium sulfate pellets were directly quantified without concentrating each sample. Briefly, µg/mL amounts for both proteins were calculated by comparing serial dilutions of concentrated VLP gradient fractions and ammonium sulfate pellets to known concentrations of purified p24-CTA2 or CTB-MPER using ImageJ software to determine band density (Schneider et al., 2012). The total calculated p24 and MPER protein amount was then divided by kilograms of fresh leaf weight (FW) to determine µg/kg yield for Gag and dgp41. Molar ratio of MPER to p24 was determined by relative protein sizes (MPER=15 kDa; p24=24 kDa) for a molecular weight ratio of 1.6 p24 to MPER.

vi. Mouse Immunizations

All animal studies were conducted under the approval of the Arizona State University Institutional Animal Care and Use Committee under protocol number 15-1386R. Four to six-week old C57BL/6 mice (Jackson Laboratories; n=3) were injected i.p. with 2 µg p24 and 1.2 µg MPER gradient-purified VLPs mixed with Ribi adjuvant (Sigma) per manufacturer's protocol. Serum was collected every 2 weeks for analysis of p24 and MPER-specific IgG by ELISA as previously described (Kessans et al., 2016). Results are reported as OD 490 nm over time for the 1:50 dilution (lowest dilution tested).

b. Construction of Transient Geminivirus Vectors

The development of tobacco mosaic virus (TMV)-based vectors—known as MagnICON vectors—for transgene expression in plants has been extensively described (Marillonnet et al., 2004; Gleba et al., 2005; Marillonnet et al., 2005). A TMV vector for transiently expressing dgp41 for making HIV-1 VLPs (referred herein as TMV) was previously described (Kessans et al., 2013) (FIG. 8a). Two Geminivirus vectors (referred herein as Gemini and Gemini+p19) were cloned to transiently express dgp41 with or without the silencing suppressor protein p19 (FIGS. 8b-8c). Geminiviruses are known to induce gene silencing both during natural infection and with expression of transgenes (Seemanpillai et al., 2003; Rodriguez-Negrete et al., 2009; Aregger et al., 2012). The p19 protein has been shown to increase expression of recombinant proteins in plants by preventing gene silencing, thus the inclusion in transient expression vectors is hypothesized to increase yield (Voinnet et al., 2003; Garabagi et al., 2012). A third Geminivirus vector (referred herein as Dual Gemini+p19), and the last tested in this study, was designed to co-express Gag and dgp41 from the same T-DNA fragment, but in separate Geminivirus replicons separated by short and long intergenic regions (LIR/SIR) (FIG. 8d). These replicons are amplified by the replication proteins C1/C2 in the nucleus after *Agrobacterium*-mediated T-DNA transfer (Gutierrez, 1999; Mor et al., 2003; Huang et al., 2009). Expression in all Geminivirus vectors is under control of the Cauliflower mosaic virus (CMV) 35S promoter with two enhancer (2e) binding sites to improve translation efficiency.

c. Geminivirus Vectors Display Accelerated Expression

Following their introduction into *Agrobacterium tumefaciens* cells, agroinfiltration was used to introduce the four vectors were infiltrated into six-week old *Nicotiana benthamiana* plants and expression kinetics was analyzed over the course of seven days. Three of the vectors (TMV, Gemini, and Gemini+p19) were infiltrated into Gag transgenic plants to transiently express dgp41 for VLP production while the fourth vector (Dual Gemini+p19) was infiltrated into wild-type (WT) plants for transient co-expression of Gag and dgp41. Triplicate leaf samples were collected and monitored for necrosis over seven days (FIG. 9). All Geminivirus-based vectors display necrosis earlier than the TMV vector (3-4 days post infection [dpi] vs. 6 dpi). The inclusion of p19 with Geminivirus vectors appears to delay the onset of necrosis by 1-2 days. However, all Geminivirus infiltrated plants had severe necrosis at 7 dpi that prevented further sampling.

Quantitative analysis of Gag and dgp41 expression reveals distinct differences between TMV and Geminivirus vectors (FIGS. 10a-10b). Gemini and Gemini+p19 vectors display a gradual decrease in transgenic Gag levels over the seven days and including p19 in the vectors reduced this decrease by 26.5% on average after 2 dpi (FIGS. 10a, 14b, and 14c, compare red squares with green triangles). In some aspects, Gag level is increased due to reduced gene silencing leading to a decrease in necrosis. The TMV vector maintains steady levels in Gag expression with variability across plants and no clear peak day (FIGS. 10a and 14a, blue circles). Transient expression of Gag by the Dual Gemini+p19 vector shows a clear peak at 2 dpi followed by a steady decline with little to no expression after 4 dpi (FIGS. 10a and 14d), correlating with onset of necrosis (FIG. 9).

Transient expression of dgp41 in the TMV vector shows initial expression at 3 dpi with a steady increase over time peaking at 7 dpi (FIGS. 10b and 14a). The Gemini and Gemini+19 vectors drove expression much earlier with significant accumulation already at 2 dpi with peak expression between 2 and 4 dpi (FIGS. 10b, 14b, and 14c). Interestingly, there is a decrease in dgp41 expression in both vectors at 5 dpi despite equivalent protein loading into the gels (FIGS. 13a-13d) and this is far more drastic in the vector without p19. Dual Gemini +p19 initiates detectable expression at 2 dpi with a steady decline similar to that seen with Gag expression by the same vector (FIGS. 10b and 14d). Based on the combined necrosis and Gag/dgp41 expression levels during the time course, peak expression day was determined to be 4 dpi for TMV and 2-3 dpi for all Gemini vectors.

d. Removal of Rubisco in VLP Preparations

Two strategies were employed in an effort to reduce rubisco in VLP preparations. Rubisco bands were detected by Coomassie, staining for large bands around 50 and 25 kDa corresponding to the large and small subunits of rubisco, respectively. Gag (55 kDa) and dgp41 (23 kDa) were detected by western blot. A majority of VLPs were found to pellet with addition of 20% ammonium sulfate as determined by Gag and dgp41 presence (FIG. 4b-c, 20% P) while the major rubisco band around 50 kDa remains in the 20% supernatant (SN) (FIG. 11a). The rubisco can be precipitated with further increase to 40% ammonium sulfate (FIG. 4a, 40% P) along with any remaining Gag/dgp41 VLPs (FIGS. 11b and 11c). The second strategy utilized pH changes where a majority of the VLPs pellet at pH 5.5 and a further reduction to pH 5.0 did not result in detection of Gag or dgp41 (FIGS. 11b and 11c, pH 5.5 & 5.0 P). Ammonium sulfate was added to a concentration of 40% in the remaining pH 5.0 SN and a large band around 50 kDa was visible in the Coomassie with no detectable Gag and little dgp41, indicating this likely represents a majority of the rubisco (FIGS. 11a-11c, 5.0-40% P). Based on these data, the 20% ammonium sulfate precipitation appears cleaner with fewer protein contaminants, including rubisco, and was therefore chosen as the method of purification for subsequent experiments.

e. VLP Purification and Yield

Large-scale purifications were performed for each of the four vectors harvesting at peak expression day and processing in 20 g batches. VLPs for all samples were primarily isolated to the 20% Optiprep fraction with some large aggregates accumulating in the 50% fraction (FIGS. 12a-12d). Comparison of Gag and dgp41 band intensity on equivalently loaded gels indicates that Gemini +p19 and Dual Gemini +p19 vectors qualitatively have the highest yield of both Gag and dgp41 (FIGS. 12c and 12d). After running density gradients, both the 20% ammonium sulfate pellets and the 20% Optiprep gradient fractions were quantified by immunoblot as previously described (Kessans et al., 2016).

Total expression of Gag reached a maximum around 1 mg/kg fresh leaf weight for both Dual Gemini +p19 transient expression and with the TMV vector in stable transgenics (Table 1). Transient expression of Gag and dgp41 was lowest in the Gemini vector without p19 at 0.62 mg/kg and 0.82 mg/kg, respectively (Table 1). The highest transient dgp41 expression was seen with the Dual Gemini +p19 at 5.5 mg/kg (Table 1). Both Geminivirus vectors which include p19 had higher dgp41 expression than the TMV-based vector. Interestingly, though the Gag yield in the VLP gradient fraction was similar for the TMV and Dual Gemini +p19, but the TMV vector had lower dgp41 yield (Table 2). A similar phenomenon was seen with the Gemini ±p19 vectors where inclusion of p19 during expression resulted in an increase in dgp41 yield within the VLP fraction (Table 2). Furthermore, the higher dgp41 expression in both the Gemini +p19 and Dual Gemini +p19 vectors corresponds to a higher molar ratio of MPER:p24 with an average of 2.8 and 3.3, respectively (Table 2). This indicates more dgp41 per Gag in each VLP particle, thus presenting a better immunogen with more neutralization targets.

TABLE 1

Total Gag and dgp41 expression from ammonium sulfate precipitation.

| Vector | Infiltrated Plant Line | Transient Expression | Gag Yield (mg p24/kg) | dgp41 Yield (mg MPER/kg) |
|---|---|---|---|---|
| TMV | | | 1.04 ± 0.59 | 3.45 ± 2.29 |
| Gemini | Gag | dgp41 | 0.62 ± 0.16 | 0.82 ± 0.52 |
| Gemini (+p19) | | | 0.85 ± 0.34 | 4.62 ± 1.52 |
| Dual Gem. (+p19) | WT | Gag & dgp41 | 1.09 ± 0.38 | 5.46 ± 1.49 |

Protein expression is expressed as mg of p24 or MPER per kg fresh leaf weight for Gag and dgp41, respectively. Triplicate samples were processed for each vector and reported here as mean with standard error.

TABLE 2

HIV VLP yield with transient expression in *N. benthamiana*.

| Vector | Infiltrated Plant Line | Transient Expression | Gag Yield (μg p24/kg) | dgp41 Yield (μg MPER/kg) | MPER:p24 (molar) |
|---|---|---|---|---|---|
| TMV | | | 343 ± 131 | 33 ± 16 | 0.74-5.2 |
| Gemini | Gag | dgp41 | 175 ± 68 | 11 ± 3 | 0.47-1.34 |
| Gemini (+p19) | | | 130 ± 30 | 57 ± 37 | 0.61-9.8 |
| Dual Gem. (+p19) | WT | Gag & dgp41 | 322 ± 92 | 84 ± 38 | 1.7-11.8 |

Levels of protein are expressed as μg p24 or MPER for Gag and dgp41, respectively, per kg fresh leaf weight. Gag and dgp41 yield were determined in triplicate by quantitative immunoblot from density gradient VLP-enriched fractions and reported here as mean with standard error. Molar ratio of MPER to p24 is calculated as amount of dgp41 MPER to p24 Gag based on molecular weight ratio of 1.6 (p24=24 kDa/MPER=15 kDa).

f. VLPs Elicit Gag and Dgp41-Specific Antibodies in Mice

C57BL/6 mice were immunized with Gag/dgp41 VLPs produced using the TMV-based vector at Day 0 and 45. Two weeks after the first dose, p24-specific IgG is detectable in the serum while MPER-specific antibodies were below detection limit (FIG. 13). On week after the second immunization, a 100% response rate was observed for both p24- and MPER-specific serum IgG. This indicates the plant-produced VLPs are immunogenic in mice and can elicit antibodies specific to the MPER bnAb target in the dgp41 protein.

REFERENCES CITED

Alam S M, McAdams M, Boren D, Rak M, Scearce R M, Gao F, Camacho Z T, Gewirth D, Kelsoe G, Chen P, Haynes B F. The role of antibody polyspecificity and lipid reactivity in binding of broadly neutralizing anti-HIV-1 envelope human monoclonal antibodies 2F5 and 4E10 to glycoprotein 41 membrane proximal envelope epitopes. J Immunol. 2007; 178:4424-4435. [PubMed: 17372000]

Alam S M, Morelli M, Dennison S M, Liao H X, Zhang R, Xia S M, Rits-Volloch S, Sun L, Harrison S C, Haynes B F, Chen B. Role of HIV membrane in neutralization by two broadly neutralizing antibodies. Proc Natl Acad Sci USA. 2009; 106:20234-20239. [PubMed: 19906992]

Aregger M, Borah B K, Seguin J, Rajeswaran R, Gubaeva E G, Zvereva A S, Windels D, Vazquez F, Blevins T, Farinelli L, Pooggin M M (2012) Primary and secondary siRNAs in geminivirus-induced gene silencing. PLoS Pathog 8: e1002941

Arfi Z A, Hellwig S, Drossard J, Fischer R, Buyel J F (2016) Polyclonal antibodies for specific detection of tobacco host cell proteins can be efficiently generated following RuBisCO depletion and the removal of endotoxins. Biotechnol J 11: 507-518

Baba T W, Liska V, Hofmann-Lehmann R, Vlasak J, Xu W, Ayehunie S, Cavacini L A, Posner M R, Katinger H, Stiegler G, Bernacky B J, Rizvi T A, Schmidt R, Hill L R, Keeling M E, Lu Y, Wright J E, Chou T C, Ruprecht R M. Human neutralizing monoclonal antibodies of the IgG1 subtype protect against mucosal simian-human immunodeficiency virus infection. Nat Med. 2000; 6:200-206. [PubMed: 10655110]

Bessa J, Zabel F, Link A, Jegerlehner A, Hinton H, Schmitz N, Bauer M, Kundig T M, Saudan P, Bachmann M F (2012) Low-affinity B cells transport viral particles from the lung to the spleen to initiate antibody responses. Proc Natl Acad Sci USA 109: 20566-20571

Betts M R, Nason M C, West S M, De Rosa S C, Migueles S A, Abraham J, Lederman M M, Benito J M, Goepfert P A, Connors M, Roederer M, Koup R A. HIV nonprogressors preferentially maintain highly functional HIV-specific CD8+ T cells. Blood. 2006; 107:4781-4789. [PubMed: 16467198]

Billington J, Hickling T P, Munro G H, Halai C, Chung R, Dodson G G, Daniels R S. Stability of a receptor-binding active human immunodeficiency virus type 1 recombinant gp140 trimer conferred by intermonomer disulfide bonding of the V3 loop: differential effects of protein disulfide isomerase on CD4 and coreceptor binding. J Virol. 2007; 81:4604-4614. [PubMed: 17301129]

Bomsel M, Tudor D, Drillet A S, Alfsen A, Ganor Y, Roger M G, Mouz N, Amacker M, Chalifour A, Diomede L, Devillier G, Cong Z, Wei Q, Gao H, Qin C, Yang G B, Zurbriggen R, Lopalco L, Fleury S. Immunization with HIV-1 gp41 subunit virosomes induces mucosal antibodies protecting nonhuman primates against vaginal SHIV challenges. Immunity. 2011; 34:269-280. [PubMed: 21315623]

Bonsignori M, Alam S M, Liao H X, Verkoczy L, Tomaras G D, Haynes B F, Moody M A. HIV-1 antibodies from infection and vaccination: insights for guiding vaccine design. Trends Microbiol. 2012; 20:532-539. [PubMed: 22981828]

Brander C, Walker B D. T lymphocyte responses in HIV-1 infection: implications for vaccine development. Curr Opin Immunol. 1999; 11:451-459. [PubMed: 10448136]

Brandt T A, Jacobs B L. Both carboxy- and amino-terminal domains of the vaccinia virus interferon resistance gene, E3L, are required for pathogenesis in a mouse model. J Virol. 2001; 75:850-856. [PubMed: 11134298]

Briggs J A, Krausslich H G (2011) The molecular architecture of HIV. J Mol Biol 410: 491-500

Buchbinder S P, Mehrotra D V, Duerr A, Fitzgerald D W, Mogg R, Li D, Gilbert P B, Lama J R, Marmor M, Del Rio C, McElrath M J, Casimiro D R, Gottesdiener K M, Chodakewitz J A, Corey L, Robertson M N, Step Study Protocol, T. Efficacy assessment of a cell-mediated immunity HIV-1 vaccine (the Step Study): a double-blind, randomised, placebo-controlled, test-of-concept trial. Lancet. 2008; 372:1881-1893. [PubMed: 19012954]

Burton D R, Mascola J R. Antibody responses to envelope glycoproteins in HIV-1 infection. Nat Immunol. 2015; 16:571-576. [PubMed: 25988889]

Buyel I F, Fischer R (2014) Generic chromatography-based purification strategies accelerate the development of downstream processes for biopharmaceutical proteins produced in plants. Biotechnol J 9: 566-577

Buyel I F, Woo J A, Cramer S M, Fischer R (2013) The use of quantitative structure-activity relationship models to develop optimized processes for the removal of tobacco host cell proteins during biopharmaceutical production. J Chromatogr A 1322: 18-28

Buzon V, Natraj an G, Schibli D, Campelo F, Kozlov M M, Weissenhorn W. Crystal structure of HIV-1 gp41 including both fusion peptide and membrane proximal external regions. PLoS Pathog. 2010; 6:e1000880. [PubMed: 20463810]

Cardoso R M, Zwick M B, Stanfield R L, Kunert R, Binley J M, Katinger H, Burton D R, Wilson I A. Broadly neutralizing anti-HIV antibody 4E10 recognizes a helical conformation of a highly conserved fusion-associated motif in gp41. Immunity. 2005; 22:163-173. [PubMed: 15723805]

Chapman R, Stutz H, Jacobs W Jr, Shephard E, Williamson A L. Priming with recombinant auxotrophic BCG expressing HIV-1 Gag, R T and Gp120 and boosting with recombinant MVA induces a robust T cell response in mice. PLoS One. 2013; 8:e71601. [PubMed: 23977084]

Chege G K, Shephard E G, Meyers A, van Harmelen J, Williamson C, Lynch A, Gray C M, Rybicki E P, Williamson A L. HIV-1 subtype C Pr55gag virus-like particle vaccine efficiently boosts baboons primed with a matched DNA vaccine. J Gen Virol. 2008; 89:2214-2227. [PubMed: 18753231]

Chen J, Frey G, Peng H, Rits-Volloch S, Garrity J, Seaman M S, Chen B. Mechanism of HIV-1 neutralization by antibodies targeting a membrane-proximal region of gp41. J Virol. 2014; 88:1249-1258. [PubMed: 24227838]

Chen Q, Lai H (2013) Plant-derived virus-like particles as vaccines. Human vaccines & immunotherapeutics 9: 26-49

Chen X, Rock M T, Hammonds J, Tartaglia J, Shintani A, Currier J, Slike B, Crowe J E Jr, Marovich M, Spearman P. Pseudovirion particle production by live poxvirus human immunodeficiency virus vaccine vector enhances humoral and cellular immune responses. J Virol. 2005; 79:5537-5547. [PubMed: 15827168]

Chowell D, Krishna S, Becker P D, Cocita C, Shu J, Tan X, Greenberg P D, Klavinskis L S, Blattman J N, Anderson K S. TCR contact residue hydrophobicity is a hallmark of immunogenic CD8+ T cell epitopes. Proc Natl Acad Sci USA. 2015; 112:E1754-E1762. [PubMed: 25831525]

Chung A W, Ghebremichael M, Robinson H, Brown E, Choi I, Lane S, Dugast A S, Schoen M K, Rolland M, Suscovich T J, Mahan A E, Liao L, Streeck H, Andrews C, Rerks-Ngarm S, Nitayaphan S, de Souza M S, Kaewkungwal J, Pitisuttithum P, Francis D, Michael N L, Kim J H, Bailey-Kellogg C, Ackerman M E, Alter G. Polyfunctional Fc-effector profiles mediated by IgG subclass selection distinguish RV144 and VAX003 vaccines. Sci Transl Med. 2014; 6:228ra238.

Corey L, Gilbert P B, Tomaras G D, Haynes B F, Pantaleo G, Fauci A S. Immune correlates of vaccine protection against HIV-1 acquisition. Sci Transl Med. 2015; 7:310rv317.

Crooks E T, Tong T, Chakrabarti B, Narayan K, Georgiev I S, Menis S, Huang X, Kulp D, Osawa K, Muranaka J, Stewart-Jones G, Destefano J, O'Dell S, LaBranche C, Robinson J E, Montefiori D C, McKee K, Du S X, Doria-Rose N, Kwong P D, Mascola J R, Zhu P, Schief W R, Wyatt R T, Whalen R G, Binley J M. Vaccine-elicited tier 2 HIV-1 neutralizing antibodies bind to quaternary epitopes involving glycan-deficient patches proximal to the CD4 binding site. PLoS Pathog. 2015; 11:e1004932. [PubMed: 26023780]

Daniell H, Singh N D, Mason H, Streatfield S J (2009) Plant-made vaccine antigens and biopharmaceuticals. Trends Plant Sci 14: 669-679

Davis K L, Gray E S, Moore P L, Decker J M, Salomon A, Montefiori D C, Graham B S, Keefer M C, Pinter A, Morris L, Hahn B H, Shaw G M. High titer HIV-1 V3-specific antibodies with broad reactivity but low neutralizing potency in acute infection and following vaccination. Virology. 2009; 387:414-426. [PubMed: 19298995]

Decker J M, Bibollet-Ruche F, Wei X, Wang S, Levy D N, Wang W, Delaporte E, Peeters M, Derdeyn C A, Allen S, Hunter E, Saag M S, Hoxie J A, Hahn B H, Kwong P D, Robinson J E, Shaw G M. Antigenic conservation and immunogenicity of the HIV coreceptor binding site. J Exp Med. 2005; 201:1407-1419. [PubMed: 15867093]

Devito C, Broliden K, Kaul R, Svensson L, Johansen K, Kiama P, Kimani J, Lopalco L, Piconi S, Bwayo J J, Plummer F, Clerici M, Hinkula J. Mucosal and plasma IgA from HIV-1-exposed uninfected individuals inhibit HIV-1 transcytosis across human epithelial cells. J Immunol. 2000b; 165:5170-5176. [PubMed: 11046049]

Devito C, Hinkula J, Kaul R, Lopalco L, Bwayo J J, Plummer F, Clerici M, Broliden K. Mucosal and plasma IgA from HIV-exposed seronegative individuals neutralize a primary HIV-1 isolate. AIDS. 2000a; 14:1917-1920. [PubMed: 10997395]

Diomede L, Nyoka S, Pastori C, Scotti L, Zambon A, Sherman G, Gray C M, Sarzotti-Kelsoe M, Lopalco L. Passively transmitted gp41 antibodies in babies born from HIV-1 subtype C-seropositive women: correlation between fine specificity and protection. J Virol. 2012; 86:4129-4138. [PubMed: 22301151]

Du S X, Idiart R J, Mariano E B, Chen H, Jiang P, Xu L, Ostrow K M, Wrin T, Phung P, Binley J M, Petropoulos C J, Ballantyne J A, Whalen R G. Effect of trimerization motifs on quaternary structure, antigenicity, and immunogenicity of a noncleavable HIV-1 gp140 envelope glycoprotein. Virology. 2009; 395:33-44. [PubMed: 19815247]

Duprez L, Wirawan E, Vanden Berghe T, Vandenabeele P. Major cell death pathways at a glance. Microbes Infect. 2009; 11:1050-1062. [PubMed: 19733681]

Egelkrout E, Raj an V, Howard J A (2012) Overproduction of recombinant proteins in plants. Plant Sci 184: 83-101

Feller U, Anders I, Mae T (2008) Rubiscolytics: fate of Rubisco after its enzymatic function in a cell is terminated. J Exp Bot 59: 1615-1624

Fischer R, Schillberg S, Hellwig S, Twyman R M, Drossard J (2012) GMP issues for recombinant plant-derived pharmaceutical proteins. Biotechnol Adv 30: 434-439

Frey G, Chen J, Rits-Volloch S, Freeman M M, Zolla-Pazner S, Chen B. Distinct conformational states of HIV-1 gp41 are recognized by neutralizing and non-neutralizing antibodies. Nat Struct Mol Biol. 2010; 17:1486-1491. [PubMed: 21076402]

Frey G, Peng H, Rits-Volloch S, Morelli M, Cheng Y, Chen B. A fusion-intermediate state of HIV-1 gp41 targeted by broadly neutralizing antibodies. Proc Natl Acad Sci USA. 2008; 105:3739-3744. [PubMed: 18322015]

Garabagi F, Gilbert E, Loos A, McLean M D, Hall J C (2012) Utility of the P19 suppressor of gene-silencing protein for production of therapeutic antibodies in *Nicotiana* expression hosts. Plant Biotechnol J 10: 1118-1128

Garcia F, Bernaldo de Quiros J C, Gomez C E, Perdiguero B, Najera J L, Jimenez V, Garcia-Arriaza J, Guardo A C, Perez I, Diaz-Brito V, Conde M S, Gonzalez N, Alvarez A, Alcami J, Jimenez J L, Pich J, Arnaiz J A, Maleno M J, Leon A, Munoz-Fernandez M A, Liljestrom P, Weber J, Pantaleo G, Gatell J M, Plana M, Esteban M. Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: a phase I clinical trial (RISVAC02). Vaccine. 2011; 29:8309-8316. [PubMed: 21907749]

Garcia-Arriaza J, Arnaez P, Gomez C E, Sorzano C O, Esteban M. Improving adaptive and memory immune responses of an HIV/AIDS vaccine candidate MVA-B by deletion of vaccinia virus genes (C6L and K7R) blocking interferon signaling pathways. PLoS One. 2013; 8:e66894. [PubMed: 23826170]

Garcia-Arriaza J, Najera J L, Gomez C E, Tewabe N, Sorzano C O, Calandra T, Roger T, Esteban M. A candidate HIV/AIDS vaccine (MVA-B) lacking vaccinia virus gene C6L enhances memory HW-1-specific T-cell responses. PLoS One. 2011; 6:e24244. [PubMed: 21909386]

Garoff H, Hewson R, Opstelten D J. Virus maturation by budding. Microbiol Mol Biol Rev. 1998; 62:1171-1190. [PubMed: 9841669]

GlaxoSmithKline I. Product Monograph—Cervarix. 2014

Gleba Y, Klimyuk V, Marillonnet S (2005) Magnifection—a new platform for expressing recombinant vaccines in plants. Vaccine 23: 2042-2048

Goepfert P A, Elizaga M L, Sato A, Qin L, Cardinali M, Hay C M, Hural J, DeRosa S C, DeFawe O D, Tomaras G D, Montefiori D C, Xu Y, Lai L, Kalams S A, Baden L R, Frey S E, Blattner W A, Wyatt L S, Moss B, Robinson H L, National Institute of A, Infectious Diseases HIVVTN. Phase 1 safety and immunogenicity testing of DNA and recombinant modified vaccinia Ankara vaccines expressing HIV-1 virus-like particles. J Infect Dis. 2011; 203: 610-619. [PubMed: 21282192]

Gomez C E, Najera J L, Jimenez E P, Jimenez V, Wagner R, Graf M, Frachette M J, Liljestrom P, Pantaleo G, Esteban M. Head-to-head comparison on the immunogenicity of two HIV/AIDS vaccine candidates based on the attenuated poxvirus strains MVA and NYVAC co-expressing in a single locus the HIV-1BX08 gp120 and HIV-1 (M B) Gag-Pol-Nef proteins of clade B. Vaccine. 2007; 25:2863-2885. [PubMed: 17113200]

Gomez C E, Perdiguero B, Garcia-Arriaza J, Esteban M. Poxvirus vectors as HIV/AIDS vaccines in humans. Hum Vaccin Immunother. 2012a; 8:1192-1207. [PubMed: 22906946]

Gomez C E, Perdiguero B, Najera J L, Sorzano C O, Jimenez V, Gonzalez-Sanz R, Esteban M. Removal of vaccinia virus genes that block interferon type I and II pathways improves adaptive and memory responses of the HIV/AIDS vaccine candidate NYVAC-C in mice. J Virol. 2012b; 86:5026-5038. [PubMed: 22419805]

Gong Z, Martin-Garcia J M, Daskalova S M, Craciunescu F M, Song L, Dorner K, Hansen D T, Yang J H, LaBaer J, Hogue B G, Mor T S, Fromme P. Biophysical characterization of a vaccine candidate against HIV-1: the transmembrane and membrane proximal domains of HIV-1 gp41 as a maltose binding protein fusion. PLoS One. 2015; 10:e0136507. [PubMed: 26295457]

Goulder P J, Watkins D I. HIV and SIV CTL escape: implications for vaccine design. Nat Rev Immunol. 2004; 4:630-640. [PubMed: 15286729]

Greseth M D, Traktman P. De novo fatty acid biosynthesis contributes significantly to establishment of a bioenergetically favorable environment for vaccinia virus infection. PLoS Pathog. 2014; 10:e1004021. [PubMed: 24651651]

Gutierrez C (1999) Geminivirus DNA replication. Cellular and Molecular Life Sciences 56: 313-329

Hansen S G, Piatak M Jr, Ventura A B, Hughes C M, Gilbride R M, Ford J C, Oswald K, Shoemaker R, Li Y, Lewis M S, Gilliam A N, Xu G, Whizin N, Burwitz B J, Planer S L, Turner J M, Legasse A W, Axthelm M K, Nelson J A, Fruh K, Sacha J B, Estes J D, Keele B F, Edlefsen P T, Lifson J D, Picker L J. Immune clearance of highly pathogenic SIV infection. Nature. 2013a; 502:100-104. [PubMed: 24025770]

Hansen S G, Sacha J B, Hughes C M, Ford J C, Burwitz B J, Scholz I, Gilbride R M, Lewis M S, Gilliam A N, Ventura A B, Malouli D, Xu G, Richards R, Whizin N, Reed J S, Hammond K B, Fischer M, Turner J M, Legasse A W, Axthelm M K, Edlefsen P T, Nelson J A, Lifson J D, Fruh K, Picker L J. Cytomegalovirus vectors violate CD8+ T cell epitope recognition paradigms. Science. 2013b; 340:1237874. [PubMed: 23704576]

Harari A, Bart P A, Stohr W, Tapia G, Garcia M, Medjitna-Rais E, Burnet S, Cellerai C, Erlwein O, Barber T, Moog C, Liljestrom P, Wagner R, Wolf H, Kraehenbuhl J P, Esteban M, Heeney J, Frachette M J, Tartaglia J, McCormack S, Babiker A, Weber J, Pantaleo G. An HIV-1 clade C DNA prime, NYVAC boost vaccine regimen induces reliable, polyfunctional, and long-lasting T cell responses. J Exp Med. 2008; 205:63-77. [PubMed: 18195071]

Harari A, Rozot V, Cavassini M, Bellutti Enders F, Vigano S, Tapia G, Castro E, Burnet S, Lange J, Moog C, Garin D, Costagliola D, Autran B, Pantaleo G, Bart P A. NYVAC immunization induces polyfunctional HIV-specific T-cell responses in chronically-infected, ART-treated HIV patients. Eur J Immunol. 2012; 42:3038-3048. [PubMed: 22930439]

Haynes B F, Fleming J, St Clair E W, Katinger H, Stiegler G, Kunert R, Robinson J, Scearce R M, Plonk K, Staats H F, Ortel T L, Liao H X, Alam S M. Cardiolipin polyspecific autoreactivity in two broadly neutralizing HIV-1 antibodies. Science. 2005; 308:1906-1908. [PubMed: 15860590]

Haynes B F, Gilbert P B, McElrath M J, Zolla-Pazner S, Tomaras G D, Alam S M, Evans D T, Montefiori D C, Karnasuta C, Sutthent R, Liao H X, DeVico A L, Lewis G K, Williams C, Pinter A, Fong Y, Janes H, DeCamp A, Huang Y, Rao M, Billings E, Karasavvas N, Robb M L, Ngauy V, de Souza M S, Paris R, Ferrari G, Bailer R T, Soderberg K A, Andrews C, Berman P W, Frahm N, De Rosa S C, Alpert M D, Yates N L, Shen X, Koup R A, Pitisuttithum P, Kaewkungwal J, Nitayaphan S, Rerks-Ngarm S, Michael N L, Kim J H. Immune-correlates analysis of an HIV-1 vaccine efficacy trial. N Engl J Med. 2012; 366:1275-1286. [PubMed: 22475592]

Haynes B F, Shaw G M, Korber B, Kelsoe G, Sodroski J, Hahn B H, Borrow P, McMichael A J. HIV-host interactions: implications for vaccine design. Cell Host Microbe. 2016; 19:292-303. [PubMed: 26922989]

Hessell A J, Hangartner L, Hunter M, Havenith C E, Beurskens F J, Bakker J M, Lanigan C M, Landucci G, Forthal D N, Parren P W, Marx P A, Burton D R. Fc receptor but not complement binding is important in antibody protection against HIV. Nature. 2007; 449:101-104. [PubMed: 17805298]

Hessell A J, Rakasz E G, Tehrani D M, Huber M, Weisgrau K L, Landucci G, Forthal D N, Koff W C, Poignard P, Watkins D I, Burton D R. Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L. J Virol. 2010; 84:1302-1313. [PubMed: 19906907]

Hoot S, McGuire A T, Cohen K W, Strong R K, Hangartner L, Klein F, Diskin R, Scheid J F, Sather D N, Burton D R, Stamatatos L. Recombinant HIV envelope proteins fail to engage germline versions of anti-CD4bs bNAbs. PLoS Pathog. 2013; 9:e1003106. [PubMed: 23300456]

Horn M E, Pappu K M, Bailey M R, Clough R C, Barker M, Jilka J M, Howard J A, Streatfield S J (2003) Advantageous features of plant-based systems for the development of HIV vaccines. J Drug Target 11: 539-545

Huang J, Kang B H, Pancera M, Lee J H, Tong T, Feng Y, Imamichi H, Georgiev I S, Chuang G Y, Druz A, Doria-Rose N A, Laub L, Sliepen K, van Gils M J, de la Pena A T, Derking R, Klasse P J, Migueles S A, Bailer R T, Alam M, Pugach P, Haynes B F, Wyatt R T, Sanders R W, Binley J M, Ward A B, Mascola J R, Kwong P D, Connors M. Broad and potent HIV-1 neutralization by a human antibody that binds the gp41-gp120 interface. Nature. 2014; 515:138-142. [PubMed: 25186731]

Huang J, Ofek G, Laub L, Louder M K, Doria-Rose N A, Longo N S, Imamichi H, Bailer R T, Chakrabarti B, Sharma S K, Alam S M, Wang T, Yang Y, Zhang B, Migueles S A, Wyatt R, Haynes B F, Kwong P D, Mascola J R, Connors M. Broad and potent neutralization of HIV-1 by a gp41-specific human antibody. Nature. 2012; 491: 406-412. [PubMed: 23151583]

Huang Y, Follmann D, Nason M, Zhang L, Huang Y, Mehrotra D V, Moodie Z, Metch B, Janes H, Keefer M C, Churchyard G, Robb M L, Fast P E, Duerr A, McElrath M J, Corey L, Mascola J R, Graham B S, Sobieszczyk M E, Kublin J G, Robertson M, Hammer S M, Gray G E, Buchbinder S P, Gilbert P B. Effect of rAd5-vector HIV-1 preventive vaccines on HIV-1 acquisition: a participant-level meta-analysis of randomized trials. PLoS One. 2015; 10:e0136626. [PubMed: 26332672]

Huang Z, Chen Q, Hjelm B, Arntzen C, Mason H (2009) A DNA replicon system for rapid high-level production of virus-like particles in plants. Biotechnology and bioengineering 103: 706-714

Irimia A, Sarkar A, Stanfield R L, Wilson I A. Crystallographic identification of lipid as an integral component of the epitope of HIV broadly neutralizing antibody 4E10. Immunity. 2016; 44:21-31. [PubMed: 26777395]

Jacob R A, Moyo T, Schomaker M, Abrahams F, Grau Pujol B, Dorfman J R. Anti-V3/glycan and Anti-MPER neutralizing antibodies, but not anti-V2/glycan site antibodies, are strongly associated with greater anti-HIV-1 neutralization breadth and potency. J Virol. 2015; 89:5264-5275. [PubMed: 25673728]

Jacobs B L, Langland J O, Kibler K V, Denzler K L, White S D, Holechek S A, Wong S, Huynh T, Baskin C R. Vaccinia virus vaccines: past, present and future. Antivir Res. 2009; 84:1-13. [PubMed: 19563829]

Jardine J, Julien J P, Menis S, Ota T, Kalyuzhniy O, McGuire A, Sok D, Huang P S, MacPherson S, Jones M, Nieusma T, Mathison J, Baker D, Ward A B, Burton D R, Stamatatos L, Nemazee D, Wilson I A, Schief W R. Rational HIV immunogen design to target specific germline B cell receptors. Science. 2013; 340:711-716. [PubMed: 23539181]

Jiao Y, Xie J, L T, Han Y, Qiu Z, Zuo L, Wang A. Correlation between gag-specific CD8 T-cell responses, viral load, and CD4 count in HIV-1 infection is dependent on disease status. J Acquir Immune Defic Syndr. 2006; 42:263-268. [PubMed: 16763520]

Kaul R, Plummer F, Clerici M, Bomsel M, Lopalco L, Broliden K. Mucosal IgA in exposed, uninfected subjects: evidence for a role in protection against HIV infection. AIDS. 2001; 15:431-432. [PubMed: 11273233]

Kaul R, Trabattoni D, Bwayo J J, Arienti D, Zagliani A, Mwangi F M, Kariuki C, Ngugi E N, MacDonald K S, Ball T B, Clerici M, Plummer F A. HIV-1-specific mucosal IgA in a cohort of HIV-1-resistant Kenyan sex workers. AIDS. 1999; 13:23-29. [PubMed: 10207541]

Keefer M C, Frey S E, Elizaga M, Metch B, De Rosa S C, Barroso P F, Tomaras G, Cardinali M, Goepfert P, Kalichman A, Philippon V, McElrath M J, Jin X, Ferrari G, Defawe O D, Mazzara G P, Montefiori D, Pensiero M, Panicali D L, Corey L, Network NHVT. A phase I trial of preventive HIV vaccination with heterologous poxviral-vectors containing matching HIV-1 inserts in healthy HIV-uninfected subjects. Vaccine. 2011; 29:1948-1958. [PubMed: 21216311]

Kepler T B, Liao H X, Alam S M, Bhaskarabhatla R, Zhang R, Yandava C, Stewart S, Anasti K, Kelsoe G, Parks R, Lloyd K E, Stolarchuk C, Pritchett J, Solomon E, Friberg E, Morris L, Karim S S, Cohen M S, Walter E, Moody M A, Wu X, Altae-Tran H R, Georgiev I S, Kwong P D, Boyd S D, Fire A Z, Mascola J R, Haynes B F. Immunoglobulin gene insertions and deletions in the affinity maturation of HIV-1 broadly reactive neutralizing antibodies. Cell Host Microbe. 2014; 16:304-313. [PubMed: 25211073]

Kessans S A, Linhart M D, Matoba N, Mor T. Biological and biochemical characterization of HIV-1 Gag/dgp41 virus-like particles expressed in *Nicotiana benthamiana*. Plant Biotechnol J. 2013; 11:681-690. [PubMed: 23506331]

Kessans S A, Linhart M D, Meador L R, Kilbourne J, Hogue B G, Fromme P, Matoba N, Mor T S. Immunological characterization of plant-based HIV-1 Gag/Dgp41 virus-like particles. PLoS One. 2016; 11:e0151842. [PubMed: 26986483]

Kibler K V, Gomez C E, Perdiguero B, Wong S, Huynh T, Holechek S, Arndt W, Jimenez V, Gonzalez-Sanz R, Denzler K, Haddad E K, Wagner R, Sekaly R P, Tartaglia J, Pantaleo G, Jacobs B L, Esteban M. Improved NYVAC-based vaccine vectors. PLoS One. 2011; 6:e25674. [PubMed: 22096477]

Kibler K V, Shors T, Perkins K, Zeman C, M P B, Biesterfeldt J, Langland J O, Jacobs B L. Double-stranded RNA is a trigger for apoptosis in vaccinia virus-infected cells. J Virol. 1997; 71:1992-2003. [PubMed: 9032331]

Kiepiela P, Ngumbela K, Thobakgale C, Ramduth D, Honeyborne I, Moodley E, Reddy S, de Pierres C, Mncube Z, Mkhwanazi N, Bishop K, van der Stok M, Nair K, Khan N, Crawford H, Payne R, Leslie A, Prado J, Prendergast A, Frater J, McCarthy N, Brander C, Learn G H, Nickle D, Rousseau C, Coovadia H, Mullins J I, Heckerman D, Walker B D, Goulder P. CD8+ T-cell responses to different HIV proteins have discordant associations with viral load. Nat Med. 2007; 13:46-53. [PubMed: 17173051]

Klein F, Diskin R, Scheid J F, Gaebler C, Mouquet H, Georgiev I S, Pancera M, Zhou T, Incesu R B, Fu B Z, Gnanapragasam P N, Oliveira T Y, Seaman M S, Kwong P D, Bjorkman P J, Nussenzweig M C. Somatic mutations of the immunoglobulin framework are generally required for broad and potent HIV-1 neutralization. Cell. 2013b; 153:126-138. [PubMed: 23540694]

Klein F, Mouquet H, Dosenovic P, Scheid J F, Scharf L, Nussenzweig M C. Antibodies in HIV-1 vaccine development and therapy. Science. 2013a; 341:1199-1204. [PubMed: 24031012]

Koup R A, Safrit J T, Cao Y, Andrews C A, McLeod G, Borkowsky W, Farthing C, Ho D D. Temporal association of cellular immune responses with the initial control of viremia in primary human immunodeficiency virus type 1 syndrome. J Virol. 1994; 68:4650-4655. [PubMed: 8207839]

Kushnir N, Streatfield S J, Yusibov V. Virus-like particles as a highly efficient vaccine platform: diversity of targets and production systems and advances in clinical development. Vaccine. 2012; 31:58-83. [PubMed: 23142589]

Labrijn A F, Poignard P, Raja A, Zwick M B, Delgado K, Franti M, Binley J, Vivona V, Grundner C, Huang C C, Venturi M, Petropoulos C J, Wrin T, Dimitrov D S, Robinson J, Kwong P D, Wyatt R T, Sodroski J, Burton D R. Access of antibody molecules to the conserved coreceptor binding site on glycoprotein gp120 is sterically restricted on primary human immunodeficiency virus type 1. J Virol. 2003; 77:10557-10565. [PubMed: 12970440]

Leroux-Roels G, Maes C, Clement F, van Engelenburg F, van den Dobbelsteen M, Adler M, Amacker M, Lopalco L, Bomsel M, Chalifour A, Fleury S. Randomized phase I: safety, immunogenicity and mucosal antiviral activity in young healthy women vaccinated with HIV-1 Gp41 P1 peptide on virosomes. PloS One. 2013; 8:e55438. [PubMed: 23437055]

Li M X, Dewson G. Mitochondria and apoptosis: emerging concepts. F1000Prime Rep. 2015; 7:42. [PubMed: 26097715]

Liao H X, Bonsignori M, Alam S M, McLellan J S, Tomaras G D, Moody M A, Kozink D M, Hwang K K, Chen X, Tsao C Y, Liu P, Lu X, Parks R J, Montefiori D C, Ferrari G, Pollara J, Rao M, Peachman K K, Santra S, Letvin N L, Karasavvas N, Yang Z Y, Dai K, Pancera M, Gorman J, Wiehe K, Nicely N I, Rerks-Ngarm S, Nitayaphan S, Kaewkungwal J, Pitisuttithum P, Tartaglia J, Sinangil F, Kim J H, Michael N L, Kepler T B, Kwong P D, Mascola J R, Nabel G J, Pinter A, Zolla-Pazner S, Haynes B F. Vaccine induction of antibodies against a structurally heterogeneous site of immune pressure within HIV-1 envelope protein variable regions 1 and 2. Immunity. 2013; 38:176-186. [PubMed: 23313589]

Liao H X, Chen X, Munshaw S, Zhang R, Marshall D J, Vandergrift N, Whitesides J F, Lu X, Yu J S, Hwang K K, Gao F, Markowitz M, Heath S L, Bar K J, Goepfert P A, Montefiori D C, Shaw G C, Alam S M, Margolis D M, Denny T N, Boyd S D, Marshal E, Egholm M, Simen B B, Hanczaruk B, Fire A Z, Voss G, Kelsoe G, Tomaras G D, Moody M A, Kepler T B, Haynes B F. Initial antibodies binding to HIV-1 gp41 in acutely infected subjects are polyreactive and highly mutated. J Exp Med. 2011; 208: 2237-2249. [PubMed: 21987658]

Link A, Zabel F, Schnetzler Y, Titz A, Brombacher F, Bachmann M F (2012) Innate immunity mediates follicular transport of particulate but not soluble protein antigen. Journal of immunology 188: 3724-3733

Ma J K, Chikwamba R, Sparrow P, Fischer R, Mahoney R, Twyman R M (2005) Plant-derived pharmaceuticals—the road forward. Trends Plant Sci 10: 580-585

Magerus-Chatinet A, Yu H, Garcia S, Ducloux E, Terris B, Bomsel M. Galactosyl ceramide expressed on dendritic cells can mediate HIV-1 transfer from monocyte derived dendritic cells to autologous T cells. Virology. 2007; 362:67-74. [PubMed: 17234232]

Marillonnet S, Giritch A, Gils M, Kandzia R, Klimyuk V, Gleba Y (2004) In planta engineering of viral RNA replicons: Efficient assembly by recombination of DNA modules delivered by Agrobacterium. Proceedings of the National Academy of Sciences 101: 6852-6857

Marillonnet S, Thoeringer C, Kandzia R, Klimyuk V, Gleba Y (2005) Systemic Agrobacterium tumefaciens-mediated transfection of viral replicons for efficient transient expression in plants. Nat Biotechnol 23: 718-723

Martinez F O, Gordon S. The M1 and M2 paradigm of macrophage activation: time for reassessment. F1000Prime Rep. 2014; 6:13. [PubMed: 24669294]

Mascola J R, Haynes B F. HIV-1 neutralizing antibodies: understanding nature's pathways. Immunol Rev. 2013; 254:225-244. [PubMed: 23772623]

Mascola J R, Montefiori D C. The role of antibodies in HIV vaccines. Annu Rev Immunol. 2010; 28:413-444. [PubMed: 20192810]

Matoba N, Griffin T A, Mittman M, Doran J D, Alfsen A, Montefiori D C, Hanson C V, Bomsel M, Mor T S. Transcytosis-blocking abs elicited by an oligomeric immunogen based on the membrane proximal region of HIV-1 gp41 target non-neutralizing epitopes. Curr HIV Res. 2008; 6:218-229. [PubMed: 18473785]

Matoba N, Kajiura H, Cherni I, Doran J D, Bomsel M, Fujiyama K, Mor T S. Biochemical and immunological characterization of the plant-derived candidate human immunodeficiency virus type 1 mucosal vaccine CTB-MPR. Plant Biotechnol J. 2009; 7:129-145. [PubMed: 19037902]

Matoba N, Magerus A, Geyer B C, Zhang Y, Muralidharan M, Alfsen A, Arntzen C J, Bomsel M, Mor T S. A mucosally targeted subunit vaccine candidate eliciting HIV-1 transcytosis-blocking Abs. Proc Natl Acad Sci USA. 2004; 101:13584-13589. [PubMed: 15347807]

McGuire A T, Glenn J A, Lippy A, Stamatatos L. Diverse recombinant HIV-1 Envs fail to activate B cells expressing the germline B cell receptors of the broadly neutralizing anti-HIV-1 antibodies PG9 and 447-52D. J Virol. 2014; 88:2645-2657. [PubMed: 24352455]

McMichael A J, Koff W C. Vaccines that stimulate T cell immunity to HIV-1: the next step. Nat Immunol. 2014; 15:319-322. [PubMed: 24646598]

Merck, Co. I. Prescribing Information—Gardasil. 2006

Meyers A, Chakauya E, Shephard E, Tanzer F L, Maclean J, Lynch A, Williamson A L, Rybicki E P (2008) Expression of HIV-1 antigens in plants as potential subunit vaccines. BMC Biotechnol 8: 53

Micoli K J, Mamaeva O, Piller S C, Barker J L, Pan G, Hunter E, McDonald J M. Point mutations in the C-terminus of HIV-1 gp160 reduce apoptosis and calmodulin binding without affecting viral replication. Virology. 2006; 344:468-479. [PubMed: 16229872]

Mooij P, Balla-Jhagjhoorsingh S S, Beenhakker N, van Haaften P, Baak I, Nieuwenhuis I G, Heidari S, Wolf H, Frachette M J, Bieler K, Sheppard N, Harari A, Bart P A, Liljestrom P, Wagner R, Pantaleo G, Heeney J L. Comparison of human and rhesus macaque T-cell responses elicited by boosting with NYVAC encoding human immunodeficiency virus type 1 clade C immunogens. J Virol. 2009; 83:5881-5889. [PubMed: 19321612]

Moore P L, Williamson C, Morris L. Virological features associated with the development of broadly neutralizing antibodies to HIV-1. Trends Microbiol. 2015; 23:204-211. [PubMed: 25572881]

Mor T S, Moon Y, Palmer K E, Mason H S (2003) Geminivirus vectors for high-level expression of foreign proteins in plant cells. Wiley Periodicals Biotechnology and Bioengineering 81: 430-437

Mosser D M, Edwards J P. Exploring the full spectrum of macrophage activation. Nat Rev Immunol. 2008; 8:958-969. [PubMed: 19029990]

Mudd P A, Martins M A, Ericsen A J, Tully D C, Power K A, Bean A T, Piaskowski S M, Duan L, Seese A, Gladden A D, Weisgrau K L, Furlott J R, Kim Y I, Veloso de Santana M G, Rakasz E, Capuano S 3rd, Wilson N A, Bonaldo M C, Galler R, Allison D B, Piatak M Jr, Haase A T, Lifson J D, Allen T M, Watkins D I. Vaccine-induced CD8+ T cells control AIDS virus replication. Nature. 2012; 491:129-133. [PubMed: 23023123]

Nelson J D, Brunel F M, Jensen R, Crooks E T, Cardoso R M, Wang M, Hessell A, Wilson I A, Binley J M, Dawson P E, Burton D R, Zwick M B. An affinity-enhanced neutralizing antibody against the membrane-proximal external region of human immunodeficiency virus type 1 gp41 recognizes an epitope between those of 2F5 and 4E10. J Virol. 2007; 81:4033-4043. [PubMed: 17287272]

Nitayaphan S, Pitisuttithum P, Karnasuta C, Eamsila C, de Souza M, Morgan P, Polonis V, Benenson M, VanCott T, Ratto-Kim S, Kim J, Thapinta D, Garner R, Bussaratid V, Singharaj P, el-Habib R, Gurunathan S, Heyward W, Birx D, McNeil J, Brown A E, Thai AVEG. Safety and immunogenicity of an HIV subtype B and E prime-boost vaccine combination in HIV-negative Thai adults. J Infect Dis. 2004; 190:702-706. [PubMed: 15272397]

Ogg G S, Jin X, Bonhoeffer S, Dunbar P R, Nowak M A, Monard S, Segal J P, Cao Y, Rowland-Jones S L, Cerundolo V, Hurley A, Markowitz M, Ho D D, Nixon D F, McMichael A J. Quantitation of HIV-1-specific cytotoxic T lymphocytes and plasma load of viral RNA. Science. 1998; 279:2103-2106. [PubMed: 9516110]

Pancera M, Zhou T, Druz A, Georgiev I S, Soto C, Gorman J, Huang J, Acharya P, Chuang G Y, Ofek G, Stewart-Jones G B, Stuckey J, Bailer R T, Joyce M G, Louder M K, Tumba N, Yang Y, Zhang B, Cohen M S, Haynes B F, Mascola J R, Morris L, Munro J B, Blanchard S C, Mothes W, Connors M, Kwong P D. Structure and immune recognition of trimeric pre-fusion HIV-1 Env. Nature. 2014; 514:455-461. [PubMed: 25296255]

Pantaleo G, Esteban M, Jacobs B, Tartaglia J. Poxvirus vector-based HIV vaccines. Curr Opin HIV AIDS. 2010; 5:391-396. [PubMed: 20978379]

Parker C E, Deterding L J, Hager-Braun C, Binley J M, Schulke N, Katinger H, Moore J P, Tomer K B. Fine definition of the epitope on the gp41 glycoprotein of human immunodeficiency virus type 1 for the neutralizing monoclonal antibody 2F5. J Virol. 2001; 75:10906-10911. [PubMed: 11602730]

Pastori C, Barassi C, Piconi S, Longhi R, Villa M L, Siccardi A G, Clerici M, Lopalco L. HIV neutralizing IgA in exposed seronegative subjects recognise an epitope within the gp41 coiled-coil pocket. J Biol Regul Homeost Agents. 2000; 14:15-21. [PubMed: 10763886]

Perdiguero B, Gomez C E, Cepeda V, Sanchez-Sampedro L, Garcia-Arriaza J, Mejias-Perez E, Jimenez V, Sanchez C, Sorzano C O, Oliveros J C, Delaloye J, Roger T, Calandra T, Asbach B, Wagner R, Kibler K V, Jacobs B L, Pantaleo G, Esteban M. Virological and immunological characterization of novel NYVAC-based HIV/AIDS vaccine candidates expressing clade C trimeric soluble gp140(ZM96) and Gag(ZM96)-Pol-Nef(CN54) as virus-like particles. J Virol. 2015; 89:970-988. [PubMed: 25355891]

Perreau M, Welles H C, Harari A, Hall O, Martin R, Maillard M, Dorta G, Bart P A, Kremer E J, Tartaglia J, Wagner R, Esteban M, Levy Y, Pantaleo G. DNA/NYVAC vaccine regimen induces HIV-specific CD4 and CD8 T-cell responses in intestinal mucosa. J Virol. 2011; 85:9854-9862. [PubMed: 21775454]

Peyret H, Lomonossoff G P (2013) The pEAQ vector series: the easy and quick way to produce recombinant proteins in plants. Plant molecular biology 83: 51-58

Pillay S, Shephard E G, Meyers A E, Williamson A L, Rybicki E P. HIV-1 sub-type C chimaeric VLPs boost cellular immune responses in mice. J Immune Based Ther Vaccin. 2010; 8:7.

Pollara J, McGuire E, Fouda G G, Rountree W, Eudailey J, Overman R G, Seaton K E, Deal A, Edwards R W, Tegha G, Kamwendo D, Kumwenda J, Nelson J A, Liao H X, Brinkley C, Denny T N, Ochsenbauer C, Ellington S, King C C, Jamieson D J, van der Horst C, Kourtis A P, Tomaras G D, Ferrari G, Permar S R. Association of HIV-1 envelope-specific breast milk IgA responses with reduced risk of postnatal mother-to-child transmission of HIV-1. J Virol. 2015; 89:9952-9961. [PubMed: 26202232]

Postler T S, Desrosiers R C. The tale of the long tail: the cytoplasmic domain of HIV-1 gp41. J Virol. 2013; 87:2-15. [PubMed: 23077317]

Prentice H A, Tomaras G, Geraghty D E, Apps R, Fong Y, Ehrenberg P K, Rolland M, Kijak G H, Krebs S J, Nelson W, DeCamp A, Shen X, Yates N L, Zolla-Pazner S, Nitayaphan S, Rerks-Ngarm S, Kaewkungwal J, Pitisuttihum P, Ferrari G, McElrath M J, Montefiori D, Bailer R T, Koup R A, O'Connell R J, Robb M L, Michael N L, Gilbert P B, Kim J H, Thomas R. HLA class II genes modulates vaccine-induced antibody responses to affect HIV-1 acquisition. Sci Transl Med. 2015; 7:296ra112.

Purtscher M, Trkola A, Gruber G, Buchacher A, Predl R, Steindl F, Tauer C, Berger R, Barrett N, Jungbauer A, Katinger H (1994) A broadly neutralizing human monoclonal antibody against gp41 of Human Immunodeficiency Virus Type 1. AIDS Research and Human Retroviruses 10: 1651-1658

Quakkelaar E D, Redeker A, Haddad E K, Harari A, McCaughey S M, Duhen T, Filali-Mouhim A, Goulet J P, Loof N M, Ossendorp F, Perdiguero B, Heinen P, Gomez C E, Kibler K V, Koelle D M, Sekaly R P, Sallusto F, Lanzavecchia A, Pantaleo G, Esteban M, Tartaglia J, Jacobs B L, Melief C J. Improved innate and adaptive immunostimulation by genetically modified HIV-1 protein expressing NYVAC vectors. PLoS One. 2011; 6:e16819. [PubMed: 21347234]

Rerks-Ngarm S, Pitisuttithum P, Nitayaphan S, Kaewkungwal J, Chiu J, Paris R, Premsri N, Namwat C, de Souza M, Adams E, Benenson M, Gurunathan S, Tartaglia J, McNeil J G, Francis D P, Stablein D, Birx D L, Chunsuttiwat S, Khamboonruang C, Thongcharoen P, Robb M L, Michael L, Kunasol P, Kim J H. Vaccination with ALVAC and AIDSVAX to Prevent HIV-1 Infection in Thailand. N Engl J Med. 2009 (doi:NEJMoa0908492) (pii) (10.1056/NEJMoa0908492).

Rodriguez-Negrete E A, Carrillo-Tripp J, Rivera-Bustamante R F (2009) RNA silencing against geminivirus: complementary action of posttranscriptional gene silencing and transcriptional gene silencing in host recovery. Journal of virology 83: 1332-1340

Rosales-Mendoza S, Rubio-Infante N, Govea-Alonso D O, Moreno-Fierros L (2012) Current status and perspectives of plant-based candidate vaccines against the human immunodeficiency virus (HIV). Plant Cell Rep 31: 495-511

Rosales-Mendoza S, Rubio-Infante N, Monreal-Escalante E, Govea-Alonso D O, Garcia-Hernández A L, Salazar-Gonzalez J A, Gonzalez-Ortega O, Paz-Maldonado L M T, Moreno-Fierros L (2013) Chloroplast expression of an HIV envelop-derived multiepitope protein: towards a multivalent plant-based vaccine. Plant Cell, Tissue and Organ Culture (PCTOC) 116: 111-123

Rybicki E P. Plant-produced vaccines: promise and reality. Drug Discov Today. 2009; 14: 16-24

Rybicki E P. Plant-based vaccines against viruses. Virology J. 2014; 11:205

Rybicki E P. Plant-made vaccines for humans and animals. Plant Biotechnol J. 2010; 8:620-637. [PubMed: 20233333]

Sagar M, Akiyama H, Etemad B, Ramirez N, Freitas I, Gummuluru S. Transmembrane domain membrane proximal external region but not surface unit-directed broadly neutralizing hiv-1 antibodies can restrict dendritic cell-mediated HIV-1 trans-infection. J Infect Dis. 2012; 205: 1248-1257. [PubMed: 22396600]

Sainsbury F, Thuenemann E C, Lomonossoff G P (2009) pEAQ: versatile expression vectors for easy and quick transient expression of heterologous proteins in plants. Plant biotechnology journal 7: 682-693

Sala F, Rigano M M, Barbante A, Basso B, Walmsley A M, Castiglione S (2003) Vaccine antigen production in transgenic plants: strategies, gene constructs and perspectives. Vaccine 21: 803-808

Sanders R W, van Gils M J, Derking R, Sok D, Ketas T J, Burger J A, Ozorowski G, Cupo A, Simonich C, Goo L, Arendt H, Kim H J, Lee J H, Pugach P, Williams M, Debnath G, Moldt B, van Breemen M J, Isik G, Medina-Ramirez M, Back J W, Koff W C, Julien J P, Rakasz E G, Seaman M S, Guttman M, Lee K K, Klasse P J, LaBranche C, Schief W R, Wilson I A, Overbaugh J, Burton D R, Ward A B, Montefiori D C, Dean H, Moore J P. HIV-1 VACCINES. HIV-1 neutralizing antibodies induced by native-like envelope trimers. Science. 2015; 349:aac4223. [PubMed: 26089353]

Schneider C A, Rasband W S, Eliceiri K W (2012) NIH Image to ImageJ: 25 years of image analysis. Nature Methods 9: 671-675

Scotti N, Alagna F, Ferraiolo E, Formisano G, Sannino L, Buonaguro L, De Stradis A, Vitale A, Monti L, Grillo S, Buonaguro F M, Cardi T (2009) High-level expression of the HIV-1 Pr55gag polyprotein in transgenic tobacco chloroplasts. Planta 229: 1109-1122

Scotti N, Rybicki E P. Virus-like particles produced in plants as potential vaccines. Expert Rev Vaccin. 2013; 12:211-224.

Seemanpillai M, Dry I, Randles J, Rezaian A (2003) Transcriptional Silencing of Geminiviral Promoter-Driven Transgenes Following Homologous Virus Infection. Molecular Plant-Microbe Interactions 16: 429-438

Sellhorn G, Kraft Z, Caldwell Z, Ellingson K, Mineart C, Seaman M S, Montefiori D C, Lagerquist E, Stamatatos L. Engineering, expression, purification, and characterization of stable clade A B recombinant soluble heterotrimeric gp140 proteins. J Virol. 2012; 86:128-142. [PubMed: 22031951]

Shen R, Drelichman E R, Bimczok D, Ochsenbauer C, Kappes J C, Cannon J A, Tudor D, Bomsel M, Smythies L E, Smith P D. GP41-specific antibody blocks cell-free HIV type 1 transcytosis through human rectal mucosa and model colonic epithelium. J Immunol. 2010; 184:3648-3655. [PubMed: 20208001]

Silhavy D, Molnar A, Lucioli A, Szittya G, Hornyik C, Tavazza M, Burgyan J (2002) A viral protein suppresses RNA silencing and binds silencing-generated, 21- to 25-nucleotide double-stranded RNAs. The EMBO Journal 21: 3070-3080

Snapper C M, Paul W E. Interferon-gamma and B cell stimulatory factor-1 reciprocally regulate Ig isotype production. Science. 1987; 236:944-947. [PubMed: 3107127]

Spok A, Twyman R M, Fischer R, Ma J K, Sparrow P A (2008) Evolution of a regulatory framework for pharmaceuticals derived from genetically modified plants. Trends Biotechnol 26: 506-518

Spreitzer R J, Salvucci M E (2002) Rubisco: structure, regulatory interactions, and possibilities for a better enzyme. Annu Rev Plant Biol 53: 449-475

Stephenson K E, Li H, Walker B D, Michael N L, Barouch D H. Gag-specific cellular immunity determines in vitro viral inhibition and in vivo virologic control following SIV challenges of vaccinated monkeys. Retrovirology. 2012; 9:245.

Szabo S J, Sullivan B M, Peng S L, Glimcher L H. Molecular mechanisms regulating Th1 immune responses. Annu Rev Immunol. 2003; 21:713-758. [PubMed: 12500979]

Tartaglia J, Cox W I, Taylor J, Perkus M, Riviere M, Meignier B, Paoletti E. Highly attenuated poxvirus vectors. AIDS Res Hum Retrovir. 1992b; 8:1445-1447. [PubMed: 1466978]

Tartaglia J, Perkus M E, Taylor J, Norton E K, Audonnet J C, Cox W I, Davis S W, van der Hoeven J, Meignier B, Riviere M, et al. NYVAC: a highly attenuated strain of vaccinia virus. Virology. 1992a; 188:217-232. [PubMed: 1566575]

Taylor J, Paoletti E. Fowlpox virus as a vector in non-avian species. Vaccine. 1988; 6:466-468. [PubMed: 2854335]

Taylor J, Weinberg R, Languet B, Desmettre P, Paoletti E. Recombinant fowlpox virus inducing protective immunity in non-avian species. Vaccine. 1988; 6:497-503. [PubMed: 2854338]

Team AVEGP. Cellular and humoral immune responses to a canarypox vaccine containing human immunodeficiency virus type 1 Env, Gag, and Pro in combination with RGP120. J Infect Dis. 2001; 183:563-570. [PubMed: 11170981]

Tudor D, Bomsel M. The broadly neutralizing HIV-1 IgG 2F5 elicits gp41-specific antibody-dependent cell cytotoxicity in a FcgammaRI-dependent manner. AIDS. 2011; 25:751-759. [PubMed: 21330910]

Tudor D, Derrien M, Diomede L, Drillet A S, Houimel M, Moog C, Reynes J M, Lopalco L, Bomsel M. HIV-1 gp41-specific monoclonal mucosal IgAs derived from highly exposed but IgG-seronegative individuals block HIV-1 epithelial transcytosis and neutralize CD4(+) cell infection: an IgA gene and functional analysis. Mucosal Immunol. 2009; 2:412-426. [PubMed: 19587640]

Tudor D, Yu H, Maupetit J, Drillet A S, Bouceba T, Schwartz-Cornil I, Lopalco L, Tuffery P, Bomsel M. Isotype modulates epitope specificity, affinity, and antiviral activities of anti-HIV-1 human broadly neutralizing 2F5 antibody. Proc Natl Acad Sci USA. 2012; 109:12680-12685. [PubMed: 22723360]

Verkoczy L, Chen Y, Bouton-Verville H, Zhang J, Diaz M, Hutchinson J, Ouyang Y B, Alam S M, Holl T M, Hwang K K, Kelsoe G, Haynes B F. Rescue of HIV-1 broad neutralizing antibody-expressing B cells in 2F5 VH×VL knockin mice reveals multiple tolerance controls. J Immunol. 2011; 187:3785-3797. [PubMed: 21908739]

Verkoczy L, Chen Y, Zhang J, Bouton-Verville H, Newman A, Lockwood B, Scearce R M, Montefiori D C, Dennison S M, Xia S M, Hwang K K, Liao H X, Alam S M, Haynes B F. Induction of HIV-1 broad neutralizing antibodies in 2F5 knock-in mice: selection against membrane proximal external region-associated autoreactivity limits T-dependent responses. J Immunol. 2013; 191:2538-2550. [PubMed: 23918977]

Verkoczy L, Diaz M, Holl T M, Ouyang Y B, Bouton-Verville H, Alam S M, Liao H X, Kelsoe G, Haynes B F. Autoreactivity in an HIV-1 broadly reactive neutralizing antibody variable region heavy chain induces immunologic tolerance. Proc Natl Acad Sci USA. 2010; 107:181-186. [PubMed: 20018688]

Voinnet O, Rivas S, Mestre P, Baulcombe D (2003) An enhanced transient expression system in plants based on suppression of gene silencing by the p19 protein of tomato bushy stunt virus. The Plant Journal 33: 949-956

Wan Y, Liu L, Wu L, Huang X, Ma L, Xu J. Deglycosylation or partial removal of HIV-1 CN54 gp140 V1/V2 domain enhances env-specific T cells. AIDS Res Hum Retrovir. 2009; 25:607-617. [PubMed: 19500018]

Wilken L R, Nikolov Z L (2012) Recovery and purification of plant-made recombinant proteins. Biotechnology Advances 30: 419-433

Williams W B, Liao H X, Moody M A, Kepler T B, Alam S M, Gao F, Wiehe K, Trama A M, Jones K, Zhang R, Song H, Marshall D J, Whitesides J F, Sawatzki K, Hua A, Liu P, Tay M Z, Seaton K E, Shen X, Foulger A, Lloyd K E, Parks R, Pollara J, Ferrari G, Yu J S, Vandergrift N, Montefiori D C, Sobieszczyk M E, Hammer S, Karuna S, Gilbert P, Grove D, Grunenberg N, McElrath M J, Mascola J R, Koup R A, Corey L, Nabel G J, Morgan C, Churchyard G, Maenza J, Keefer M, Graham B S, Baden L R, Tomaras G D, Haynes B F. HIV-1 VACCINES. Diversion of HIV-1 vaccine-induced immunity by gp41-microbiota cross-reactive antibodies. Science. 2015; 349: aab1253. [PubMed: 26229114]

Williamson, A L., Rybicki, E P. Justification for the inclusion of Gag in HIV vaccine candidates. Expert Rev Vaccin. 2015. http://dx.doi.org/10.1586/14760584.2016.1129904: 1-14

Yates N L, Liao H X, Fong Y, deCamp A, Vandergrift N A, Williams W T, Alam S M, Ferrari G, Yang Z Y, Seaton K E, Berman P W, Alpert M D, Evans D T, O'Connell R J, Francis D, Sinangil F, Lee C, Nitayaphan S, Rerks-Ngarm S, Kaewkungwal J, Pitisuttithum P, Tartaglia J, Pinter A, Zolla-Pazner S, Gilbert P B, Nabel G J, Michael N L, Kim J H, Montefiori D C, Haynes B F, Tomaras G D. Vaccine-induced Env V1-V2 IgG3 correlates with lower HIV-1 infection risk and declines soon after vaccination. Sci Transl Med. 2014; 6:228ra239.

Yildiz I, Shukla S, Steinmetz N F (2011) Applications of viral nanoparticles in medicine. Current opinion in biotechnology 22: 901-908

Yusibov V, Streatfield S J, Kushnir N (2014) Clinical development of plant-produced recombinant pharmaceuticals: Vaccines, antibodies and beyond. Human Vaccines 7: 313-321

Zhang R, Verkoczy L, Wiehe K, Alam S M, Nicely N I, Santra S, Bradley T, Pemble IV C W, Zhang J, Gao F, Montefiori D, Bouton-Verville H, Kelsoe G, Larimore K, Trama A M, Vandergrift N A, Tomaras G, Kepler T B, Moody M A, Liao H X, Haynes B F (2016) Initiation of immune tolerance-controlled HIV-gp41 neutralizing B cell lineages. Science Translational Medicine 8: 336ra362

Zimran A, Brill-Almon E, Chertkoff R, Petakov M, Blanco-Favela F, Munoz E T, Solorio-Meza S E, Arnato D, Duran G, Giona F, Heitner R, Rosenbaum H, Giraldo P, Mehta A, Park G, Phillips M, Elstein D, Altarescu G, Szleifer M, Hashmueli S, Aviezer D (2011) Pivotal trial with plant cell-expressed recombinant gucocerebrosidase taligluc-erase alfa, a novel enzyme replacement therapy for Gaucher disease. Blood 118: 5767-5773

Zolla-Pazner S. Identifying epitopes of HIV-1 that induce protective antibodies. Nat Rev Immunol. 2004; 4:199-210. [PubMed: 15039757].

Zwick M B, Labrijn A F, Wang M, Spenlehauer C, Saphire E O, Binley J M, Moore J P, Stiegler G, Katinger H, Burton D R, Parren P W (2001) Broadly neutralizing antibodies targeted to the membrane-proximal external region of human immunodeficiency virus type 1 glycoprotein gp41. J Virol 75: 10892-10905

We claim:

1. A method of generating an immune response in a mammalian subject against HIV comprising:
   administering a vaccinia virus-like particle (VLP) to the mammalian subject, wherein the vaccinia VLP presents HIV Gag, a fragment of gp41, or both; and
   administering a plant-produced HIV VLP to the mammalian subject, wherein the plant-produced HIV VLP presents HIV Gag and a fragment of gp41 and is isolated from plant tissue transformed with a dual replicon geminivirus-based plant expression vector comprising a T-DNA region that comprises:
   a first nucleic acid sequence encoding Gag and a first promoter region upstream of the first nucleic acid sequence encoding Gag; and
   a second nucleic acid sequence encoding a fragment of gp41 and a second promoter upstream of the second nucleic acid sequence encoding a fragment of gp41, wherein the mammalian subject is administered the vaccinia VLP and the plant-produced HIV VLP in an amount sufficient to generate an HIV immune response in the mammalian subject.

2. The method of claim 1, wherein the molar ratio of HIV Gag and the fragment of gp41 expressed by the plant produced HIV VLP is 1.7 to 11.8.

3. The method of claim 1, wherein the fragment of gp41 is dgp41.

4. The method of claim 1, wherein the vaccinia VLP administered presents both Gag and dgp41.

5. The method of claim 1, wherein the mammalian subject is administered the vaccinia VLP at least 30 days prior to the administration of the plant-produced HIV VLP.

6. The method of claim 1 further comprising administering to the mammalian subject a second dose of the plant-produced HIV VLP.

7. The method of claim 1, wherein the vaccinia VLP is isolated from a mammalian cell transfected with at least one replicating but highly attenuated vaccinia virus vector selected from the group consisting of:
   a first replicating but highly attenuated vaccinia virus vector comprising a third nucleic acid sequence encoding Gag,
   a second replicating but highly attenuated vaccinia virus vector comprising a fourth nucleic acid sequence encoding a fragment of gp41, and
   a third replicating but highly attenuated vaccinia virus vector comprising the third nucleic acid sequence encoding Gag and the fourth nucleic acid sequence encoding fragment of gp41.

8. The method of claim 7, wherein the replicating but highly attenuated vaccinia virus vector is NYVAC.

9. The method of claim 1, wherein the T-DNA region of the geminivirus-based vector plant expression vector further comprises a nucleic acid sequence encoding at least one replication gene.

10. The composition of claim 9, wherein the geminivirus-based vector is a bean yellow mosaic virus-based vector, the nucleic acid sequence encoding at least one replication gene that encodes Rep/RepA.

11. The method of claim 10, wherein the first promoter region and the second promoter region comprise a nucleic acid sequence encoding the cauliflower mosaic virus 35S promoter (P35).

12. The method of claim 11, wherein the first promoter region and the second promoter region further comprise two translation enhancer binding sites downstream of nucleic acid sequence encoding P35.

13. The method of claim 12, wherein the T-DNA region of the plant expression vector further comprises a pair of long intergenic regions, wherein the pair of long intergenic regions flank a portion of the T-DNA region that does not comprise the nucleic acid sequence encoding the silencing suppressor protein and does comprise the at least one replication gene, the first nucleic acid sequence encoding Gag and the first promoter region upstream of the first nucleic acid sequence encoding Gag; and/or the second nucleic acid sequence encoding a fragment of gp41 and a second promoter upstream of the second nucleic acid sequence encoding a fragment of gp41.

14. The method of claim 13, wherein the second nucleic acid sequence encoding the fragment of gp41 comprises the nucleic acid sequence of dgp41.

15. The method of claim 9, wherein the T-DNA region of the plant expression vector further comprises a nucleic acid sequence encoding a silencing suppressor protein, wherein the nucleic acid sequence encoding the silencing suppressor protein is upstream of the first nucleic acid sequence encoding Gag and the first promoter region upstream of the first nucleic acid sequence encoding Gag and upstream of the second nucleic acid sequence encoding a fragment of gp41 and a second promoter upstream of the second nucleic acid sequence encoding a fragment of gp41.

16. The method of claim 9, wherein the T-DNA region of the plant expression vector further comprises a nucleic acid sequence encoding barley α-amylase signal peptide, wherein the nucleic acid sequence encoding barley α-amylase signal peptide is upstream of the second nucleic acid sequence encoding a fragment of gp41 and downstream of the second promoter region.

17. A method of generating an HIV immune response in a mammalian subject, the method comprising:
    administering a vaccinia virus-like particle (VLP) to the mammalian subject, wherein the vaccinia VLP presents HIV Gag and a fragment of gp41; and
    administering a plant-produced HIV VLP to the mammalian subject, wherein the plant-produced HIV VLP presents HIV Gag and a fragment of gp41 and is isolated from plant tissue transformed with a geminivirus-based plant expression vector,
    wherein the vaccinia VLP is isolated from a mammalian cell transfected with at least one replicating but highly attenuated vaccinia virus vector and the mammalian subject is administered the vaccinia VLP and the plant-produced HIV VLP in an amount sufficient to generate an HIV immune response in the mammalian subject.

18. The method of claim 17, wherein
the geminivirus-based plant expression vector comprises a T-DNA region comprising:
    a first nucleic acid sequence encoding Gag and a first promoter region upstream of the first nucleic acid sequence encoding Gag; and
    a second nucleic acid sequence encoding a fragment of gp41 and a second promoter upstream of the second nucleic acid sequence encoding a fragment of gp41; and
the at least one replicating but highly attenuated vaccinia virus vector is selected from the group consisting of:
    a first replicating but highly attenuated vaccinia virus vector comprising a third nucleic acid sequence encoding Gag,
    a second replicating but highly attenuated vaccinia virus vector comprising a fourth nucleic acid sequence encoding a fragment of gp41, and
    a third replicating but highly attenuated vaccinia virus vector comprising the third nucleic acid sequence encoding Gag and the fourth nucleic acid sequence encoding fragment of gp41.

19. The method of claim 1, wherein the vaccinia VLP is administered to the mammalian subject first and the plant-produced HIV VLP is administered to the mammalian subject second.

* * * * *

SEQUENCE LISTING

```
<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: primer
```

<400> SEQUENCE: 1
actagtatgg gagctagagc ctct                                    24

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cccgggttat tgagaggaag                                         20

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
actagtatgg gatctcaaac tcaacaa                                 27

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
cccgggttat tgcaaagca                                          19

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cccacccgct ttttatagta a                                       21

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cggtttatct aacgacacaa ca                                      22

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
gagatgtaca atgggagcta gagcctct                                28

<210> SEQ ID NO 8

```
<211> LENGTH: 27
<212> TYPE: DNA
<213> ORGANISM: Artificial Sequence
<220> FEATURE:
<223> OTHER INFORMATION: primer

<400> SEQUENCE: 8
gagaggtacc ttattgagag gaagggt                                        27

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
gaggagctta ggtctctgta caacacagtg gct                                 33

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
agccactgtg ttgtacagag acctaagctc ctc                                 33

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
gaggagctta ggtctctcta caacacagtg gct                                 33

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agccactgtg ttgtagagag acctaagctc ctc                                 33

<210> SEQ ID NO 13
<211> LENGTH: 8
<212> TYPE: PRT
<213> ORGANISM: Human immunodeficiency virus type 1

<400> SEQUENCE: 13

Leu Arg Ser Leu Tyr Asn Thr Val
1               5

<210> SEQ ID NO 14
<211> LENGTH: 8
<212> TYPE: PRT
<213> ORGANISM: Human immunodeficiency virus type 1

<400> SEQUENCE: 14

Val Ile Pro Met Phe Thr Ala Leu
1               5
```

```
<210> SEQ ID NO 15
<211> LENGTH: 8
<212> TYPE: PRT
<213> ORGANISM: Human immunodeficiency virus type 1

<400> SEQUENCE: 15

Ala Met Gln Met Leu Lys Asp Thr
1               5

<210> SEQ ID NO 16
<211> LENGTH: 9
<212> TYPE: PRT
<213> ORGANISM: Human immunodeficiency virus type 1

<400> SEQUENCE: 16

Tyr Ser Pro Val Ser Ile Leu Asp Ile
1               5

<210> SEQ ID NO 17
<211> LENGTH: 10
<212> TYPE: PRT
<213> ORGANISM: Human immunodeficiency virus type 1

<400> SEQUENCE: 17

Glu Val Lys Asn Trp Met Thr Asp Thr Leu
1               5                   10
```